US008299042B2

(12) United States Patent
Pachuk

(10) Patent No.: US 8,299,042 B2
(45) Date of Patent: Oct. 30, 2012

(54) METHODS AND COMPOSITIONS FOR SILENCING GENES WITHOUT INDUCING TOXICITY

(75) Inventor: Catherine J. Pachuk, Lansdale, PA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 429 days.

(21) Appl. No.: 12/237,049

(22) Filed: Sep. 24, 2008

(65) Prior Publication Data
US 2009/0137514 A1    May 28, 2009

Related U.S. Application Data

(63) Continuation of application No. 10/425,006, filed on Apr. 28, 2003, now abandoned.

(60) Provisional application No. 60/375,636, filed on Apr. 26, 2002.

(51) Int. Cl.
C12N 15/00        (2006.01)

(52) U.S. Cl. .................................................. 514/44 A
(58) Field of Classification Search ................. 514/44 A
See application file for complete search history.

(56) References Cited

U.S. PATENT DOCUMENTS

| 4,283,393 | A |   | 8/1981  | Field et al.        |        |
|-----------|---|---|---------|---------------------|--------|
| 4,897,355 | A |   | 1/1990  | Eppstein et al.     |        |
| 5,107,065 | A |   | 4/1992  | Shewmaker et al.    |        |
| 5,264,618 | A |   | 11/1993 | Felgner et al.      |        |
| 5,279,833 | A |   | 1/1994  | Rose                |        |
| 5,283,184 | A |   | 2/1994  | Jorgensen et al.    |        |
| 5,283,185 | A |   | 2/1994  | Epand et al.        |        |
| 5,422,241 | A |   | 6/1995  | Goldrick et al.     |        |
| 5,459,127 | A |   | 10/1995 | Felgner et al.      |        |
| 5,583,021 | A |   | 12/1996 | Dougherty et al.    |        |
| 5,593,972 | A |   | 1/1997  | Weiner et al.       |        |
| 5,639,595 | A |   | 6/1997  | Mirabelli et al.    |        |
| 5,703,055 | A |   | 12/1997 | Felgner et al.      |        |
| 5,792,751 | A |   | 8/1998  | Ledley et al.       |        |
| 5,837,533 | A |   | 11/1998 | Boutin              |        |
| 5,849,727 | A |   | 12/1998 | Porter et al.       |        |
| 5,880,276 | A |   | 3/1999  | Hammarskjold et al. |        |
| 5,922,602 | A |   | 7/1999  | Kumagai et al.      |        |
| 5,932,241 | A |   | 8/1999  | Gorman              |        |
| 5,935,936 | A |   | 8/1999  | Fasbender et al.    |        |
| 5,962,428 | A |   | 10/1999 | Carrano et al.      |        |
| 5,981,505 | A |   | 11/1999 | Weiner et al.       |        |
| 6,030,785 | A | * | 2/2000  | Katze et al. ....... | 435/6  |
| 6,127,170 | A |   | 10/2000 | Boutin              |        |
| 6,197,755 | B1|   | 3/2001  | Carrano et al.      |        |
| 6,217,900 | B1|   | 4/2001  | Ciccarelli et al.   |        |
| 6,271,208 | B1|   | 8/2001  | Bischoff            |        |
| 6,482,804 | B1|   | 11/2002 | Musunuri et al.     |        |
| 6,596,268 | B1| * | 7/2003  | Coffey et al. ..... | 424/93.2 |
| 2002/0055174 | A1 |   | 5/2002 | Rittner et al.     |        |
| 2002/0065213 | A1 |   | 5/2002 | Debs et al.        |        |
| 2002/0114784 | A1 |   | 8/2002 | Li et al.          |        |
| 2002/0132257 | A1 |   | 9/2002 | Giordano et al.    |        |
| 2002/0162126 | A1 | * | 10/2002 | Beach et al. .... | 800/8  |
| 2003/0203868 | A1 | * | 10/2003 | Bushman et al. .. | 514/44 |
| 2004/0152117 | A1 | * | 8/2004 | Giordano et al. . | 435/6  |
| 2004/0235764 | A1 |   | 11/2004 | Billy et al.      |        |
| 2006/0009409 | A1 | * | 1/2006 | Woolf ............. | 514/44 |

FOREIGN PATENT DOCUMENTS

| EP | 0 242 016    | 10/1987 |
| EP | 1 229 134    | 8/2002  |
| WO | WO 94/13793  | 6/1994  |
| WO | WO 94/16737  | 8/1994  |
| WO | WO 96/10038  | 4/1996  |
| WO | WO 96/20951  | 7/1996  |
| WO | WO 97/35965  | 10/1997 |
| WO | WO 97/48793  | 12/1997 |
| WO | WO 98/05770  | 2/1998  |
| WO | WO 98/36083  | 8/1998  |
| WO | WO 99/32619  | 7/1999  |
| WO | WO 99/38537  | 8/1999  |
| WO | WO 99/49029  | 9/1999  |
| WO | WO 99/53050  | 10/1999 |
| WO | WO 99/61631  | 12/1999 |
| WO | WO 99/61636  | 12/1999 |
| WO | WO 00/01846  | 1/2000  |
| WO | WO 00/44895  | 8/2000  |
| WO | WO 00/44914  | 8/2000  |
| WO | WO 00/49035  | 8/2000  |
| WO | WO 00/63364  | 10/2000 |
| WO | WO 01/04313  | 1/2001  |
| WO | WO 01/29058  | 4/2001  |
| WO | WO 01/36646  | 5/2001  |
| WO | WO 01/68836  | 9/2001  |
| WO | WO 01/75164  | 10/2001 |
| WO | WO 01/88121  | 11/2001 |

OTHER PUBLICATIONS

Bevilacqua et al. Biochemistry 1998, 376303-6316.*
Wu et al. The Journal of Biological Chemistry 272:1291-1296,1997.*
Elbashir et al., Methods, 26:199-213 (2002).
Gunnery et al., Methods: A Companion to Methods in Enzymology, 15:189-198 (1998).
Hannon and Rossi, Nature, 431:371-378 (2004).
Harborth et al., J. Cell Science, 114:4557-4558 (2001).

(Continued)

Primary Examiner — Brian Whiteman
(74) Attorney, Agent, or Firm — Nixon Peabody LLP

(57) ABSTRACT

The present invention provides methods of post-transcriptional gene silencing which involve the use of a first dsRNA having substantial sequence identity to a target nucleic acid and a short, second dsRNA which inhibits dsRNA-mediated toxicity. These methods can be used to prevent or treat a disease or infection by silencing a gene associated with the disease or infection. The invention also provides methods for identifying nucleic acid sequences that modulate a detectable phenotype, including the function of a cell, the expression of a gene, or the biological activity of a target polypeptide.

43 Claims, 5 Drawing Sheets

OTHER PUBLICATIONS

Lu et al., RNA Interference Technology, Cambridge, Appasani, ed. (2005).
Manche et al., Molecular and Cellular Biology, 12:5238-5248 (1992).
Samarsky et al., RNA Interference Technology, Cambridge, Appasani, ed. (2005).
Simeoni et al., RNA Silencing, Methods and Protocols (Human Press, 2005).
Sioud, RNA Silencing, Methods and Protocols (Humana Press, 2005).
Sledz et al., Nature Cell Biology, 5:834-839 (2003).
Zheng et al., RNA, 10:1934-1945 (2004).
Amirthalingam et al., "Embryonic Expression and DNA-Binding Properties of Zebrafish Pax-6," *Biochem. Biophys. Res. Commun.* 215:122-128 (1995).
Angell and Baulcombe, "Consistent Gene Silencing in Transgenic Plants Expressing a Replicating Potato Virus X RNA," *EMBO J.* 16:3675-3684 (1997).
Barstead, "Genome-Wide RNAi," *Curr. Opin. Chem. Biol.* 5:63-66 (2001).
Bahramian and Zarbl, "Transcriptional and Posttranscriptional Silencing of Rodent α1 (I) Collagen by a Homologous Transcriptionally Self-Silenced Transgene," *Mol. Cell. Biol.* 19:274-283 (1999).
Baulcombe and English, "Ectopic Pairing of Homologous DNA and Post-Transcriptional Gene Silencing in Transgenic Plants," *Curr. Opin. Biotechnol.* 7:173-180 (1996).
Baulcombe, "Mechanisms of Pathogen-Derived Resistance to Viruses in Transgenic Plants," *Plant Cell* 8:1833-1844 (1996).
Baulcombe, "Gene Silencing: RNA Makes RNA Makes No Protein," *Curr. Biol.* 9:R599-R601 (1999).
Baulcombe, "RNA Silencing: Diced Defence," *Nature* 409:295-296 (2001).
Benfey and Chua, "Regulated Genes in Transgenic Plants," *Science* 244:174-181 (1989).
Bernstein et al., "Role for a Bidentate Ribonuclease in the Initiation Step of RNA Interference," *Nature* 409:363-366 (2001).
Branch, "A Good Antisense Molecule is Hard to Find," *Trends Biochem. Sci.* 23:45-50 (1998).
Bruening, "Plant Gene Silencing Regularized," *Proc. Nati. Acad. Sci. USA* 95:13349-13351 (1998).
Bosher and Labouesse, "RNA Interference: Genetic Wand and Genetic Watchdog," *Nat. Cell. Biol.* 2:E31-36 (2000).
Cartea et al., "Comparison of Sense and Antisense Methodologies for Modifying the Fatty Acid Composition of *Arabidopsis thaliana* Oilseed," *Plant Sci.* 136:181-194 (1998).
Caplen et al., "dsRNA-Mediated Gene Silencing in Cultured *Drosophila* Cells: A Tissue Culture Model for the Analysis of RNA Interference," *Gene* 252:95-105 (2000).
Caplen et al., "Specific Inhibition of Gene Expression by Small Double-Stranded RNAs in Invertebrate and Vertebrate Systems," *Proc. Natl. Acad. Sci. USA* 98:9742-9747 (2001).
Carthew, "Gene Silencing by Double-Stranded RNA," *Curr. Opin. Cell. Biol.* 13:244-248 (2001).
Cogoni and Marino, "Gene Silencing in *Neurospora crassa* Requires a Protein Homologous to RNA-Dependent RNA Polymerase," *Nature* 399:166-169 (1999).
Cogoni and Marino, "Posttranscriptional Gene Silencing in *Neurospora* by a RecQ DNA Helicase," *Science* 286:2342-2344 (1999).
Crooke, Handbook of Experimental Pharmacology: Antisense Research and Application, Springer-Verlag, vol. 131, Ch. 1, pp. 1-50 (1998).
Crystal, "Transfer of Genes to Humans: Early Lessons and Obstacles to Success," *Science* 270:404-410 (1995).
Ding et al., "Cell-To-Cell Movement of Potato Spindle Tuber Viroid," *Plant J.* 12:931-936 (1997).
Dougherty and Parks, "Transgenes and Gene Suppression: Telling Us Something New?" *Curr. Opin. Cell. Biol.* 7:399-405 (1995).
Elbashir et al., "Duplexes of 21-Nucleotide RNAs Mediate RNA Interference in Cultured Mammalian Cells," *Nature* 411:494-498 (2001).
Fire et al., "Production of Antisense RNA Leads to Effective and Specific Inhibition of Gene Expression in *C. elegans* Muscle," *Development* 113:503-514 (1991).
Fire et al., "Potent and Specific Genetic Interference by Double-Stranded RNA in *Caenorhabditis elegans*," *Nature* 391:806-811 (1998).
Fire, "RNA—Triggered Gene Silencing," *Trends Genet.* 15:358-363 (1999).
Flavell, "Inactivation of Gene Expression in Plants as a Consequence of Specific Sequence Duplication," *Proc. Natl. Acad. Sci. USA* 91:3490-3496 (1994).
Friedmann, "Overcoming the Obstacles to Gene Therapy," *Sci. Am.* 276:96-101 (1997).
Gale et al., "Translational Control of Viral Gene Expression in Eukaryotes," *Microbiol. Mot Biol. Rev.* 64:239-280 (2000).
Ghislain et al., "The Interferon-Inducible Stat2:Stat1 Heterodimer Preferentially Binds In Vitro to a Consensus Element Found in the Promoters of a Subset of Interferon-Stimulated Genes," *J. Interferon Cytokine Res.* 21:379-388 (2001).
Grant, "Dissecting the Mechanisms of Posttranscriptional Gene Silencing: Divide and Conquer," *Cell* 96:303-306 (1999).
Grishok et al., "Genetic Requirements for Inheritance of RNAi in *C. elegans*," *Science* 287:2494-2497 (2000).
Guo and Kemphues, "*par-1*, A Gene Required for Establishing Polarity in *C. elegans* Embryos, Encodes a Putative Ser/Thr Kinase That is Asymmetircally Distributed," *Cell* 81:611-620 (1995).
Halpern et al., "Induction of Muscle Pioneers and Floor Plate is Distinguished by the Zebrafish *no tail* Mutation," *Cell* 75:99-111 (1993).
Halpern et al., "Genetic Interactions in Zebrafish Midline Development," *Dev. Biol.* 187:154-170 (1997).
Hamada and Spanu, "Co-Suppression of the Hydrophobin Gene *HCf-1* is Correlated with Antisense RNA Biosynthesis in *Cladosporium fulvum*," *Mol. Gen. Genet.* 259:630-638 (1998).
Hamilton and Baulcombe, "A Species of Small Antisense RNA in Posttranscriptional Gene Silencing in Plants," *Science* 286:950-952 (1999).
Hammond et al., "Post-Transcriptional Gene Silencing by Double-Stranded RNA," *Nat. Rev. Genet.* 2:110-119 (2001).
Hartmann et al., "Activation of 2'-5' Oligoadenylate Synthetase by Single-Stranded and Double-Stranded RNA Aptamers," *J. Biol. Chem.* 273:3236-3246 (1998).
Herrmann et al., "Cloning of the *T* Gene Required in Mesoderm Formation in the Mouse," *Nature* 343:617-622 (1990).
Igoucheva and Yoon, "Targeted Single-Base Correction by RNA-DNA Oligonucleotides," *Hum. Gene. Ther.* 11:2307-2312 (2000).
Iordanov et al., "Activation of NF-κB by Double-Stranded RNA (dsRNA) in the Absence of Protein Kinase R and RNase L Demonstrates the Existence of Two Separate dsRNA-Triggered Antiviral Programs," *Mol. Cell. Biol.* 21:61-72 (2001).
Jaramillo et al., "The Interferon System: A Review with Emphasis on the Role of PKR in Growth Control," *Cancer Invest.* 13:327-338 (1995).
Jensen et al., "Cosuppression of *I* Transposon Activity in *Drosophila* by *I*-Containing Sense and Antisense Transgenes," *Genetics* 153:1767-1774 (1999).
Jorgensen et al., "An RNA-Based Information Superhighway in Plants," *Science* 279:1486-1487 (1998).
Kaufman, "Double-Stranded RNA-Activated Protein Kinase Mediates Virus-Induced Apoptosis: A New Role for an Old Actor," *Proc. Natl. Acad. Sci. USA* 96:11693-11695 (1999).
Ketting et al., "*mut-7* of *C. elegans*, Required for Transposon Silencing and RNA Interference, is a Homolog of Werner Syndrome Helicase and RNase D," *Cell* 99:133-141 (1999).
Kennerdell and Carthew, "Use of dsRNA-Mediated Genetic Interference to Demonstrate that *frizzled* and *frizzled 2* Act in the Wingless Pathway," *Cell* 95:1017-1026 (1998).
King and Goodbourn, "STAT1 is Inactivated by a Caspase," *J. Biol. Chem.* 273:8699-8704 (1998).
Kooter et al., "Listening to the Silent Genes: Transgene Silencing, Gene Regulation and Pathogen Control," *Trends Plant Sci.* 4:340-347 (1999).

Kumagai et al., "Cytoplasmic Inhibition of Carotenoid Biosynthesis with Virus-Derived RNA," *Proc. Natl. Acad. Sci. USA* 92:1679-1683 (1995).

Kumar and Carmichael, "Antisense RNA: Function and Fate of Duplex RNA in Cells of Higher Eukaryotes," *Microbial. Mot. Biol. Rev.* 62:1415-1434 (1998).

Lau et al., "Embryonic *XMab2112* Expression is Required for Gastrulation and Subsequent Neural Development," *Biochem. Biophys. Res. Commun.* 280:1378-1384 (2001).

Li et al., "Double-Stranded RNA Injection Produces Null Phenotypes in Zebrafish," *Dev. Biol.* 217:394-405 (2000).

Li et al., "*Erratum,*" *Dev. Biol.* 217:394-405 (2000), appears in *Dev. Biol.* 220:432 (2000).

Li et al., "RNase-L-Dependent Destabilization of Interferon-Induced mRNAs: A Role for the 2-5A System in Attenuation of the Interferon Response," *J. Biol. Chem.* 275:8880-8888 (2000).

Li and Beg, "Induction of Necrotic-Like Cell Death by Tumor Necrosis Factor Alpha and Caspase Inhibitors: Novel Mechanism for Killing Virus-Infected Cells," *J. Virol.* 74:7470-7477 (2000).

Li et al., "The RelA(p65) Subunit of NF-κB is Essential for Inhibiting Double-Stranded RNA-Induced Cytotoxicity," *J. Biol. Chem.* 276:1185-1194 (2001).

Liebhaber et al., "Translation Inhibition by an mRNA Coding Region Secondary Structure is Determined by its Proximity to the *AUG* Initiation Codon," *J. Mot Biol.* 226:609-621 (1992).

Lindbo et al., "Induction of a Highly Specific Antiviral State in Transgenic Plants: Implications for Regulation of Gene Expression and Virus Resistance," *Plant Cell* 5:1749-1759 (1993).

Litt et al., "Transitions in Histone Acetylation Reveal Boundaries of Three Separately Regulated Neighboring Loci," *EMBO J.* 20:2224-2235 (2001).

Matzke and Matzke, "Epigenetic Silencing of Plant Transgenes as a Consequence of Diverse Cellular Defence Responses," *Cell. Mol. Life Sci.* 54:94-103 (1998).

Melby et al., "Spatial Regulation of *floating head* Expression in the Developing Notochord," *Dev. Dyn.* 209:156-165 (1997).

Metzlaff et al., "RNA-Mediated RNA Degradation and Chalcone Synthase a Silencing in *Petunia,*" *Cell* 88:845-854 (1997).

Misquitta and Paterson, "Targeted Disruption of Gene Function in *Drosophila* by RNA Interference (RNA-i): A Role for *nautilus* in Embryonic Somatic Muscle Formation," *Proc. Natl. Acad. Sci. USA* 96:1451-1456 (1999).

Montgomery and Fire, "Double-Stranded RNA as a Mediator in Sequence-Specific Genetic Silencing and Co-Suppression," *Trends Genet.* 14:255-258 (1998).

Montgomery et al., "RNA as a Target of Double-Stranded RNA-Mediated Genetic Interference in *Caenorhabditis elegans,*" *Proc. Natl. Acad. Sci. USA* 95:15502-15507 (1998).

Ngô et al., "Double-Stranded RNA Induces mRNA Degradation in *Trypanosome brucei,*" *Proc. Natl. Acad. Sci. USA* 95:14687-14692 (1998).

Nishikawa and Natori, "Targeted Disruption of a Pupal Hemocyte Protein of *Sarcophaga* by RNA Interference," *Eur. J. Biochem.* 268:5295-5299 (2001).

Nüsslein-Volhard, "Of Flies and Fishes," *Science* 266:572-574 (1994).

Oates et al., "Too Much Interference: Injection of Double-Stranded RNA has Nonspecific Effects in the Zebrafish Embryo," *Dev. Biol.* 224:20-28 (2000).

Pachuk et al. "Chain Reaction Cloning: A One-Step Method for Directional Ligation of Multiple DNA Fragments," *Gene* 243:19-25 (2000).

Pachuk et al. "DNA Vaccines—Challenges in Delivery," *Curr. Opin. Mol. Ther.* 2:188-198 (2000).

Pachuk et al., "Characterization of a New Class of DNA Delivery Complexes Formed by the Local Anesthetic Bupivacaine," *Biochem. Biophys. Acta.* 1468:20-30 (2000).

Paddison et al., "Stable Suppression of Gene Expression by RNAi in Mammalian Cells," *Proc. Natl. Acad. Sci. USA* 99:1443-1448 (2002).

Palauqui et al., "Systemic Acquired Silencing: Transgene-Specific Post-Transcriptional Silencing is Transmitted by Grafting from Silenced Stocks to Non-Silenced Scions," *EMBO J.* 16:4738-4745 (1997).

Pelletier and Sonenberg, "Photochemical Cross-Linking of Cap Binding Proteins to Eucaryotic mRNAs: Effect of mRNA 5' Secondary Structure," *Mol. Cell. Biol.* 5:3222-3230 (1985).

Ratcliff et al., "A Similarity Between Viral Defense and Gene Silencing in Plants," *Science* 276:1558-1560 (1997).

Rocheleau et al., "Wnt Signaling and an APC-Related Gene Specify Endoderm in Early *C. elegans* Embryos," *Cell* 90:707-716 (1997).

Romano et al., "Inhibition of Double-Stranded RNA-Dependent Protein Kinase PKR by Vaccinia Virus E3: Role of Complex Formation and the E3 N-Terminal Domain," *Mol. Cell. Biol.* 18:7304-7316 (1998).

Ruiz et al., "Homology-Dependent Gene Silencing in *Paramecium,*" *Mot Biol. Cell* 9:931-943 (1998).

Ruiz et al., "Initiation and Maintenance of Virus-Induced Gene Silencing," *Plant Cell* 10:937-946 (1998).

Russell and Liebhaber, "Double-Stranded RNA Triggers Generalized Translational Arrest in *Xenopus* Oocytes," *Biochem. Biophys. Res. Commun.* 194:892-900 (1993).

Sánchez Alvarado and Newmark, "Double-Stranded RNA Specifically Disrupts Gene Expression During Planarian Regeneration," *Proc. Natl. Acad. Sci. USA* 96:5049-5054 (1999).

Schiebel et al., "Isolation of an RNA-Directed RNA Polymerase-Specific cDNA Clone from Tomato," *Plant Cell* 10:2087-2101 (1998).

Schofield and Caskey, "Non-Viral Approaches to Gene Therapy," *Br. Med. Bull.* 51:56-71 (1995).

Schulte-Merker et al., "The Protein Product of the Zebrafish Homologue of the Mouse *T* Gene is Expressed in Nuclei of the Germ Ring and the Notochord of the Early Embryo," *Development* 116:1021-1032 (1992).

Schulte-Merker et al., "*no tail (ntl)* is the Zebrafish Homologue of the Mouse *T (Brachyury)* Gene," *Development* 120:1009-1015 (1994).

Sharp and Zamore, "Molecular Biology RNA Interference," *Science* 287:2431-2433 (2000).

Smyth, "Gene Silencing: Cosuppression at a Distance," *Curr. Biol.* 7:R793-R795 (1997).

Smalheiser et al., "RNAi and Brain Function: Was McConnell on the Right Track?" *Trends Neurosci.* 24:216-218 (2001).

Stam et al., "Post-Transcriptional Silencing of Chalcone Synthase in *Petunia* by Inverted Transgene Repeats," *Plant J.* 12:63-82 (1997).

Svoboda et al., "Selective Reduction of Dormant Maternal mRNAs in Mouse Oocytes by RNA Interference," *Development* 127:4147-4156 (2000).

Tabara et al., "RNAi in *C. elegans*: Soaking in the Genome Sequence," *Science* 282:430-431 (1998).

Tabara et al., "The *rde-1* Gene, RNA Interference, and Transposon Silencing in *C. elegans,*" *Cell* 99:123-132 (1999).

Timmons and Fire, "Specific Interference by Ingested dsRNA," *Nature* 395:854 (1998).

Tuschl et al., "Targeted mRNA Degradation by Double-Stranded RNA in Vitro," *Genes Dev.* 13:3191-3197 (1999).

Ui-Tei et al., "Sensitive Assay of RNA Interference in *Drosophila* and Chinese Hamster Culture Cells Using Firefly Luciferase Gene as Target," *FEBS Lett.* 479:79-82 (2000).

van Blokland et al., "Transgene-Mediated Suppression of Chalcone Synthase Expression in *Petunia hybrida* Results from an Increase in RNA Turnover," *Plant J.* 6:861-877 (1994).

Verma and Somia, "Gene Therapy—Promises, Problems, and Prospects," *Nature* 389:239-242 (1997).

Voinnet and Baulcombe, "Systemic Signaling in Gene Silencing," *Nature* 389:553 (1997).

Voinnet et al., "Systemic Spread of Sequence-Specific Transgene RNA Degradation in Plants is Initiated by Localized Introduction of Ectopic Promoterless DNA," *Cell* 95:177-187 (1998).

Wagner and Sun, "Double-Stranded RNA Poses Puzzle," *Nature* 391:744-745 (1998).

Wargelius et al., "Double-Stranded RNA Induces Specific Developmental Defects in Zebrafish Embryos," *Biochem. Biophys. Res. Comm.* 263:156-161 (1999).

Wassenegger et al., "RNA-Directed *de Novo* Methylation of Genomic Sequences in Plants," *Cell* 76:567-576 (1994).

Wassenegger and Pelissier, "A Model for RNA-Mediated Gene Silencing in Higher Plants," *Plant Mol. Biol.* 37:349-362 (1998).

Waterhouse et al., "Virus Resistance and Gene Silencing in Plants Can Be Induced by Simultaneous Expression of Sense and Antisense RNA," *Proc. Natl. Acad. Sci. USA* 95:13959-13964 (1998).

Weaver et al., "Apoptosis is Promoted by the dsRNA-Activated Factor (DRAF1) During Viral Infection Independent of the Action of Interferon or p53," *FASEB J.* 15:501-514 (2001).

Wianny and Zernicka-Goetz, "Specific Interference with Gene Function by Double-Stranded RNA in Early Mouse Development," *Nat. Cell. Biol.* 2:70-75 (2000).

Willert et al., "A *Drosophila Axin* Homolog, *Daxin*, Inhibits Wnt Signaling," *Development* 126:4165-4173 (1999).

Willett et al., "Expression of Zebrafish *rag* Genes During Early Development Identifies the Thymus," *Dev. Biol.* 182:331-341 (1997).

Xie et al., "A Ribozyme-Mediated, Gene 'Knockdown' Strategy for the Identification of Gene Function in Zebrafish," *Proc. Natl. Acad. Sci. USA* 94:13777-13781 (1997).

Yang et al., "Specific Double-Stranded RNA Interference in Undifferentiated Mouse Embryonic Stem Cells," *Mol. Cell. Biol.* 21:7807-7816 (2001).

Yeung et al., "Inhibitory Role of the Host Apoptogenic Gene *PKR* in the Establishment of Persistent Infection by Encephalomyocarditis Virus in U937 Cells," *Proc. Natl. Acad. Sci. USA* 96:11860-11865 (1999).

Zamore, "RNA Interference: Listening to the Sound of Silence," *Nat. Struct. Biol.* 8:746-750 (2001).

Zhang et al., "Binding of Double-Stranded RNA to Protein Kinase PKR is Required for Dimerization and Promotes Critical Autophosphorylation Events in the Activation Loop," *J. Biol. Chem.* 276:24946-24958 (2001).

Zhao et al., "Double-Stranded RNA Injection Produces Nonspecific Defects in Zebrafish," *Dev. Biol.* 229:215-223 (2001).

\* cited by examiner

Figure 4A

SEAP short dsRNA

AA-N19 mRNA Target: (5'->3')
A.A.G . A.A.U . C.U.G . G.U.G . C.A.G . G.A.A . U.G.G     SEQ ID NO.: 1 siRNA Duplex:
G.A.A . U.G.U . G.G.U . G.C.A . G.G.A . A.U.G . G.dT.dT     SEQ ID NO.: 2
dT.dT . C.U.U . A.G.A . C.C.A . C.G.U . C.C.U . U.A.C . C     SEQ ID NO.: 3

AA-N19 mRNA Target: (5'->3')
A.A.G . A.A.G . G.A.C . A.A.A . C.U.G . G.G.G . C.C.U     SEQ ID NO.: 4 siRNA Duplex:
G.A.A . G.G.A . C.A.A . A.C.U . G.G.G . G.C.C . U.dT.dT     SEQ ID NO.: 5
dT.dT . C.U.U . C.C.U . G.U.U . U.G.A . C.C.C . C.G.G . A     SEQ ID NO.: 6

AA-N19 mRNA Target: (5'->3')
A.A.U . A.C.G . A.G.A . U.C.C . A.C.C . G.A.G . A.C.U     SEQ ID NO.: 7 siRNA Duplex:
U.A.C . G.A.G . A.U.C . C.A.C . C.G.A . G.A.C . U.dT.dT     SEQ ID NO.: 8
dT.dT . A.U.G . C.U.C . U.A.G . G.U.G . G.C.U . C.U.G . A     SEQ ID NO.: 9

Figure 4B

IL-12 short dsRNA

AA-N19 mRNA Target: (5'->3')
A.A.U . G.C.A . A.A.G . G.C.G . G.G.A . A.U.G . U.C.U          SEQ ID NO.: 10 siRNA Duplex:
U.G.C . A.A.A . G.G.C . G.G.G . A.A.U . G.U.C . U.dT.dT          SEQ ID NO.: 11
dT.dT . A.C.G . U.U.U . C.C.G . C.C.C . U.U.A . C.A.G . A        SEQ ID NO.: 12

AA-N19 mRNA Target: (5'->3')
A.A.U . C.A.G . G.G.C . U.G.C . G.U.A . G.G.U . A.C.A          SEQ ID NO.: 13 siRNA Duplex:
U.C.A . G.G.G . C.U.G . C.G.U . A.G.G . U.A.C . A.dT.dT          SEQ ID NO.: 14
dT.dT . A.G.U . C.C.C . G.A.C . G.C.A . U.C.C . A.U.G . U        SEQ ID NO.: 15

AA-N19 mRNA Target: (5'->3')
A.A.G . G.U.G . C.G.U . U.C.C . U.C.G . U.A.G . A.G.A          SEQ ID NO.: 16 siRNA Duplex:
G.G.U . G.C.G . U.U.C . C.U.C . G.U.A . G.A.G . A.dT.dT          SEQ ID NO.: 17
dT.dT . C.C.A . C.G.C . A.A.G . G.A.G . C.A.U . C.U.C . U        SEQ ID NO.: 18

```
                           SEQUENCE LISTING

<160> NUMBER OF SEQ ID NOS: 19

<210> SEQ ID NO 1
<211> LENGTH: 21
<212> TYPE: RNA
<213> ORGANISM: Homo sapiens

<400> SEQUENCE: 1
aagaaucugg ugcaggaaug g                                             21

<210> SEQ ID NO 2
<211> LENGTH: 21
<212> TYPE: DNA
<213> ORGANISM: Homo sapiens

<400> SEQUENCE: 2
gaaucuggug caggaauggt t                                             21

<210> SEQ ID NO 3
<211> LENGTH: 21
<212> TYPE: DNA
<213> ORGANISM: Homo sapiens

<400> SEQUENCE: 3
ccauuccugc accagauuct t                                             21

<210> SEQ ID NO 4
<211> LENGTH: 21
<212> TYPE: RNA
<213> ORGANISM: Homo sapiens

<400> SEQUENCE: 4
aagaaggaca aacuggggcc u                                             21

<210> SEQ ID NO 5
<211> LENGTH: 21
<212> TYPE: DNA
<213> ORGANISM: Homo sapiens

<400> SEQUENCE: 5
gaaggacaaa cugggGccut t                                             21

<210> SEQ ID NO 6
<211> LENGTH: 21
<212> TYPE: DNA
<213> ORGANISM: Homo sapiens

<400> SEQUENCE: 6
aggccccagu uuguccuuct t                                             21

<210> SEQ ID NO 7
<211> LENGTH: 21
<212> TYPE: RNA
<213> ORGANISM: Homo sapiens

<400> SEQUENCE: 7
aauacgagau ccaccgagac u                                             21
```

```
<210> SEQ ID NO 8
<211> LENGTH: 21
<212> TYPE: DNA
<213> ORGANISM: Homo sapiens

<400> SEQUENCE: 8
uacgagaucc accgagacut t                                              21

<210> SEQ ID NO 9
<211> LENGTH: 21
<212> TYPE: DNA
<213> ORGANISM: Homo sapiens

<400> SEQUENCE: 9
agucucggug gaucucguat t                                              21

<210> SEQ ID NO 10
<211> LENGTH: 21
<212> TYPE: RNA
<213> ORGANISM: Mus sp.

<400> SEQUENCE: 10
aaugcaaagg cgggaauguc u                                              21

<210> SEQ ID NO 11
<211> LENGTH: 21
<212> TYPE: DNA
<213> ORGANISM: Mus sp.

<400> SEQUENCE: 11
ugcaaaggcg ggaaugucut t                                              21

<210> SEQ ID NO 12
<211> LENGTH: 21
<212> TYPE: DNA
<213> ORGANISM: Mus sp.

<400> SEQUENCE: 12
agacauuccc gccuuugcat t                                              21

<210> SEQ ID NO 13
<211> LENGTH: 21
<212> TYPE: RNA
<213> ORGANISM: Mus sp.

<400> SEQUENCE: 13
aaucagggcu gcguagguac a                                              21

<210> SEQ ID NO 14
<211> LENGTH: 21
<212> TYPE: DNA
<213> ORGANISM: Mus sp.

<400> SEQUENCE: 14
ucagggcugc guagguacat t                                              21

<210> SEQ ID NO 15
<211> LENGTH: 21
<212> TYPE: DNA
<213> ORGANISM: Mus sp.

<400> SEQUENCE: 15
uguaccaacg cagcccugat t                                              21
```

```
-continued

<210> SEQ ID NO 16
<211> LENGTH: 21
<212> TYPE: RNA
<213> ORGANISM: Mus sp.

<400> SEQUENCE: 16
aaggugcguu ccucguagag a                                              21

<210> SEQ ID NO 17
<211> LENGTH: 21
<212> TYPE: DNA
<213> ORGANISM: Mus sp.

<400> SEQUENCE: 17
ggugcguucc ucguagagat t                                              21

<210> SEQ ID NO 18
<211> LENGTH: 21
<212> TYPE: DNA
<213> ORGANISM: Mus sp.

<400> SEQUENCE: 18
ucucuacgag gaacgcacct t                                              21

<210> SEQ ID NO 19
<211> LENGTH: 25
<212> TYPE: RNA
<213> ORGANISM: Hepatitis B virus

<400> SEQUENCE: 19
ccuccaauca cucaccaacc uccug                                          25
```

US 8,299,042 B2

METHODS AND COMPOSITIONS FOR SILENCING GENES WITHOUT INDUCING TOXICITY

CROSS REFERENCE TO RELATED APPLICATION

This application is a Continuation of, and claims priority from, U.S. patent application Ser. No. 11/542,291, filed Oct. 3, 2006, which is a Continuation of, and claims priority from, U.S. patent application Ser. No. 10/425,006, filed Apr. 28, 2003. This application claims to the benefit of the filing date of U.S. provisional patent application 60/375,636, filed Apr. 26, 2002. All of the above-referenced applications are incorporated herein by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: NUCL 015 03US SeqList_ST25.txt, date recorded: Jan. 16, 2009, file size 4 kilobytes).

BACKGROUND OF THE INVENTION

In general, the invention relates to novel methods for silencing genes. Desirably, these methods specifically inhibit the expression of one or more target genes in a cell or animal (e.g., a mammal such as a human) without inducing toxicity.

Double stranded RNA (dsRNA) has been shown to induce gene silencing in a number of different organisms. Gene silencing can occur through various mechanisms, one of which is post-transcriptional gene silencing (PTGS). In post-transcriptional gene silencing, transcription of the target locus is not affected, but the RNA half-life is decreased. Transcriptional gene silencing (TGS) is another mechanism by which gene expression can be regulated. In TGS, transcription of a gene is inhibited. Exogenous dsRNA has been shown to act as a potent inducer of PTGS in nematodes, trypanosomes, and insects. Double stranded RNA is also an inducer of TGS. Some current methods for using dsRNA in vertebrate cells to silence genes result in undesirable non-specific cytotoxicity or cell death due to the interferon response that is induced by dsRNA in vertebrate cells. Some methods also result in non-specific or inefficient silencing.

Thus, improved methods are needed for specifically silencing target genes without inducing toxicity or cell death. Desirably, these methods may be used to inhibit gene expression in in vitro samples, cell culture, and intact animals (e.g., vertebrates such as mammals).

SUMMARY OF THE INVENTION

In general, the invention features novel methods for silencing genes that produce few, if any, toxic side-effects. In particular, these methods involve administrating to a cell or animal one or more double stranded RNA (dsRNA) molecules that have substantial sequence identity to a region of a target nucleic acid and that specifically inhibit the expression of the target nucleic acid. One or more short dsRNA molecules, which differ from the dsRNA having substantial identity to the target nucleic acid, are also administered to inhibit possible toxic effects or non-specific gene silencing that may otherwise be induced by the former dsRNA.

Accordingly, in a first aspect, the invention features a method for inhibiting the expression of a target nucleic acid in a cell (e.g., an invertebrate cell, a vertebrate cell such as a mammalian or human cell, or a pathogen cell). This method involves introducing into the cell a first agent that provides to the cell a first dsRNA and introducing a second agent that provides to the cell a short, second dsRNA. The first dsRNA has substantial sequence identity to a region of the target nucleic acid and specifically inhibits the expression of the target nucleic acid. The short, second dsRNA differs from the first dsRNA and inhibits the interferon response or dsRNA-mediated toxicity. In some embodiments, the short, second dsRNA binds PKR and inhibits the dimerization and activation of PKR. Exemplary pathogens include bacteria and yeast. In some embodiments, the first dsRNA inhibits the expression of an endogenous nucleic acid in a vertebrate cell or a pathogen cell (e.g., a bacterial or yeast cell) or inhibits the expression of a pathogen nucleic acid in a cell infected with the pathogen.

In another aspect, the invention provides a method for inhibiting the expression of a target nucleic acid in an animal (e.g., an invertebrate or a vertebrate such as a mammal or human). This method involves introducing into the animal a first agent that provides to the animal a first dsRNA and introducing a second agent that provides to the animal a short, second dsRNA. The first dsRNA has substantial sequence identity to a region of the target nucleic acid and specifically inhibits the expression of the target nucleic acid. The short, second dsRNA differs from the first dsRNA and inhibits the interferon response or dsRNA-mediated toxicity. In some embodiments, the short, second dsRNA binds PKR and inhibits the dimerization and activation of PKR. In some embodiments, the first dsRNA inhibits the expression of an endogenous nucleic acid in an animal or inhibits the expression of a pathogen nucleic acid in an animal infected with a pathogen (e.g., a bacterial or yeast cell or a virus).

In yet another aspect, the invention provides a method for treating, stabilizing, or preventing a disease or disorder in an animal (e.g., an invertebrate, a vertebrate such as a mammal or human). This method involves introducing into the animal a first agent that provides to the animal a first dsRNA and a second agent that provides to the animal a short, second dsRNA. The first dsRNA has substantial sequence identity to a region of a target nucleic acid associated with the disease or disorder and specifically inhibits the expression of the target nucleic acid. The short, second dsRNA differs from the first dsRNA and inhibits the interferon response or dsRNA-mediated toxicity. In some embodiments, the short, second dsRNA binds PKR and inhibits the dimerization and activation of PKR. In some embodiments, the target gene is a gene associated with cancer, such as an oncogene, or a gene encoding a protein associated with a disease, such as a mutant protein, a dominant negative protein, or an overexpressed protein.

Exemplary cancers that can be treated, stabilized, or prevented using the above methods include prostate cancers, breast cancers, ovarian cancers, pancreatic cancers, gastric cancers, bladder cancers, salivary gland carcinomas, gastrointestinal cancers, lung cancers, colon cancers, melanomas, brain tumors, leukemias, lymphomas, and carcinomas. Benign tumors may also be treated or prevented using the methods of the present invention. Other cancers and cancer related genes that may be targeted are disclosed in, for example, WO 00/63364, WO 00/44914, and WO 99/32619.

Exemplary endogenous proteins that may be associated with disease include ANA (anti-nuclear antibody) found in SLE (systemic lupus erythematosis), abnormal immunoglobulins including IgG and IgA, Bence Jones protein associated with various multiple myelomas, and abnormal amyloid proteins in various amyloidoses including hereditary amyloidosis and Alzheimer's disease. In Huntington's Disease, a genetic abnormality in the HD (huntingtin) gene results in an expanded tract of repeated glutamine residues. In addition to this mutant gene, HD patients have a copy of chromosome 4 which has a normal sized CAG repeat. Thus, methods of the invention can be used to silence the abnormal gene but not the normal gene. In various embodiments, a nucleic acid encoding a disease-causing protein is silenced using long sRNA, and short dsRNA is used to block the dsRNA stress response that might otherwise be associated with administration of the long dsRNA.

In still another aspect, the invention features a method for treating, stabilizing, or preventing an infection in an animal (e.g., an invertebrate or a vertebrate such as a mammal or human). This method involves introducing into the animal a first agent that provides to the animal a first dsRNA and introducing a second agent that provides to the animal a short, second dsRNA. The first dsRNA has substantial sequence identity to a region of a target nucleic acid in an infectious pathogen (e.g., a virus, bacteria, or yeast) or cell infected with a pathogen and specifically inhibits the expression of the target nucleic acid. The short, second dsRNA differs from the first dsRNA and inhibits the interferon response or dsRNA-mediated toxicity. In some embodiments, the short, second dsRNA binds PKR and inhibits the dimerization and activation of PKR. In various embodiments, the pathogen is an intracellular or extracellular pathogen. In some embodiments, the target nucleic acid is a gene of the pathogen that is necessary for replication and/or pathogenesis.

In a further embodiment of any of the above aspects, the methods of administering a dsRNA or a nucleic acid encoding a dsRNA includes contacting an in-dwelling device with the cell prior to, concurrent with, or following the administration of the in-dwelling device to a patient. In-dwelling devices include, but are not limited to, surgical implants, prosthetic devices, and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, and continuous ambulatory peritoneal dialysis (CAPD) catheters. Desirably, the dsRNA prevents the growth of bacteria on the device. In some embodiments, the first dsRNA inhibits the expression of a bacterial nucleic acid in a bacterial cell, a cell infected with a bacteria, or an animal infected with a bacteria.

In other desirable embodiments, the bacterial infection is due to one or more of the following bacteria: *Chlamydophila pneumoniae, C. psittaci, C. abortus, Chlamydia trachomatis, Simkania negevensis, Parachlamydia acanthainoebae, Pseudomonas aeruginosa, P. alcaligenes, P. chlororaphis, P. fluorescens, P. luteola, P. mendocina, P. monteilii, P. oryzihabitans, P. pertocinogena, P. pseudalcaligenes, P. putida, P. stutzeri, Burkholderia cepacia, Aeromonas hydrophilia, Escherichia coli, Citrobacter freundii, Salmonella typhimurium, S. typhi, S. paratyphi, S. enteritidis, Shigella dysenteriae, S. flexneri, S. sonnei, Enterobacter cloacae, E. aerogenes, Klebsiella pneumoniae, K. oxytoca, Serratia marcescens, Francisella tularensis, Morganella morganii, Proteus mirabilis, Proteus vulgaris, Providencia alcalifaciens, P. rettgeri, P. stuartii, Acinetobacter calcoaceticus, A. haemolyticus, Yersinia enterocolitica, Y. pestis, Y. pseudotuberculosis, Y. intermedia, Bordetella pertussis, B. parapertussis, B. bronchiseptica, Haemophilus influenzae, H. parainfluenzae, H. haemolyticus, H. parahaemolyticus, H. ducreyi, Pasteurella multocida, P. haemolytica, Branhamella catarrhalis, Helicobacter pylori, Campylobacter fetus, C. jejuni, C. coli, Borrelia burgdorferi, V. cholerae, V. parahaemolyticus, Legionella pneumophila, Listeria monocytogenes, Neisseria gonorrhea, N. meningitidis, Kingella dentrificans, K. kingae, K. oralis, Moraxella catarrhalis, M. atlantae, M. lacunata, M. nonliquefaciens, M. osloensis, M. phenylpyruvica, Gardnerella vaginalis, Bacteroides fragilis, Bacteroides distasonis, Bacteroides* 3452A homology group, *Bacteroides vulgatus, B. ovalus, B. thetaiotaomicron, B. uniformis, B. eggerthii, B. splanchnicus, Clostridium difficile, Mycobacterium tuberculosis, M. avium, M. intracellulare, M. leprae, C. diphtheriae, C. ulcerans, C. accolens, C. afermentans, C. amycolatum, C. argentorense, C. auris, C. bovis, C. confusum, C. coyleae, C. durum, C. falsenii, C. glucuronolyticum, C. imitans, C. jeikeium, C. kutscheri, C. kroppenstedtii, C. lipophilum, C. macginleyi, C. matruchoti, C. mucifaciens, C. pilosum, C. propinquum, C. renale, C. riegelii, C. sanguinis, C. singulare, C. striatum, C. sundsvallense, C. thomssenii, C. urealyticum, C. xerosis, Streptococcus pneumoniae, S. agalactiae, S. pyogenes, Enterococcus avium, E. casseliflavus, E. cecorum, E. dispar, E. durans, E. faecalis, E. faecium, E. flavescens, E. gallinarum, E. hirae, E. malodoratus, E. mundtii, E. pseudoavium, E. raffinosus, E. solitarius, Staphylococcus aureus, S. epidermidis, S. saprophyticus, S. intermedius, S. hyicus, S. haemolyticus, S. hominis,* and/or *S. saccharolyticus.* Preferably, a dsRNA is administered in an amount sufficient to prevent, stabilize, or inhibit the growth of a pathogen or to kill the pathogen. In some embodiments, the first dsRNA inhibits the expression of a yeast nucleic acid in a yeast cell, a cell infected with yeast, or an animal infected with yeast.

In desirable embodiments, the viral infection relevant to the methods of the invention is an infection by one or more of the following viruses: Hepatitis B, Hepatitis C, picornarirus, polio, HIV, coxsacchie, herpes simplex virus Type I and 2, St. Louis encephalitis, Epstein-Barr, myxoviruses, JC, coxsakieviruses B, togaviruses, measles, paramyxoviruses, echoviruses, bunyaviruses, cytomegaloviruses, varicella-zoster, mumps, equine encephalitis, lymphocytic choriomeningitis, rhabodoviruses including rabies, simian virus 40, human polyoma virus, parvoviruses, papilloma viruses, primate adenoviruses, coronaviruses, retroviruses, Dengue, yellow fever, Japanese encephalitis virus and/or BK. In some embodiments, the first dsRNA inhibits the expression of a viral nucleic acid in a virus, a cell infected with a virus, or an animal infected with a virus.

In another aspect, the invention features method for reducing or preventing an immune response to a transplant cell, tissue, or organ. The method involves administering to the transplant cell, tissue, or organ a first agent that provides a first dsRNA and a second agent that provides short, second dsRNA. The first dsRNA attenuates the expression of a target nucleic acid in the transplant cell, tissue, or organ that can elicit an immune response in a recipient. The short, second dsRNA differs from the first dsRNA and inhibits the interferon response or dsRNA-mediated toxicity. In some embodiments, the short, second dsRNA binds PKR and inhibits the dimerization and activation of PKR. In some embodiments, an agent that provides a dsRNA molecule is also administered to the recipient to inhibit the expression of an endogenous nucleic acid that would otherwise participate in an adverse immune response to the transplant.

In desirable embodiments of any of the above aspects, the first dsRNA inhibits expression of the target nucleic acid by at least 20, 40, 60, 80, 90, 95, or 100%. In some embodiments, multiple first dsRNA molecules that are substantially identical to different nucleic acids are administered to the cell or animal to inhibit the expression of multiple target nucleic acids. For example, multiple oncogenes or multiple pathogen genes may be simultaneously silenced.

In various embodiments of any of the above aspects, the first agent and/or the second agent is a DNA molecule or DNA vector encoding a dsRNA. In other embodiments, the first agent and/or the second agent is a dsRNA, a single stranded RNA molecule that assumes a double stranded conformation inside the cell or animal (e.g., a hairpin), or a combination of two single stranded RNA molecules that are administered simultaneously or sequentially and that assume a double stranded conformation inside the cell or animal. The first agent may be administered before, during, or after the administration of the second agent. In some embodiments, the first and second agents are the same nucleic acid or the same vector that encodes both dsRNA molecules. In various embodiments, the first agent provides a short dsRNA or a long dsRNA to the cell or animal.

In some embodiments, a cytokine is also administered to the cell or animal. Exemplary cytokines are disclosed in WO 00/63364, filed Apr. 19, 2000. In some embodiments, the expression of the target nucleic acid is increased to promote the amplification of the dsRNA, resulting in more dsRNA to silence the target gene. For example, a vector containing the target nucleic acid can be administered to the cell or animal before, during, or after the administration of the first and/or second agent.

The invention also features high throughput methods of using dsRNA-mediated gene silencing to identify a nucleic acid that confers or modulates a detectable phenotype. A detectable phenotype may include, for example, any outward physical manifestation, such as molecules, macromolecules, structures, metabolism, energy utilization, tissues, organs, reflexes, and behaviors, as well as anything that is part of the detectable structure, function, or behavior of a cell, tissue, or living organism. Particularly useful in the methods of the invention are dsRNA mediated changes, wherein the detectable phenotype derives from modulation of the function of a cell, modulation of expression of a target nucleic acid, or modulation of the biological activity of a target polypeptide through dsRNA effects on a target nucleic acid. For example, see the dsRNA mediated methods of determining gene function in EP 1229134 A2 and WO 00/01846, the teachings of which are hereby incorporated by reference. The method involves the use of specially constructed cDNA libraries derived from a cell, for example, a primary cell or a cell line that has an observable phenotype or biological activity, (e.g., an activity mediated by a target polypeptide or altered gene expression), that are transfected into cells to inhibit gene expression. In addition, a short dsRNA or a nucleic acid (e.g., a vector) encoding a short dsRNA is administered to the cell to inhibit potential dsRNA mediated toxicity, including adverse effects due to the possible induction of the interferon response by the dsRNA expression library. The inhibition of gene expression by the present methods alters a detectable phenotype, e.g., the function of a cell, gene expression of a target nucleic acid, or the biological activity of a target polypeptide and allows the nucleic acid responsible for the modulation of the detectable phenotype to be readily identified. While less desirable, the method may also utilize randomized nucleic acid sequences or a given sequence for which the function is not known, as described, e.g., in U.S. Pat. No. 5,639,595, the teaching of which is hereby incorporated by reference.

Accordingly, in one aspect, the invention features a method for identifying a nucleic acid sequence that modulates the function of a cell. The method involves (a) transforming a population of cells with a dsRNA expression library, where at least two cells of the population of cells are each transformed with a different nucleic acid from the dsRNA expression library, and where at least one encoded dsRNA specifically inhibits the expression of a target nucleic acid in at least one cell (b) transforming the cells with a short dsRNA or a nucleic acid encoding a short dsRNA; (c) optionally selecting for a cell in which the nucleic acid is expressed in the cell; and (d) assaying for a modulation in the function of the cell, wherein a modulation identifies a nucleic acid sequence that modulates the function of a cell. The short dsRNA differs from at least one or all of the dsRNA molecules produced by the expression library that specifically inhibit the expression of a target nucleic acid in a cell or differs from all of the dsRNA molecules produced by the expression library. The short dsRNA inhibits the interferon response or dsRNA-mediated toxicity. In some embodiments, the short, dsRNA binds PKR and inhibits the dimerization and activation of PKR.

In a desirable embodiment of the above aspect of the invention, assaying for a modulation in the function of a cell comprises measuring cell motility, apoptosis, cell growth, cell invasion, vascularization, cell cycle events, cell differentiation, cell dedifferentiation, neuronal cell regeneration, or the ability of a cell to support viral replication.

In a related aspect, the invention features a method for identifying a nucleic acid sequence that modulates expression of a target nucleic acid in a cell. The method involves (a) transforming a population of cells with a dsRNA expression library, where at least two cells of the population of cells are each transformed with a different nucleic acid from the dsRNA expression library, and where at least one encoded dsRNA specifically inhibits the expression of a target nucleic acid in at least one cell (b) transforming the cells with a short dsRNA or a nucleic acid encoding a short dsRNA; (c) optionally selecting for a cell in which the nucleic acid is expressed in the cell; and (d) assaying for a modulation in the expression of a gene in the cell, where a modulation identifies a nucleic acid sequence that modulates expression of a target nucleic acid in a cell. The short dsRNA differs from at least one or all of the dsRNA molecules produced by the expression library that specifically inhibit the expression of a target nucleic acid in a cell or differs from all of the dsRNA molecules produced by the expression library. The short dsRNA inhibits the interferon response or dsRNA-mediated toxicity. In some embodiments, the short dsRNA binds PKR and inhibits the dimerization and activation of PKR. In a desirable embodiment, the target nucleic acid is assayed using DNA array technology.

In another related aspect, the invention features a method for identifying a nucleic acid sequence that modulates the biological activity of a target polypeptide in a cell. The method involves (a) transforming a population of cells with a dsRNA expression library, where at least two cells of the population of cells are each transformed with a different nucleic acid from the dsRNA expression library, and where at least one encoded dsRNA specifically inhibits the expression of a target nucleic acid in at least one cell (b) transforming the cells with a short dsRNA or a nucleic acid encoding a short dsRNA; (c) optionally selecting for a cell in which the nucleic acid is expressed in the cell; and (d) assaying for a modulation in the biological activity of a target polypeptide in the cell, wherein a modulation identifies a nucleic acid sequence that modulates the biological activity of a target polypeptide. The short dsRNA differs from at least one or all of the dsRNA molecules produced by the expression library that specifically inhibit the expression of a target nucleic acid in a cell or differs from all of the dsRNA molecules produced by the expression library. The short dsRNA inhibits the interferon response or dsRNA-mediated toxicity. In some embodiments, the short dsRNA binds PKR and inhibits the dimerization and activation of PKR.

In one embodiment of any of the above aspects of the invention, in transforming step (a), the nucleic acid is stably integrated into a chromosome of the cell. Integration of the nucleic acid may be random or site-specific. Desirably integration is mediated by recombination or retroviral insertion. In addition, desirably a single copy of the nucleic acid is integrated into the chromosome. In another embodiment of any of the above aspects of the invention, in step (a) at least 50, more desirably 100; 500; 1000; 10,000; or 50,000 cells of the population of cells are each transformed with a different nucleic acid from the dsRNA expression library. Desirably, the expression library is derived from the transfected cells or cells of the same cell type as the transfected cells. In other embodiments, the population of cells is transformed with at least 5%, more desirably at least 25%, 50%, 75%, or 90%, and most desirably at least 95% of the dsRNA expression library.

In other embodiments of any of the above aspects of the invention, the dsRNA expression library contains cDNAs or randomized nucleic acids. The dsRNA expression library may be a nuclear dsRNA expression library, in which case the double stranded nucleic acid is made in the nucleus. Alternatively, the dsRNA expression library may be a cytoplasmic dsRNA expression library, in which case the double stranded nucleic acid is made in the cytoplasm. In addition, the nucleic acid from the dsRNA expression library may be made in vitro or in vivo. In addition, the identified nucleic acid sequence may be located in the cytoplasm of the cell.

In still another embodiment of any of the above aspects of the invention, the nucleic acid is contained in a vector, for example a dsRNA expression vector. The vector may then be transformed such that it is stably integrated into a chromosome of the cell, or it may function as an episomal (non-integrated) expression vector within the cell. In one embodiment, a vector that is integrated into a chromosome of the cell contains a promoter operably linked to a nucleic acid encoding a hairpin or dsRNA. In another embodiment, the vector does not contain a promoter operably linked to a nucleic acid encoding a dsRNA. In this latter embodiment, the vector integrates into a chromosome of a cell such that an endogenous promoter is operably linked to a nucleic acid from the vector that encodes a dsRNA. Desirably, the dsRNA expression vector comprises at least one RNA polymerase II promoter, for example, a human CMV-immediate early promoter (HCMV-IE) or a simian CMV (SCMV) promoter, at least one RNA polymerase I promoter, or at least one RNA polymerase III promoter. The promoter may also be a T7 promoter, in which case, the cell further comprises T7 polymerase. Alternatively, the promoter may be an SP6 promoter, in which case, the cell further comprises SP6 polymerase. The promoter may also be one convergent T7 promoter and one convergent SP6 promoter. A cell may be made to contain T7 or SP6 polymerase by transforming the cell with a T7 polymerase or an SP6 polymerase expression plasmid, respectively. In some embodiments, a T7 promoter or a RNA polymerase III promoter is operably linked to a nucleic acid that encodes a short dsRNA (e.g., a dsRNA that is less than 200, 150, 100, 75, 50, or 25 nucleotides in length). In other embodiments, the promoter is a mitochondrial promoter that allows cytoplasmic transcription of the nucleic acid in the vector (see, for example, the mitochondrial promoters described in WO 00/63364, filed Apr. 19, 2000). Alternatively, the promoter is an inducible promoter, such as a lac (Cronin et al. *Genes & Development* 15: 1506-1517, 2001), ara (Khlebnikov et al., J Bacteriol. 2000 December; 182(24): 7029-34), ecdysone (Rheogene, www.rheogene.com), RU48 (mefepristone) (corticosteroid antagonist) (Wang X J, Liefer K M, Tsai S, O'Malley B W, Roop D R, Proc Natl Acad Sci USA. 1999 Jul. 20; 96(15):8483-8), or tet promoter (Rendal et al., Hum Gene Ther. 2002 January; 13(2):335-42, and Larnartina et al., Hum Gene Ther. 2002 January; 13(2):199-210) or a promoter disclosed in WO 00/63364, filed Apr. 19, 2000. In desirable embodiments, the inducible promoter is not induced until all the episomal vectors are eliminated from the cell. The vector may also comprise a selectable marker.

Desirably in a vector for use in any of the above aspects of the invention, the sense strand and the antisense strand of the nucleic acid sequence are transcribed from the same nucleic acid sequence using two convergent promoters. In another desirable embodiment, in a vector for use in any of the above aspects of the invention, the nucleic acid sequence comprises an inverted repeat, such that upon transcription, the nucleic acid forms a dsRNA.

In still other embodiments of any of the above aspects of the invention, the cell and the vector each further comprise a loxP site and site-specific integration of the nucleic acid into a chromosome of the cell occurs through recombination between the loxP sites. In addition, step (c) of any of the above aspects of the invention further involves rescuing the nucleic acid through Cre-mediated double recombination.

In still further embodiments of any of the above aspects of the invention, the identified nucleic acid sequence is located in the nucleus of the cell. Alternatively, the identified nucleic acid sequence may be located in the cytoplasm of the cell.

In yet another embodiment of any of the above aspects of the invention, the nucleic acid from the dsRNA expression library is at least 100, 500, 600, or 1000 nucleotides in length. In other embodiments of any of the above aspects of the invention, the nucleic acid from the dsRNA expression library is at least 10, 20, 30, 40, 50, 60, 70, 80, or 90 nucleotides in length. In yet other embodiments, the number of nucleotides in the nucleic acid from the dsRNA expression library is between 5-100 nucleotides, 15-100 nucleotides, 20-95 nucleotides, 25-90 nucleotides, 35-85 nucleotides, 45-80 nucleotides, 50-75 nucleotides, or 55-70 nucleotides, inclusive. In still other embodiments, the number of nucleotides in the nucleic acid from the dsRNA expression library is contained in one of the following ranges: 5-15 nucleotides, 15-20 nucleotides, 20-25 nucleotides, 25-35 nucleotides, 35-45 nucleotides, 45-60 nucleotides, 60-70 nucleotides, 70-80 nucleotides, 80-90 nucleotides, or 90-100 nucleotides, inclusive. In other embodiments, the nucleic acid contains less than 50,000; 10,000; 5,000; or 2,000 nucleotides. In some embodiments, the dsRNA encoded by the dsRNA expression library is 20 to 30 nucleotides (e.g., 20, 21, 22, 23, 24, 25, 26, 27, or 28 nucleotides) in length. In addition, the nucleic acid from the dsRNA expression library may contain a sequence that is less than a full length RNA sequence.

In some embodiments, the dsRNA encoded by the dsRNA expression library is 20 to 30 nucleotides (e.g., 20, 21, 22, 23, 24, 25, 26, 27, or 28 nucleotides) in length. In particular embodiments, the dsRNA encoded by the dsRNA expression library is between 11 and 40 nucleotides in length and, in the absence of short dsRNA of the invention, induces toxicity in vertebrate cells because its sequence has affinity for PKR or another protein in a dsRNA mediated stress response pathway. The short dsRNA of the invention inhibits this toxicity.

In yet another embodiment of any of the above aspects of the invention, the cell is derived from a parent cell, and is generated by (a) transforming a population of parent cells with a bicistronic plasmid expressing a selectable marker and a reporter gene, and comprising a loxP site; (b) selecting for a cell in which the plasmid is stably integrated; and (c) selecting for a cell in which one copy of the plasmid is stably integrated in a transcriptionally active locus. Desirably the selectable marker is G418 and the reporter gene is green fluorescent protein (GFP).

In still another embodiment of the above aspects of the invention, generation of the double stranded expression library comprises: (a) isolating RNA from a cell; (b) synthesizing cDNAs from the RNA of step (a); and (c) cloning each cDNA into a vector. Desirably cDNA synthesis is optimized and/or size selected for the generation and/or selection of cDNAs that are at least 100, 500, 600, or 1000 nucleotides in length. In other embodiments, the cDNAs are least 10, 20, 30, 40, 50, 60, 70, 80, or 90 nucleotides in length. In yet other embodiments, the number of nucleotides in the cDNAs is between 5-100 nucleotides, 15-100 nucleotides, 20-95 nucleotides, 25-90 nucleotides, 35-85 nucleotides, 45-80 nucleotides, 50-75 nucleotides, or 55-70 nucleotides, inclusive. In still other embodiments, the number of nucleotides in the cDNAs is contained in one of the following ranges: 5-15 nucleotides, 15-20 nucleotides, 20-25 nucleotides, 25-35 nucleotides, 35-45 nucleotides, 45-60 nucleotides, 60-70 nucleotides, 70-80 nucleotides, 80-90 nucleotides, or 90-100 nucleotides, inclusive. In other embodiments, the cDNAs contain less than 50,000; 10,000; 5,000; or 2,000 nucleotides. In addition, the cDNA may encode an RNA fragment that is less than full length. Desirably the vector comprises two convergent T7 promoters, two convergent SP6 promoters, or one convergent T7 promoter and one convergent SP6 promoter, a selectable marker, and/or a loxP site.

In addition to the above screening methods that utilize a dsRNA expression library, the invention provides screening methods that utilize (i) one or more dsRNA molecules with substantial sequence identity to a target gene to inhibit expression of the target gene and (ii) one or more short dsRNA molecules to inhibit the interferon response.

In one such aspect, the invention features a method for identifying a nucleic acid sequence that modulates the function of a cell, involving (a) transforming a population of cells with a first dsRNA and either a short, second dsRNA or a nucleic acid encoding a short, second dsRNA, (b) optionally selecting for a cell in which the nucleic acid is expressed; and (c) assaying for a modulation in the function of the cell. The first dsRNA has substantial sequence identity target nucleic acid in the cell and specifically inhibits the expression of the target nucleic acid. The short, second dsRNA differs from the first dsRNA and inhibits the interferon response or dsRNA-mediated toxicity. In some embodiments, the short, second dsRNA binds PKR and inhibits the dimerization and activation of PKR. Desirably, the modulation identifies a nucleic acid sequence that modulates the function of a cell. Desirably, the method is carried out under conditions that inhibit or prevent an interferon response dsRNA stress response. In a desirable embodiment, assaying for a modulation in the function of a cell comprises measuring cell motility, apoptosis, cell growth, cell invasion, vascularization, cell cycle events, cell differentiation, cell dedifferentiation, neuronal cell regeneration, or the ability of a cell to support viral replication.

In a related aspect, the invention features a method for identifying a nucleic acid sequence that modulates expression of a target nucleic acid in a cell, involving (a) transforming a population of cells with a first dsRNA and either a short, second dsRNA or a nucleic acid encoding a short, second dsRNA; (b) optionally selecting for a cell in which the nucleic acid is expressed; and (c) assaying for a modulation in the expression of the gene in the cell, wherein the modulation identifies a nucleic acid sequence that modulates expression of a target nucleic acid in a cell. The first dsRNA has substantial sequence identity to a target nucleic acid in a cell and specifically inhibits the expression of the target nucleic acid. The short, second dsRNA differs from the first dsRNA and inhibits the interferon response or dsRNA-mediated toxicity. In some embodiments, the short, second dsRNA binds PKR and inhibits the dimerization and activation of PKR. Desirably, the method is carried out under conditions that inhibit or prevent an interferon response or dsRNA stress response. In a desirable embodiment, the target nucleic acid is assayed using DNA array technology.

In another related aspect, the invention features a method for identifying a nucleic acid sequence that modulates the biological activity of a target polypeptide in a cell, involving (a) transforming a population of cells with a first dsRNA and either a short, second dsRNA or a nucleic acid encoding a short, second dsRNA; (b) optionally selecting for a cell in which the nucleic acid is expressed in the cell; and (c) assaying for a modulation in the biological activity of a target polypeptide in the cell, wherein the modulation identifies a nucleic acid sequence that modulates the biological activity of a target polypeptide in a cell. The first dsRNA has substantial sequence identity to a target nucleic in the cell and specifically inhibits the expression of the target nucleic acid. The short, second dsRNA differs from the first dsRNA and inhibits the interferon response or dsRNA-mediated toxicity. In some embodiments, the short, second dsRNA binds PKR and inhibits the dimerization and activation of PKR. Desirably, the method is carried out under conditions that inhibit or prevent an interferon response or dsRNA stress response.

In one embodiment of any of the above aspects of the invention, in step (a) at least 2, more desirably 50; 100; 500; 1000; 10,000; or 50,000 cells of the population of cells are each transformed with a different dsRNA. Desirably, at most one long dsRNA is inserted into each cell. In other embodiments, the population of cells is transformed with at least 5%, more desirably at least 25%, 50%, 75%, or 90%, and most desirably, at least 95% of the dsRNA expression library. In still another embodiment, the method further involves identifying the nucleic acid sequence by amplifying and cloning the sequence. Desirably amplification of the sequence involves the use of the polymerase chain reaction (PCR).

In some embodiments, the first dsRNA is 20 to 30 nucleotides (e.g., 20, 21, 22, 23, 24, 25, 26, 27, or 28 nucleotides) in length. In particular embodiments, the first dsRNA is between 11 and 40 nucleotides in length and, in the absence of short dsRNA of the invention, induces toxicity in vertebrate cells because its sequence has affinity for PKR or another protein in a dsRNA mediated stress response pathway. The short dsRNA of the invention inhibits this toxicity.

In a yet another aspect, the invention features a cell or a population of cells that expresses a dsRNA that (i) modulates a function of the cell, (ii) modulates the expression of a target nucleic acid (e.g., an endogenous or pathogen gene) in the cell, and/or (iii) modulates the biological activity of a target protein (e.g., an endogenous or pathogen protein) in the cell. The cell or population of cells also has one or more short dsRNA molecules (e.g., 1, 2, 3, 5, 8, 10, 20, 30, or more different short dsRNA species). Desirably, the cell contains only one molecular species of long dsRNA or only one copy of a dsRNA expression vector encoding a long dsRNA (e.g., a stably integrated vector). Desirably, the cell or population of cells is produced using one or more methods of the invention. In other embodiments, the dsRNA is expressed under conditions that inhibit or prevent an interferon response or a dsRNA stress response.

In still another aspect, the invention provides a pharmaceutical composition which includes at least one short dsRNA (e.g., 1, 2, 3, 5, 8, 10, 20, 30, or more different short dsRNA species) and at least one long dsRNA (e.g., 1, 2, 3, 5, 8, 10, 20, 30, or more different long dsRNA species) in an acceptable vehicle (e.g., a pharmaceutically acceptable carrier). Suitable carriers include, but are not limited to, saline, buffered saline, dextrose, water, glycerol, ethanol, and combinations thereof. The composition can be adapted for the mode of administration and can be in the form of, for example, a pill, tablet, capsule, spray, powder, or liquid. In some embodiments, the pharmaceutical composition contains one or more pharmaceutically acceptable additives suitable for the selected route and mode of administration. These compositions may be administered by, without limitation, any parenteral route including intravenous, intra-arterial, intramuscular, subcutaneous, intradermal, intraperitoneal, intrathecal, as well as topically, orally, and by mucosal routes of delivery such as intranasal, inhalation, rectal, vaginal, buccal, and sublingual. In some embodiments, the pharmaceutical compositions of the invention are prepared for administration to vertebrate (e.g., mammalian) subjects in the form of liquids, including sterile, non-pyrogenic liquids for injection, emulsions, powders, aerosols, tablets, capsules, enteric coated tablets, or suppositories.

In some embodiments, the pharmaceutical composition includes about 1 ng to about 20 mg of nucleic acids, e.g., RNA, DNA, plasmids, viral vectors, recombinant viruses, or mixtures thereof, which provide the desired amounts of the respective dsRNAs (dsRNA homologous to a target nucleic acid and dsRNA to inhibit toxicity). In some embodiments, the composition contains about 10 ng to about 10 mg of the nucleic acids, about 0.1 to about 500 mg, about 1 to about 350 mg, about 25 to about 250 mg, or about 100 mg of the nucleic acids. If desired, the dosage regimen of the short dsRNA may be adjusted to achieve the optimal inhibition of PKR and/or other dsRNA-mediated stress responses, and the dosage regimen of the other dsRNA (e.g, long dsRNA) may be adjusted to optimize the desired sequence-specific silencing. Accordingly, a composition of the invention may contain different amounts of the two dsRNA molecules. Those of skill in the art of clinical pharmacology can readily arrive at such dosing schedules using routine experimentation.

In a related aspect, the invention provides a kit which includes at least one short dsRNA (e.g., 1, 2, 3, 5, 8, 10, 20, 30 or more different short dsRNA species) in an acceptable vehicle and at least one long dsRNA (e.g., 1, 2, 3, 5, 8, 10, 20, 30, or more different long dsRNA species) in an acceptable vehicle. The kit allows the short dsRNA to be administered before, simultaneously with, or after the long dsRNA. In some embodiments, the short dsRNA is administered using a different route, delivery system, mode, site, or rate of administration that used for the long dsRNA.

In other embodiments of any of the above aspects of the invention, the short or long dsRNA is derived from cDNAs or randomized nucleic acids. In addition, the dsRNA may be a cytoplasmic dsRNA, in which case the double stranded nucleic acid is made in the cytoplasm. The dsRNA may be made in vitro or in vivo. In addition, the identified nucleic acid sequence may be located in the cytoplasm of the cell.

In still another embodiment of any of the various aspects of the invention, the nucleic acid is contained in a vector, for example, a dsRNA expression vector that is capable of forming a dsRNA. Desirably the dsRNA expression vector comprises at least one promoter. The promoter may be a T7 promoter, in which case the cell further comprises T7 polymerase. Alternatively, the promoter may be an SP6 promoter, in which case, the cell further comprises SP6 polymerase. The promoter may also be one convergent T7 promoter and one convergent SP6 promoter. A cell may be made to contain T7 or SP6 polymerase by transforming the cell with a T7 polymerase or an SP6 polymerase expression plasmid, respectively. The vector may also comprise a selectable marker, for example hygromycin.

Desirably, in a vector for use in the methods of the invention, the sense strand and the antisense strand of the nucleic acid sequence are transcribed from the same nucleic acid sequence using two convergent promoters. In another desirable embodiment, in a vector for use in any of the above aspects of the invention, the nucleic acid sequence comprises an inverted repeat, such that upon transcription, the nucleic acid forms a dsRNA.

In yet another embodiment, the dsRNA is at least 100, 500, 600, or 1000 nucleotides in length. In other embodiments, the dsRNA is at least 10, 20, 30, 40, 50, 60, 70, 80, or 90 nucleotides in length. In yet other embodiments, the number of nucleotides in the dsRNA is between 5-100 nucleotides, 15-100 nucleotides, 20-95 nucleotides, 25-90 nucleotides, 35-85 nucleotides, 45-80 nucleotides, 50-75 nucleotides, or 55-70 nucleotides, inclusive. In still other embodiments, the number of nucleotides in the dsRNA is contained in one of the following ranges: 5-15 nucleotides, 15-20 nucleotides, 20-25 nucleotides, 25-35 nucleotides, 35-45 nucleotides, 45-60 nucleotides, 60-70 nucleotides, 70-80 nucleotides, 80-90 nucleotides, or 90-100 nucleotides, inclusive. In other embodiments, the dsRNA contains less than 50,000; 10,000; 5,000; or 2,000 nucleotides. In addition, the dsRNA may contain a sequence that is less than a full length RNA sequence. In other desirable embodiments, the double stranded region in the dsRNA (e.g., a long dsRNA) contains between 11 and 30 nucleotides, inclusive; over 30 nucleotides; or over 200 nucleotides. In desirable embodiments, the double stranded region in the short dsRNA contains between 11 and 30 nucleotides, inclusive.

In still further embodiments of any aspect of the invention, the cell is a plant cell or an animal cell. Desirably the animal cell is an invertebrate, vertebrate, or mammalian cell, for example, a human cell. The cell may be ex vivo or in vivo. The cell may be a gamete or a somatic cell, for example, a cancer cell, a stem cell, a cell of the immune system, a neuronal cell, a muscle cell, or an adipocyte.

In other embodiments, the dsRNA is derived from a cell or a population of cells and used to transform another cell population of either the same cell type or a different cell type. In desirable embodiments, the transformed cell population contains cells of a cell type that is related to the cell type of the cells from which the dsRNA was derived (e.g., the transformation of cells of one neuronal cell type with the dsRNA derived from cells of another neuronal cell type). In yet other embodiments of any of these aspects, the dsRNA contains one or more contiguous or non-contiguous positions that are randomized (e.g., by chemical or enzymatic synthesis using a mixture of nucleotides that may be added at the randomized position). In still other embodiments, the dsRNA is a randomized nucleic acid in which segments of ribonucleotides and/or deoxyribonucleotides are ligated to form the dsRNA.

In other embodiments of any of various aspects of the invention, the dsRNA (e.g., a long dsRNA) specifically hybridizes to a target nucleic acid but does not substantially hybridize to non-target molecules, which include other nucleic acids in the cell or biological sample having a sequence that is less than 99, 95, 90, 80, or 70% identical or complementary to that of the target nucleic acid. Desirably, the amount of the these non-target molecules hybridized to, or associated with, the dsRNA, as measured using standard assays, is 2-fold, desirably 5-fold, more desirably 10-fold, and most desirably 50-fold lower than the amount of the target nucleic acid hybridized to, or associated with, the dsRNA. In other embodiments, the amount of a target nucleic acid hybridized to, or associated with, the dsRNA, as measured using standard assays, is 2-fold, desirably 5-fold, more desirably 10-fold, and most desirably 50-fold greater than the amount of a control nucleic acid hybridized to, or associated with, the dsRNA. Desirably, the dsRNA only hybridizes to one target nucleic acid from a cell under denaturing, high stringency hybridization conditions. In certain embodiments, the dsRNA is substantially homologous (e.g., at least 80, 90, 95, 98, or 100% homologous) to only one target nucleic acid from a cell. In other embodiments, the dsRNA is homologous to multiple RNA molecules, such as RNA molecules from the same gene family. In yet other embodiments, the dsRNA is homologous to distinctly different mRNA sequences from genes that are similarly regulated (e.g., developmental, chromatin remodeling, or stress response induced). In other embodiments, the dsRNA is homologous to a large number of RNA molecules, such as a dsRNA designed to induce a stress response or apoptosis. In other embodiments, the percent decrease in the expression of a target nucleic acid is at least 2, 5, 10, 20, or 50 fold greater than the percent decrease in the expression of a non-target or control nucleic acid. Desirably, the dsRNA inhibits the expression of a target nucleic acid but has negligible, if any, effect on the expression of other nucleic acids in the cell. Examples of control nucleic acids include nucleic acids with a random sequence or nucleic acids known to have little, if any, affinity for the dsRNA.

Desirably, the long and short dsRNA molecules are substantially non-homologous to a naturally-occurring essential mammalian gene or to all the essential mammalian genes (see, for example, WO 00/63364). In some embodiments, the dsRNA does not adversely affect the function of an essential gene. In other embodiments, the dsRNA adversely affects the function of an essential gene in a cancer cell. Desirably, the short dsRNA inhibits the dimerization of PKR or another protein in a dsRNA-mediated stress response pathway by at least 10, 20, 30, 40, 50, 60, 70, 80, 90, or 95% compared to amount of dimerization of the protein in a control cell or animal not administered the short dsRNA, as measured using standard methods such as those described herein.

In some embodiments, the short dsRNA includes a region of randomized sequence, or the entire short dsRNA contains randomized sequence. In various embodiments, the short dsRNA does not substantially decrease the expression of a nucleic acid in the cell (e.g., decreases expression by less than 60, 40, 30, 20, or 10%). In certain embodiments, the sequence of the short dsRNA is less than 80, 70, 60, 50, 30, 20, or 10% identical to or complementary to that of a nucleic acid in the cell. In particular embodiments, multiple short dsRNA molecules or multiple vectors encoding short dsRNA are administered to the cell and less than 70, 60, 50, 30, 20, or 10% of the short dsRNA molecules have a sequence that is at least 50, 70, 80, or 90% identical to or complementary to that of a nucleic acid in the cell.

In some embodiments, a target gene (e.g., a pathogen or endogenous target gene) or a region from a target gene (e.g., a region from an intron, exon, untranslated region, promoter, or coding region) is introduced into the cell or animal. For example, this target nucleic acid can be inserted into a vector that desirably integrates in the genome of a cell and then administered to the cell or animal. Desirably, the administration of one or more copies of the target nucleic acid enhances the amplification of the dsRNA that is homologous to the target nucleic acid or enhances the amplification of cleavage products from this dsRNA.

In other embodiments of any of various aspects of the invention, at most one molecular species of long dsRNA is inserted into each cell. In other embodiments, at most one vector encoding a long dsRNA is stably integrated into the genome of each cell. In various embodiments, the dsRNA is active in the nucleus of the transformed cell and/or is active in the cytoplasm of the transformed cell. In various embodiments, at least 1, 10, 20, 50, 100, 500, or 1000 cells or all of the cells in the population are selected as cells that contain or express a dsRNA (e.g., a long dsRNA). In some embodiments, at least 1, 10, 20, 50, 100, 500, or 1000 cells or all of the cells in the population are assayed for a modulation in the function of the cell, a modulation in the expression of a target nucleic acid (e.g., an endogenous or pathogen gene) in the cell, and/or a modulation in the biological activity of a target protein (e.g., an endogenous or pathogen protein) in the cell.

In other embodiments, the dsRNA or dsRNA expression vector is complexed with one or more cationic lipids or cationic amphiphiles, such as the compositions disclosed in U.S. Pat. No. 4,897,355 (Eppstein et al., filed Oct. 29, 1987), U.S. Pat. No. 5,264,618 (Felgner et al., filed Apr. 16, 1991) or U.S. Pat. No. 5,459,127 (Felgner et al., filed Sep. 16, 1993). In other embodiments, the dsRNA or dsRNA expression vector is complexed with a liposomes/liposomic composition that includes a cationic lipid and optionally includes another component such as a neutral lipid (see, for example, U.S. Pat. No. 5,279,833 (Rose), U.S. Pat. No. 5,283,185 (Epand), and U.S. Pat. No. 5,932,241). In yet other embodiments, the dsRNA or dsRNA expression vector is complexed with any other composition that is devised by one of ordinary skill in the fields of pharmaceutics and molecular biology.

Transformation/transfection of the cell may occur through a variety of means including, but not limited to, lipofection, DEAE-dextran-mediated transfection, microinjection, protoplast fusion, calcium phosphate precipitation, viral or retroviral delivery, electroporation, or biolistic transformation. The RNA or RNA expression vector (DNA) may be naked RNA or DNA or local anesthetic complexed RNA or DNA (Pachuk et al., supra). In yet another embodiment, the cell is not a *C. elegans* cell. Desirably the vertebrate (e.g., mammalian) cell has been cultured for only a small number of passages (e.g., less than 30 passages of a cell line that has been directly obtained from American Type Culture Collection), or are primary cells. In addition, desirably the vertebrate (e.g., mammalian) cell is transformed with dsRNA that is not complexed with cationic lipids.

The present methods provide numerous advantages for the silencing of genes in cells and animals. For example, in other dsRNA delivery systems some dsRNA molecules induce an interferon response (Jaramillo et al., Cancer Invest. 13:327-338, 1995). During the induction of post-transcriptional gene silencing events, induction of an interferon response is not desired, as this could lead to cell death and possibly to the prevention of gene silencing. Thus, a significant advantage of the present invention is that the dsRNA delivery methods described herein are performed such that an interferon response is inhibited or prevented. These methods allow dsRNA to be used in clinical applications for the prevention or treatment of disease or infection without the generation of adverse side-effects due to dsRNA-induced toxicity. The use of both short and long dsRNA molecules in some embodiments of the present methods may also have improved efficiency for silencing genes than previous methods that use only short dsRNA molecules.

The methods of the present invention also provide a means for high throughput identification of nucleic acid sequences involved in modulating the function of a cell, the expression of a target nucleic acid in a cell, or the biological activity of a target polypeptide in a cell. By transforming a population of cells with a dsRNA expression library or a dsRNA library, the effects of many PTGS events on cell function, expression of a target nucleic acid in a cell, or the biological activity of a target polypeptide in a cell can be evaluated simultaneously, thereby allowing for rapid identification of the nucleic acid sequence involved in a cell function, target nucleic acid expression, or biological activity of a target polypeptide of interest. Again, the administration of a short dsRNA or a nucleic acid encoding a short dsRNA prevents toxic side-effects that might otherwise complicate the analysis of gene silencing in the cells or even kill the cells.

The transcription systems described herein also provide advantages to other double stranded expression systems. Following transformation of the dsRNA library, cells contain hundreds to thousands of dsRNA expression cassettes, with concomitant expression of that many expression cassettes. In the dsRNA expression system of the present invention, dsRNA expression cassettes contained within the expression vector integrate into the chromosome of the transfected cell. Desirably, every transformed cell integrates one of the double stranded expression cassettes. Through expansion of the transformed cell, episomal (non-integrated) expression vectors are desirably diluted out of the cell over time. Desirably no transcription occurs until the episomal expression vectors are diluted out of the cell, such that not more than 5 episomal vectors remain in the cell. Most desirably, no transcription occurs until all of the episomal vectors have been diluted out of the cell, and only the integrated expression cassette remains. The time it takes for all episomal vectors to be removed from the cell is proportional to the replication rate of the transformed cell, and is generally on the order of two to several weeks of cell culture and growth. The numbers of copies of a dsRNA molecule in a transformed cell can be determined using, for example, standard PCR techniques, and thereby, the number of episomal vectors in a given cell can be monitored.

In some embodiments, once a stable integrant containing five or fewer, and desirably no episomal expression vectors, transcription is induced, allowing dsRNA to be expressed in the cells. This method ensures that, if desired, only one species or not more than about five species of dsRNA is expressed per cell, as opposed to other methods that express hundreds to thousands of double stranded species.

By "isolated nucleic acid, nucleic acid sequence, dsRNA nucleic acid sequence, or dsRNA nucleic acid" is meant a nucleic acid or a portion thereof that is free of the genes that, in the naturally-occurring genome of the organism from which the nucleic acid sequence of the invention is derived, flank the gene. The term therefore includes, for example, a recombinant DNA, with or without 5' or 3' flanking sequences that is incorporated into a vector, for example, a dsRNA expression vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences.

By "double stranded RNA" is meant a nucleic acid containing a region of two or more nucleotides that are in a double stranded conformation. In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000 or U.S. Ser. No. 60/130,377, filed Apr. 21, 1999. The dsRNA may be a single molecule with a region of self-complementarity such that nucleotides in one segment of the molecule base pair with nucleotides in another segment of the molecule. In various embodiments, a dsRNA that consists of a single molecule consists entirely of ribonucleotides or includes a region of ribonucleotides that is complimentary to a region of deoxyribonucleotides. Alternatively, the dsRNA may include two different strands that have a region of complementarity to each other. In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. Desirably, the regions of complementarity are at least 70, 80, 90, 95, 98, or 100% complimentary. Desirably, the region of the dsRNA that is present in a double stranded conformation includes at least 5, 10, 20, 30, 50, 75, 100, 200, 500, 1000, 2000 or 5000 nucleotides or includes all of the nucleotides in a cDNA being represented in the dsRNA. In some embodiments, the dsRNA does not contain any single stranded regions, such as single stranded ends, or the dsRNA is a hairpin. In other embodiments, the dsRNA has one or more single stranded regions or overhangs. Desirable RNA/DNA hybrids include a DNA strand or region that is an antisense strand or region (e.g, has at least 70, 80, 90, 95, 98, or 100% complimentary to a target nucleic acid) and an RNA strand or region that is an sense strand or region (e.g, has at least 70, 80, 90, 95, 98, or 100% identity to a target nucleic acid). In various embodiments, the RNA/DNA hybrid is made in vitro using enzymatic or chemical synthetic methods such as those described herein or those described in WO 00/63364, filed Apr. 19, 2000 or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell.

In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000 or U.S. Ser. No. 60/130, 377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as flourine group) or contains an alkoxy group (such as a methoxy group) which increases the half-life of the dsRNA in vitro or in vivo compared to the corresponding dsRNA in which the corresponding 2' position contains a hydrogen or an hydroxyl group. In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. In other embodiments, the dsRNA contains one or two capped strands or no capped strands, as disclosed, for example, by WO 00/63364, filed Apr. 19, 2000 or U.S. Ser. No. 60/130,377, filed Apr. 21, 1999. In other embodiments, the dsRNA contains coding sequence or non-coding sequence, for example, a regulatory sequence (e.g., a transcription factor binding site, a promoter, or a 5' or 3' untranslated region (UTR) of an mRNA). Additionally, the dsRNA can be any of the at least partially double-stranded RNA molecules disclosed in WO 00/63364, filed Apr. 19, 2000 (see, for example, pages 8-22). Any of the dsRNA molecules may be expressed in vitro or in vivo using the methods described herein or standard methods, such as those described in WO 00/63364, filed Apr. 19, 2000 (see, for example, pages 16-22).

By "short dsRNA" is meant a dsRNA that has 45, 40, 35, 30, 27, 25, 23, 21, 18, 15, 13, or fewer contiguous nucleotides in length that are in a double stranded conformation. Desirably, the short dsRNA is at least 11 nucleotides in length. In desirable embodiments, the double stranded region is between 11 to 45, 11 to 40, 11 to 30, 11 to 20, 15 to 20, 15 to 18, 20 to 25, 21 to 23, 25 to 30, or 30 to 40 contiguous nucleotides in length, inclusive. In some embodiments, the short dsRNA is between 30 to 50, 50 to 100, 100 to 200, 200 to 300, 400 to 500, 500 to 700, 700 to 1000, 1000 to 2000, or 2000 to 5000 nucleotides in length, inclusive and has a double stranded region that is between 11 and 40 contiguous nucleotides in length, inclusive. In one embodiment, the short dsRNA is completely double stranded. In some embodiments, the short dsRNA is between 11 and 30 nucleotides in length, and the entire dsRNA is double stranded. In other embodiments, the short dsRNA has one or two single stranded regions. In particular embodiments, the short dsRNA binds PKR or another protein in a dsRNA-mediated stress response pathway. Desirably, the short dsRNA inhibits the dimerization and activation of PKR by at least 20, 40, 60, 80, 90, or 100%. In some desirable embodiments, the short dsRNA inhibits the binding of a long dsRNA to PKR or another component of a dsRNA-mediated stress response pathway by at least 20, 40, 60, 80, 90, or 100%.

By "long dsRNA" is meant a dsRNA that is at least 40, 50, 100, 200, 500, 1000, 2000, 50000, 10000, or more nucleotides in length. In some embodiments, the long dsRNA has a double stranded region of between 100 to 10000, 100 to 1000, 200 to 1000, or 200 to 500 contiguous nucleotides, inclusive. In some embodiments, the long dsRNA is a single strand which achieves a double-stranded structure by virtue of regions of self-complementarity (e.g., inverted repeats or tandem sense and antisense sequences) that result in the formation of a hairpin structure. In one embodiment, the long dsRNA molecule does not produce a functional protein or is not translated. For example, the long dsRNA may be designed not to interact with cellular factors involved in translation. Exemplary long dsRNA molecules lack a poly-adenylation sequence, a Kozak region necessary for protein translation, an initiating methionine codon, and/or a cap structure. In other embodiments, the dsRNA molecule has a cap structure, one or more introns, and/or a polyadenylation sequence. Other such long dsRNA molecules include RNA/DNA hybrids. Other dsRNA molecules that may be used in the methods of the invention and various means for their preparation and delivery are described in WO 00/63364, filed Apr. 19, 2000, the teaching of which is incorporated herein by reference.

By "dsRNA expression library" or "dsRNA expression library" is meant a collection of nucleic acid expression vectors containing nucleic acid sequences, for example, cDNA sequences or randomized nucleic acid sequences that are capable of forming a dsRNA (dsRNA) upon expression of the nucleic acid sequence. Desirably the dsRNA expression library contains at least 10,000 unique nucleic acid sequences, more desirably at least 50,000; 100,000; or 500,000 unique nucleic acid sequences, and most desirably, at least 1,000,000 unique nucleic acid sequences. By a "unique nucleic acid sequence" is meant that a nucleic acid sequence of a dsRNA expression library has desirably less than 50%, more desirably less than 25% or 20%, and most desirably less than 10% nucleic acid identity to another nucleic acid sequence of a dsRNA expression library when the full length sequence are compared. Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications.

The preparation of cDNAs for the generation of dsRNA expression libraries is described herein. A randomized nucleic acid library may also be generated as described in detail below. The dsRNA expression library may contain nucleic acid sequences that are transcribed in the nucleus or that are transcribed in the cytoplasm of the cell. A dsRNA expression library may be generated using techniques described herein.

By "agent that provides an at least partially doubled stranded RNA" is meant a composition that generates an at least partially double stranded dsRNA in a cell or animal. For example, the agent can be a dsRNA, a single stranded RNA molecule that assumes a double stranded conformation inside the cell or animal (e.g., a hairpin), or a combination of two single stranded RNA molecules that are administered simultaneously or sequentially and that assume a double stranded conformation inside the cell or animal. Other exemplary agents include a DNA molecule, plasmid, viral vector, or recombinant virus encoding an at least partially double stranded RNA. Other agents are disclosed in WO 00/63364, filed Apr. 19, 2000. In some embodiments, the agent includes between 1 ng and 20 mg, 1 ng to 1 ug, 1 ug to 1 mg, or 1 mg to 20 mg of DNA and/or RNA.

By "target nucleic acid" is meant a nucleic acid sequence whose expression is modulated as a result of post-transcriptional gene silencing. As used herein, the target nucleic acid may be in the cell in which the PTGS, transcriptional gene silencing (TGS), or other gene silencing event occurs or it may be in a neighboring cell, or in a cell contacted with media or other extracellular fluid in which the cell that has undergone the PTGS, TGS, or other gene silencing event is contained. Exemplary target nucleic acids include nucleic acids associated with cancer or abnormal cell growth, such as oncogenes, and nucleic acids associated with an autosomal dominant or recessive disorder (see, for example, WO 00/63364, WO 00/44914, and WO 99/32619).

Desirably, the dsRNA inhibits the expression of an allele of a nucleic acid that has a mutation associated with a dominant disorder and does not substantially inhibit the other allele of the nucleic acid (e.g, an allele without a mutation associated with the disorder). Other exemplary target nucleic acids include host cellular nucleic acids or pathogen nucleic acids required for the infection or propagation of a pathogen, such as a virus, bacteria, yeast, protozoa, or parasite.

By "target polypeptide" is meant a polypeptide whose biological activity is modulated as a result of gene silencing. As used herein, the target polypeptide may be in the cell in which the PTGS, TGS, or other gene silencing event occurs or it may be in a neighboring cell, or in a cell contacted with media or other extracellular fluid in which the cell that has undergone the PTGS, TGS, or other gene silencing event is contained.

By "treating, stabilizing, or preventing a disease or disorder" is meant preventing or delaying an initial or subsequent occurrence of a disease or disorder; increasing the disease-free survival time between the disappearance of a condition and its reoccurrence; stabilizing or reducing an adverse symptom associated with a condition; or inhibiting or stabilizing the progression of a condition. Preferably, at least 20, 40, 60, 80, 90, or 95% of the treated subjects have a complete remission in which all evidence of the disease disappears. In another embodiment, the length of time a patient survives after being diagnosed with a condition and treated using a method of the invention is at least 20, 40, 60, 80, 100, 200, or even 500% greater than (i) the average amount of time an untreated patient survives or (ii) the average amount of time a patient treated with another therapy survives.

By "treating, stabilizing, or preventing cancer" is meant causing a reduction in the size of a tumor, slowing or preventing an increase in the size of a tumor, increasing the disease-free survival time between the disappearance of a tumor and its reappearance, preventing an initial or subsequent occurrence of a tumor, or reducing or stabilizing an adverse symptom associated with a tumor. In one embodiment, the percent of cancerous cells surviving the treatment is at least 20, 40, 60, 80, or 100% lower than the initial number of cancerous cells, as measured using any standard assay. Preferably, the decrease in the number of cancerous cells induced by administration of a composition of the invention is at least 2, 5, 10, 20, or 50-fold greater than the decrease in the number of non-cancerous cells. In yet another embodiment, the number of cancerous cells present after administration of a composition of the invention is at least 2, 5, 10, 20, or 50-fold lower than the number of cancerous cells present after administration of a vehicle control. Preferably, the methods of the present invention result in a decrease of 20, 40, 60, 80, or 100% in the size of a tumor as determined using standard methods. Preferably, at least 20, 40, 60, 80, 90, or 95% of the treated subjects have a complete remission in which all evidence of the cancer disappears. Preferably, the cancer does not reappear or reappears after at least 5, 10, 15, or 20 years. In another desirable embodiment, the length of time a patient survives after being diagnosed with cancer and treated with a composition of the invention is at least 20, 40, 60, 80, 100, 200, or even 500% greater than (i) the average amount of time an untreated patient survives or (ii) the average amount of time a patient treated with another therapy survives.

By "bacterial infection" is meant the invasion of a host animal by pathogenic bacteria. For example, the infection may include the excessive growth of bacteria that are normally present in or on the body of a animal or growth of bacteria that are not normally present on the animal. More generally, a bacterial infection can be any situation in which the presence of a bacterial population(s) is damaging to a host animal. Thus, a animal is "suffering" from a bacterial infection when an excessive amount of a bacterial population is present in or on the animal's body, or when the presence of a bacterial population(s) is damaging the cells or other tissue of the animal. In one embodiment, the number of a particular genus or species of bacteria is at least 2, 4, 6, or 8 times the number normally found in the animal. The bacterial infection may be due to gram positive and/or gram negative bacteria.

By "viral infection" is meant the invasion of a host animal by a virus. For example, the infection may include the excessive growth of viruses that are normally present in or on the body of a animal or growth of viruses that are not normally present in or on the animal. More generally, a viral infection can be any situation in which the presence of a viral population(s) is damaging to a host animal. Thus, a animal is "suffering" from a viral infection when an excessive amount of a viral population is present in or on the animal's body, or when the presence of a viral population(s) is damaging the cells or other tissue of the animal.

As used herein, by "randomized nucleic acids" is meant nucleic acids, for example, those that are at least 100, 500, 600, or 1000 nucleotides in length, constructed from RNA isolated from a particular cell type. In other embodiments, the nucleic acids are at least 10, 20, 30, 40, 50, 60, 70, 80, or 90 nucleotides in length. In yet other embodiments, the number of nucleotides in the nucleic acids is between 5-100 nucleotides, 15-100 nucleotides, 20-95 nucleotides, 25-90 nucleotides, 35-85 nucleotides, 45-80 nucleotides, 50-75 nucleotides, or 55-70 nucleotides, inclusive. In still other embodiments, the number of nucleotides in the nucleic acids is contained in one of the following ranges: 5-15 nucleotides, 15-20 nucleotides, 20-25 nucleotides, 25-35 nucleotides, 35-45 nucleotides, 45-60 nucleotides, 60-70 nucleotides, 70-80 nucleotides, 80-90 nucleotides, or 90-100 nucleotides, inclusive. In other embodiments, the nucleic acids contain less than 50,000; 10,000; 5,000; or 2,000 nucleotides. A randomized nucleic acid library may be constructed in a number of ways. For example, it may be constructed from existing cDNA libraries. In one example, the cDNA libraries are shuffled using the "Gene Shuffling" technology of Maxygen Corp. The cDNA sequences are amplified using inefficient PCR either by restricting elongation time or through the use of manganese. A library of recombinants is created, and the library is finally amplified by PCR and cloned into vectors. In a second method, existing cDNA libraries are digested with an endonuclease to generate fragments of 10 to 300 base pairs. Alternatively, the cDNA libraries are digested to generate shorter fragments of, for example, 5 to 50 base pairs, 5 to 40 base pairs, 5 to 20 base pairs, 5 to 10 base pairs, or 10 to 20 base pairs, inclusive. If the fragments are to contain 5' OH and 3' $PO_4$ groups, they are dephosphorylated using alkaline phosphatase and phosphorylated using polynucleotide kinase. These dsDNA fragments are then ligated to form larger molecules, and are size selected. In a third example, randomized nucleic acid libraries are created by using random priming of cDNA libraries (using random hexamers and Klenow) to generate short fragments of 20 to 100 nucleotides. Alternatively, shorter fragments are generated that contain, for example, 5 to 50 nucleotides, 5 to 40 nucleotides, 5 to 20 nucleotides, 5 to 10 nucleotides, or 10 to 20 nucleotides, inclusive. These fragments are then ligated randomly to give a desired sized larger fragment.

Alternatively, a randomized nucleic acid library can be generated from random sequences of oligonucleotides. For example, DNA or RNA oligonucleotides may be prepared chemically. Random DNA sequences may also be prepared enzymatically using terminal transferase in the presence of all dNTPs. Random RNA molecules may be prepared using NDPs and NDP phosphorylase. The random sequences may be 10 to 300 bases in length. Alternatively, shorter random sequences are used that contain, for example, 5 to 50 bases, 5 to 40 bases, 5 to 20 bases, 5 to 10 bases, or 10 to 20 bases, inclusive. The sequences are ligated to form the desired larger sequence using RNA ligase. Alternatively these sequences may be ligated chemically. The oligonucleotides are phosphorylated at the 5' position using polynucleotide kinase or by chemical methods, prior to ligation enzymatically. Chemical ligations can utilize a 5' $PO_4$ and a 3' OH group or a 5' OH and a 3' $PO_4$ group.

Alternatively, a randomized nucleic acid library can be generated by converting the random DNA sequences into dsDNA sequences using DNA polymerase (Klenow), dNTP and random heteromeric primers, and the RNA sequences are converted into dsDNA sequences by reverse transcriptase and Klenow. After converting into ssDNA or dsDNA the sequences are then amplified by PCR. The dsDNA fragments can also be ligated to give larger fragments of a desired size.

The randomized nucleic acids may be cloned into a vector, for example, an expression vector, as a dsRNA transcription cassette. The sequence of the nucleic acid may not be known at the time the vector is generated. The randomized nucleic acid may contain coding sequence or non-coding sequence, for example, a regulatory sequence (e.g., a transcription factor binding site, a promoter, or a 5' or 3' untranslated region (UTR) of an mRNA).

By "Cre-mediated double recombination" is meant two nucleic acid recombination events involving loxP sites that are mediated by Cre recombinase. A Cre-mediated double recombination event can occur, for example, as illustrated in FIG. 1.

By "function of a cell" is meant any cell activity that can be measured or assessed. Examples of cell function include, but are not limited to, cell motility, apoptosis, cell growth, cell invasion, vascularization, cell cycle events, cell differentiation, cell dedifferentiation, neuronal cell regeneration, and the ability of a cell to support viral replication. The function of a cell may also be to affect the function, gene expression, or the polypeptide biological activity of another cell, for example, a neighboring cell, a cell that is contacted with the cell, or a cell that is contacted with media or other extracellular fluid that the cell is contained in.

By "apoptosis" is meant a cell death pathway wherein a dying cell displays a set of well-characterized biochemical hallmarks that include cytolemmal membrane blebbing, cell soma shrinkage, chromatin condensation, nuclear disintegration, and DNA laddering. There are many well-known assays for determining the apoptotic state of a cell, including, and not limited to: reduction of MTT tetrazolium dye, TUNEL staining, Annexin V staining, propidium iodide staining, DNA laddering, PARP cleavage, caspase activation, and assessment of cellular and nuclear morphology. Any of these or other known assays may be used in the methods of the invention to determine whether a cell is undergoing apoptosis.

By "polypeptide biological activity" is meant the ability of a target polypeptide to modulate cell function. The level of polypeptide biological activity may be directly measured using standard assays known in the art. For example, the relative level of polypeptide biological activity may be assessed by measuring the level of the mRNA that encodes the target polypeptide (e.g., by reverse transcription-polymerase chain reaction (RT-PCR) amplification or Northern blot analysis); the level of target polypeptide (e.g., by ELISA or Western blot analysis); the activity of a reporter gene under the transcriptional regulation of a target polypeptide transcriptional regulatory region (e.g., by reporter gene assay, as described below); the specific interaction of a target polypeptide with another molecule, for example, a polypeptide that is activated by the target polypeptide or that inhibits the target polypeptide activity (e.g., by the two-hybrid assay); or the phosphorylation or glycosylation state of the target polypeptide. A compound, such as a dsRNA, that increases the level of the target polypeptide, mRNA encoding the target polypeptide, or reporter gene activity within a cell, a cell extract, or other experimental sample is a compound that stimulates or increases the biological activity of a target polypeptide. A compound, such as a dsRNA, that decreases the level of the target polypeptide, mRNA encoding the target polypeptide, or reporter gene activity within a cell, a cell extract, or other experimental sample is a compound that decreases the biological activity of a target polypeptide.

By "assaying" is meant analyzing the effect of a treatment, be it chemical or physical, administered to whole animals, cells, tissues, or molecules derived therefrom. The material being analyzed may be an animal, a cell, a tissue, a lysate or extract derived from a cell, or a molecule derived from a cell. The analysis may be, for example, for the purpose of detecting altered cell function, altered gene expression, altered endogenous RNA stability, altered polypeptide stability, altered polypeptide levels, or altered polypeptide biological activity. The means for analyzing may include, for example, antibody labeling, immunoprecipitation, phosphorylation assays, glycosylation assays, and methods known to those skilled in the art for detecting nucleic acids. In some embodiments, assaying is conducted under selective conditions.

By "modulates" is meant changing, either by a decrease or an increase. As used herein, desirably a nucleic acid decreases the function of a cell, the expression of a target nucleic acid in a cell, or the biological activity of a target polypeptide in a cell by least 20%, more desirably by at least 30%, 40%, 50%, 60% or 75%, and most desirably by at least 90%. Also as used herein, desirably a nucleic acid increases the function of a cell, the expression of a target nucleic acid in a cell, or the biological activity of a target polypeptide in a cell by at least 1.5-fold to 2-fold, more desirably by at least 3-fold, and most desirably by at least 5-fold.

By "a decrease" is meant a lowering in the level of (a) protein (e.g., as measured by ELISA or Western blot analysis); (b) reporter gene activity (e.g., as measured by reporter gene assay, for example, β-galactosidase, green fluorescent protein, or luciferase activity); (c) mRNA (e.g., as measured by RT-PCR or Northern blot analysis relative to an internal control, such as a "housekeeping" gene product, for example, β-actin or glyceraldehyde 3-phosphate dehydrogenase (GAPDH)); or (d) cell function, for example, as assayed by the number of apoptotic, mobile, growing, cell cycle arrested, invasive, differentiated, or dedifferentiated cells in a test sample. In all cases, the lowering is desirably by at least 20%, more desirably by at least 30%, 40%, 50%, 60%, 75%, and most desirably by at least 90%. As used herein, a decrease may be the direct or indirect result of PTGS, TGS, or another gene silencing event.

By "an increase" is meant a rise in the level of (a) protein (e.g., as measured by ELISA or Western blot analysis); (b) reporter gene activity (e.g., as measured by reporter gene assay, for example, β-galactosidase, green fluorescent protein, or luciferase activity); (c) mRNA (e.g., as measured by RT-PCR or Northern blot analysis relative to an internal control, such as a "housekeeping" gene product, for example, β-actin or glyceraldehyde 3-phosphate dehydrogenase (GAPDH)); or (d) cell function, for example, as assayed by the number of apoptotic, mobile, growing, cell cycle arrested, invasive, differentiated, or dedifferentiated cells in a test sample. Desirably, the increase is by at least 1.5-fold to 2-fold, more desirably by at least 3-fold, and most desirably by at least 5-fold. As used herein, an increase may be the indirect result of PTGS, TGS, or another gene silencing event. For example, the dsRNA may inhibit the expression of a protein, such as a suppressor protein, that would otherwise inhibit the expression of another nucleic acid.

By "alteration in the level of gene expression" is meant a change in transcription, translation, or mRNA or protein stability such that the overall amount of a product of the gene, i.e., mRNA or polypeptide, is increased or decreased.

By "reporter gene" is meant any gene that encodes a product whose expression is detectable and/or able to be quantitated by immunological, chemical, biochemical, or biological assays. A reporter gene product may, for example, have one of the following attributes, without restriction: fluorescence (e.g., green fluorescent protein), enzymatic activity (e.g., β-galactosidase, luciferase, chloramphenicol acetyltransferase), toxicity (e.g., ricin A), or an ability to be specifically bound by an additional molecule (e.g., an unlabeled antibody, followed by a labelled secondary antibody, or biotin, or a detectably labelled antibody). It is understood that any engineered variants of reporter genes that are readily available to one skilled in the art, are also included, without restriction, in the foregoing definition.

By "protein" or "polypeptide" or "polypeptide fragment" is meant any chain of more than two amino acids, regardless of post-translational modification (e.g., glycosylation or phosphorylation), constituting all or part of a naturally-occurring polypeptide or peptide, or constituting a non-naturally occurring polypeptide or peptide.

By "promoter" is meant a minimal sequence sufficient to direct transcription of a gene. Also included in this definition are those transcription control elements (e.g., enhancers) that are sufficient to render promoter-dependent gene expression controllable in a cell type-specific, tissue-specific, or temporal-specific manner, or that are inducible by external signals or agents; such elements, which are well-known to skilled artisans, may be found in a 5' or 3' region of a gene or within an intron. Desirably a promoter is operably linked to a nucleic acid sequence, for example, a cDNA or a gene in such a way as to permit expression of the nucleic acid sequence.

By "operably linked" is meant that a gene and one or more transcriptional regulatory sequences, e.g., a promoter or enhancer, are connected in such a way as to permit gene expression when the appropriate molecules (e.g., transcriptional activator proteins) are bound to the regulatory sequences.

By "expression vector" is meant a DNA construct that contains at least one promoter operably linked to a downstream gene or coding region (e.g., a cDNA or genomic DNA fragment that encodes a protein, optionally, operatively linked to sequence lying outside a coding region, an antisense RNA coding region, or RNA sequences lying outside a coding region). Transfection or transformation of the expression vector into a recipient cell allows the cell to express RNA encoded by the expression vector. An expression vector may be a genetically engineered plasmid, virus, or artificial chromosome derived from, for example, a bacteriophage, adenovirus, retrovirus, poxvirus, or herpesvirus.

By "transformation" or "transfection" is meant any method for introducing foreign molecules into a cell (e.g., a bacterial, yeast, fungal, algal, plant, insect, or animal cell, particularly a vertebrate or mammalian cell). The cell may be in an animal. Lipofection, DEAE-dextran-mediated transfection, microinjection, protoplast fusion, calcium phosphate precipitation, viral or retroviral delivery, electroporation, and biolistic transformation are just a few of the transformation/transfection methods known to those skilled in the art. The RNA or RNA expression vector (DNA) may be naked RNA or DNA or local anesthetic complexed RNA or DNA (Pachuk et al., supra). Other standard transformation/transfection methods and other RNA and/or DNA delivery agents (e.g., a cationic lipid, liposome, or bupivacaine) are described in WO 00/63364, filed Apr. 19, 2000 (see, for example, pages 18-26). Commercially available kits can also be used to deliver RNA or DNA to a cell. For example, the Transmessenger Kit from Qiagen, an RNA kit from Xeragon Inc., and an RNA kit from DNA Engine Inc. (Seattle, Wash.) can be used to introduce single or dsRNA into a cell.

By "transformed cell" or "transfected cell" is meant a cell (or a descendent of a cell) into which a nucleic acid molecule, for example, a dsRNA or double stranded expression vector has been introduced, by means of recombinant nucleic acid techniques. Such cells may be either stably or transiently transfected.

By "selective conditions" is meant conditions under which a specific cell or group of cells can be selected for. For example, the parameters of a fluorescence-activated cell sorter (FACS) can be modulated to identify a specific cell or group of cells. Cell panning, a technique known to those skilled in the art, is another method that employs selective conditions.

As use herein, by "optimized" is meant that a nucleic acid fragment is generated through inefficient first strand synthesis (e.g., reverse transcription (RT) and/or RT/second strand synthesis (RT-SSS) using Klenow or other enzymes and/or RT-PCR or PCR, to be of a particular length. Desirably the length of the nucleic acid fragment is less than a full length cDNA or is 100, 500, 600, or 1000 nucleotides in length. In other embodiments, the nucleic acid fragment is at least 10, 20, 30, 40, 50, 60, 70, 80, or 90 nucleotides in length. In yet other embodiments, the number of nucleotides in the nucleic acid fragment is between 5-100 nucleotides, 15-100 nucleotides, 20-95 nucleotides, 25-90 nucleotides, 35-85 nucleotides, 45-80 nucleotides, 50-75 nucleotides, or 55-70 nucleotides, inclusive. In still other embodiments, the number of nucleotides in the nucleic acid fragment is contained in one of the following ranges: 5-15 nucleotides, 15-20 nucleotides, 20-25 nucleotides, 25-35 nucleotides, 35-45 nucleotides, 45-60 nucleotides, 60-70 nucleotides, 70-80 nucleotides, 80-90 nucleotides, or 90-100 nucleotides, inclusive. In other embodiments, the nucleic acid fragment contains less than 50,000; 10,000; 5,000; or 2,000 nucleotides. Optimization of the length of a nucleic acid can be achieved during first strand or second strand synthesis of a desired nucleic acid by lowering $Mg^{++}$ concentrations to no less than the nucleotide concentrations; by adding $Mn^{++}$ to the reaction to achieve the desired size selection (e.g., by replacing $Mg^{++}$ completely, or by adding $Mn^{++}$ at varying concentrations along with $Mg^{++}$); by decreasing and/or limiting concentrations of dNTP(s) to effect the desired fragment size; by using various concentrations of ddNTP(s) along with standard or optimal concentrations of dNTP(s), to achieve varying ratios, to obtain the desired fragment size; by using limited and controlled exonuclease digestion of the fragment following RT, RT-SSS, RT-PCR, or PCR; or by a combination of any of these methods.

As used herein, by "sized selected" is meant that a nucleic acid of a particular size is selected for use in the construction of dsRNA expression libraries as described herein. Desirably the size selected nucleic acid is less than a full length cDNA sequence or at least 100, 500, 600, or 1000 nucleotides in length. In other embodiments, the nucleic acid is at least 10, 20, 30, 40, 50, 60, 70, 80, or 90 nucleotides in length. In yet other embodiments, the number of nucleotides in the nucleic acid is between 5-100 nucleotides, 15-100 nucleotides, 20-95 nucleotides, 25-90 nucleotides, 35-85 nucleotides, 45-80 nucleotides, 50-75 nucleotides, or 55-70 nucleotides, inclusive. In still other embodiments, the number of nucleotides in the nucleic acid is contained in one of the following ranges: 5-15 nucleotides, 15-20 nucleotides, 20-25 nucleotides, 25-35 nucleotides, 35-45 nucleotides, 45-60 nucleotides, 60-70 nucleotides, 70-80 nucleotides, 80-90 nucleotides, or 90-100 nucleotides, inclusive. In other embodiments, the nucleic acid contains less than 50,000; 10,000; 5,000; or 2,000 nucleotides. For example, a nucleic acid may be size selected using size exclusion chromatography (e.g., as size exclusion Sepharose matrices) according to standard procedures (see, for example, Sambrook, Fritsch, and Maniatis, *Molecular Cloning: A Laboratory Manual* (3rd ed.), Cold Spring Harbor Laboratory Press, Cold Spring Harbor, N.Y., 2001).

By "under conditions that inhibit or prevent an interferon response or a dsRNA stress response" is meant conditions that prevent or inhibit one or more interferon responses or cellular RNA stress responses involving cell toxicity, cell death, an anti-proliferative response, or a decreased ability of a dsRNA to carry out a PTGS event. These responses include, but are not limited to, interferon induction (both Type 1 and Type II), induction of one or more interferon stimulated genes, PKR activation, 2'5'-OAS activation, and any downstream cellular and/or organismal sequelae that result from the activation/induction of one or more of these responses. By "organismal sequelae" is meant any effect(s) in a whole animal, organ, or more locally (e.g., at a site of injection) caused by the stress response. Exemplary manifestations include elevated cytokine production, local inflammation, and necrosis. Desirably the conditions that inhibit these responses are such that not more than 95%, 90%, 80%, 75%, 60%, 40%, or 25%, and most desirably not more than 10% of the cells undergo cell toxicity, cell death, or a decreased ability to carry out a PTGS, TGS, or other gene silencing event, compared to a cell not exposed to such interferon response inhibiting conditions, all other conditions being equal (e.g., same cell type, same transformation with the same dsRNA expression library.

Apoptosis, interferon induction, 2'5' OAS activation/induction, PKR induction/activation, anti-proliferative responses, and cytopathic effects are all indicators for the RNA stress response pathway. Exemplary assays that can be used to measure the induction of an RNA stress response as described herein include a TUNEL assay to detect apoptotic cells, ELISA assays to detect the induction of alpha, beta and gamma interferon, ribosomal RNA fragmentation analysis to detect activation of 2'5'OAS, measurement of phosphorylated eIF2a as an indicator of PKR (protein kinase RNA inducible) activation, proliferation assays to detect changes in cellular proliferation, and microscopic analysis of cells to identify cellular cytopathic effects (see, e.g., Example 11). Desirably, the level of an interferon response or a dsRNA stress response in a cell transformed with a dsRNA or a dsRNA expression vector is less than 20, 10, 5, or 2-fold greater than the corresponding level in a mock-transfected control cell under the same conditions, as measured using one of the assays described herein. In other embodiments, the level of an interferon response or a dsRNA stress response in a cell transformed with a dsRNA or a dsRNA expression vector using the methods of the present invention is less than 500%, 200%, 100%, 50%, 25%, or 10% greater than the corresponding level in a corresponding transformed cell that is not exposed to such interferon response inhibiting conditions, all other conditions being equal. Desirably, the dsRNA does not induce a global inhibition of cellular transcription or translation.

By "specifically hybridizes" is meant a dsRNA that hybridizes to a target nucleic acid but does not substantially hybridize to other nucleic acids in a sample (e.g., a sample from a cell) that naturally includes the target nucleic acid, when assayed under denaturing conditions. In one embodiment, the amount of a target nucleic acid hybridized to, or associated with, the dsRNA, as measured using standard assays, is 2-fold, desirably 5-fold, more desirably 10-fold, and most desirably 50-fold greater than the amount of a control nucleic acid hybridized to, or associated with, the dsRNA.

By "substantial sequence identity" is meant sufficient sequence identity between a dsRNA and a target nucleic acid for the dsRNA to inhibit the expression of the nucleic acid. Preferably, the sequence of the dsRNA is at least 40, 50, 60, 70, 80, 90, 95, or 100% identical to the sequence of a region of the target nucleic acid.

By "specifically inhibits the expression of a target nucleic acid" is meant inhibits the expression of a target nucleic acid more than the expression of other, non-target nucleic acids which include other nucleic acids in the cell or biological sample having a sequence that is less than 99, 95, 90, 80, or 70% identical or complementary to that of the target nucleic acid. Desirably, the inhibition of the expression of these non-target molecules is 2-fold, desirably 5-fold, more desirably 10-fold, and most desirably 50-fold less than the inhibition of the expression the target nucleic acid.

By "high stringency conditions" is meant hybridization in 2×SSC at 40C with a DNA probe length of at least 40 nucleotides. For other definitions of high stringency conditions, see F. Ausubel et al., *Current Protocols in Molecular Biology*, pp. 6.3.1-6.3.6, John Wiley & Sons, New York, N.Y., 1994, hereby incorporated by reference.

Conditions and techniques that can be used to prevent an interferon response or dsRNA stress response during the screening methods of the present invention are described herein.

BRIEF DESCRIPTION OF THE DRAWINGS

FIGS. 4A and 4B are lists of sequences for dsRNA molecules used to inhibit expression of SEAP or IL-12. FIG. 4A contains SEQ ID NOs: 1-9, and FIG. 4B contains SEQ ID NOs: 10-18.

DETAILED DESCRIPTION OF THE INVENTION

Figure 1:
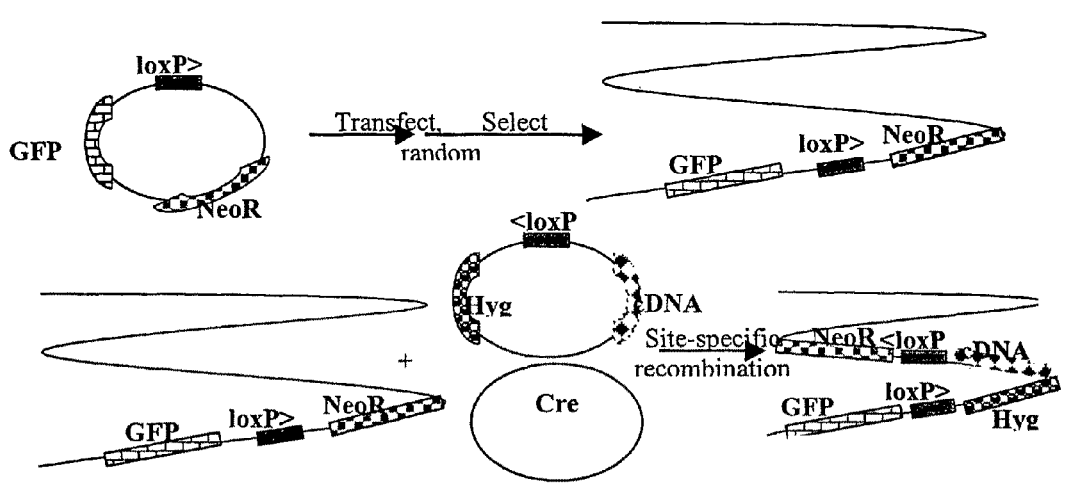
FIG. 1 is a schematic representation of a strategy to isolate clonally pure stable integrants that contain a single expression unit isolated from cells transfected with a double-stranded RNA encoding a cDNA library.

The present invention is based on the surprising discovery that short dsRNA molecules (e.g., dsRNA molecules containing a region of between 11 and 40 nucleotides in length that is in a double stranded conformation) can be used to inhibit the PKR/interferon/stress/cytotoxicity response induced by other dsRNA molecules (e.g., short or long dsRNA molecules homologous to one or more target genes) in vertebrate cells, tissues, and organisms. For example, short dsRNA can be used to inhibit toxicity that may otherwise be induced by long dsRNA (e.g., long dsRNA that is homologous to a target nucleic acid). In particular, two short dsRNA molecules prevented the toxic effects that are normally induced by the dsRNA poly (I)(C) (Example 2). Additionally, a first short dsRNA can be used to inhibit toxicity that may otherwise be induced by a second short dsRNA that is homologous to a target nucleic acid, such as a second short dsRNA that induces toxicity because it has a sequence with affinity for PKR or another component in the dsRNA-mediated stress response pathway. The first short dsRNA that is administered to inhibit toxicity may, for example, inhibit the binding of the second dsRNA to PKR or inhibit the dimerization or activation of PKR. Thus, the present methods inhibit the induction of non-specific cytotoxicity and cell death by dsRNA molecules (e.g., long dsRNA molecules) that would otherwise preclude their use for gene silencing in vertebrate cells and vertebrates.

Important Role of PKR in dsRNA-Mediated Toxicity

The cytotoxicity triggered by dsRNA molecules is a complex, multi-pathway process. Protein kinase PKR is an important component of the Type 1 interferon response. PKR is constitutively present in most cell types in its inactive monomer form. PKR must dimerize in order to become activated. Activation is mediated through a process involving autophosphorylation. Once activated, PKR catalyzes the intermolecular phosphorylation of a number of molecules including translation factor eIF-2alpha. This serine phosphorylation of eIF-2alpha results in global inhibition of translation initiation. A basal level of phosphorylated eIF-2alpha is present in most cells and most likely reflects a basal level of activated PKR in these cells.

PKR has a dsRNA binding motif that has been shown to be able to bind dsRNA as small as 11 nucleotides in length. However, PKR activation has been shown to require dsRNA of at least 30 nucleotides in length, with an optimal length of about 80 nucleotides. The requirement for at least 30 nucleotides for activation is thought to reflect the length of dsRNA that is required for two PKR monomers to sit next to each other on the same dsRNA molecule. Thus, binding of two monomers to the same dsRNA molecule enables dimerization of PKR. This process is referred to as RNA-dependent activation.

While not meant to limit the invention to any specific mechanism of action, the present methods for preventing the interferon response may provide short dsRNA molecules that are of a size sufficient to bind PKR, but small enough to prevent two PKR molecules from binding. When supplied at a high enough level or concentration, these short dsRNA molecules may titrate out all of the PKR monomers and prevent them from dimerizing. Because dimerized PKR dissociates into two PKR monomers, the released monomers may also be captured by short dsRNA. If this mechanism is involved, global translation is expected to increase following administration of short dsRNA molecules because short dsRNA molecules may decrease the basal level of activated PKR. Consistent with this mechanism, short dsRNA was found to increase the expression of an unrelated gene (Example 2).

Although the short dsRNA molecules are most likely preventing dimerization, they could also be acting in a similar manner with respect to other components of the interferon response pathway(s) because many of these components also have dsRNA binding domains.

Applications of Present Methods

Short dsRNA molecules can be used in conjunction with exogenously added or endogenously expressed dsRNA molecules in gene silencing applications to prevent the activation of PKR that would otherwise be elicited by the latter dsRNA. Currently, the administration of such exogenously added dsRNA to cells and animals for gene-silencing experiments is limited by the cytotoxicity induced by dsRNA (e.g., long dsRNA). Short dsRNA or a vector stably or transiently expressing short dsRNA can be delivered before (e.g., 10, 20, 30, 45, 60, 90, 120, 240, or 300 minutes before), during, or after (e.g., 2, 5, 10, 20, 30, 45, 60, or 90 minutes after) the delivery of exogenous dsRNA or a vector encoding dsRNA to animals or cell cultures. A vector expressing a short dsRNA can also be administered up to 1, 2, 3, 5, 10, or more days before administration of dsRNA homologous to a target nucleic acid. A vector expressing short dsRNA can be administered any number of days before the administration of dsRNA homologous to a target nucleic acid (e.g., target-specific dsRNA) or a vector encoding this dsRNA, as long as the dsRNA-mediated stress response pathway is still inhibited by the short dsRNA when the target-specific dsRNA is administered. The timing of the delivery of these nucleic acids can be readily be selected or optimized by one skilled in the art of pharmacology using standard methods. The methods of the invention may also be useful in any circumstances in which PKR suppression is desired; e.g., in DNA expression systems in which small amounts of dsRNA may be inadvertently formed when transcription occurs from cryptic promoters within the non-template strand. The present invention is also useful for industrial applications such as the manufacture of dsRNA molecules in vertebrate cell cultures. The present invention can be used to make "knockout" or "knockdown" vertebrate cell lines or research organisms (e.g., mice, rabbits, sheep, or cows) in which one or more target nucleic acids are silenced. The present invention also allows the identification of the function of a gene by determining the effect of inactivating the gene in a vertebrate cell or organism. These gene silencing methods can also be used to validate a selected gene as a potential target for drug discovery or development.

The methods of the invention can also treat, stabilize, or prevent diseases associated with the presence of an endogenous or pathogen protein in vertebrate organisms (e.g., human and non-human mammals). These methods are expected to be especially useful for therapeutic treatment for viral diseases, including chronic viral infections such as HBV, HIV, papilloma viruses, and herpes viruses. In some embodiments, the methods of the invention are used to prevent or treat acute or chronic viral diseases by targeting a viral nucleic acid necessary for replication and/or pathogenesis of the virus in a mammalian cell. Slow virus infection characterized by a long incubation or a prolonged disease course are especially appropriate targets for the methods of the invention, including such chronic viral infections as HTLV-I, HTLV-II, EBV, HBV, CMV, HCV, HIV, papilloma viruses, and herpes viruses. For prophylaxis of viral infection, the selected gene target is desirably introduced into a cell together with the short dsRNA and long dsRNA molecules of the invention. Particularly suitable for such treatment are various species of the Retroviruses, Herpesviruses, Hepadnaviruses, Poxviruses, Papillomaviruses, and Papovaviruses. Exemplary target genes necessary for replication and/or pathogenesis of the virus in an infected vertebrate (e.g., mammalian) cell include nucleic acids of the pathogen or host necessary for entry of the pathogen into the host (e.g., host T cell CD4 receptors), nucleic acids encoding proteins necessary for viral propagation (e.g., HIV gag, env, and pol), and regulatory genes such as tat and rev. Other exemplary targets include nucleic acids for HIV reverse transcriptase, HIV protease, HPV6 L1 and E2 genes, HPV11 L1 and E2 genes, HPV16 E6 and E7 genes, HPV18 E6 and E7 genes, HBV surface antigens, core antigen, and reverse transcriptase, HSD gD gene, HSVvp16 gene, HSVgC, gH, gL, and gB genes, HSV ICP0, ICP4, and ICP6 genes; Varicella zoster gB, gC and gH genes, and non-coding viral polynucleotide sequences which provide regulatory functions necessary for transfer of the infection from cell to cell (e.g., HIV LTR and other viral promoter sequences such as HSV vp16 promoter, HSV-ICP0 promoter, HSV-ICP4, ICP6, and gD promoters, HBV surface antigen promoter, and HBV pre-genomic promoter). Desirably, a dsRNA (e.g., long dsRNA) of the invention reduces or inhibits the function of a viral nucleic acid in the cells of a mammal or vertebrate, and a short dsRNA of the invention blocks the dsRNA stress response that may be triggered by dsRNA.

Other exemplary pathogens include bacteria, rickettsia, chlamydia, fungi, and protozoa such as extraintestinal pathogenic protozoa which cause malaria, babesiosis, trypanosomiasis, leishmaniasis, or toxoplasmosis. The intracellular malaria-causing pathogen *Plasmodium* species *P. falciparum, P. vivax, P. ovale*, and *P. malariae* are desirable targets for dsRNA-mediated gene silencing, especially in the chronic, relapsing forms of malaria. Other intracellular pathogens include *Babesia microti* and other agents of Babesiosis, protozoa of the genus *Trypanosoma* that cause African sleeping sickness and American Trypanosomiasis or Chagas' Disease; *Toxoplasma gondii* which causes toxoplasmosis, *Mycobacterium tuberculosis, M. bovis*, and *M avium* complex which cause various tuberculous diseases in humans and other animals. Desirably, a dsRNA (e.g., long dsRNA) of the invention reduces or inhibits the function of a pathogen nucleic acid in the cells of a mammal or vertebrate, and a short dsRNA of the invention blocks the dsRNA stress response that may be triggered by dsRNA.

In some methods for the prevention of an infection, a pathogen target gene or a region from a pathogen target gene (e.g., a region from an intron, exon, untranslated region, promoter, or coding region) is introduced into the cell or animal. For example, this target nucleic acid can be inserted into a vector that desirably integrates in the genome of a cell and administered to the cell or animal. Alternatively, this target nucleic acid can be administered without being incorporated into a vector. The presence of a region or an entire target nucleic acid in the cell or animal is expected to enhance the amplification of the simultaneously or sequentially administered dsRNA that is homologous to the target gene. The amplified dsRNA or amplified cleavage products from the dsRNA silence the target gene in pathogens that later infect the cell or animal. Short dsRNA is also administered to the cell or animal to inhibit dsRNA-mediated toxicity.

Similarly, to silence an endogenous target gene that is not currently being expressed in a particular cell or animal, it may be necessary to introduce a region from the target gene into the cell or animal to enhance the amplification of the administered dsRNA that is homologous to the target gene. The amplified dsRNA or amplified cleavage products from the dsRNA desirably prevent or inhibit the later expression of the target gene in the cell or animal. Desirably, short dsRNA is also administered to inhibit toxic effects.

Still other exemplary target nucleic acids encode a prion, such as the protein associated with the transmissible spongiform encephalopathies, including scrapie in sheep and goats; bovine spongiform encephalopathy (BSE) or "Mad Cow Disease", and other prion diseases of animals, such as transmissible mink encephalopathy, chronic wasting disease of mule deer and elk, and feline spongiform encephalopathy. Prion diseases in humans include Creutzfeldt-Jakob disease, kuru, Gerstmann-Straussler-Scheinker disease (which is manifest as ataxia and other signs of damage to the cerebellum), and fatal familial insomnia. Desirably, a dsRNA (e.g., long dsRNA) of the invention reduces or inhibits the function of a prion nucleic acid in the cells of a mammal or vertebrate, and a short dsRNA of the invention blocks the dsRNA stress response that may be triggered by dsRNA.

The invention also provides compositions and methods for treatment or prophylaxis of a cancer in a mammal by administering to the mammal one or more of the compositions of the invention in which the target nucleic acid is an abnormal or abnormally expressed cancer-causing gene, tumor antigen or portion thereof, or a regulatory sequence. Desirably, the target nucleic acid is required for the maintenance of the tumor in the mammal. Exemplary oncogene targets include ABL1, BRAF, BCL1, BCL2, BCL6, CBFA2, CSF1R, EGFR, ERBB2 (HER-2/neu), FOS, HRAS, MYB, MYC, LCK, MYCL1, MYCN, NRAS, ROS1, RET, SRC, and TCF3. Such an abnormal nucleic acid can be, for example, a fusion of two normal genes, and the target sequence can be the sequence which spans that fusion, e.g., the bcr/abl gene sequence (Philadelphia chromosome) characteristic of certain chronic myeloid leukemias, rather than the normal sequences of the non-fused bcr and abl (see, e.g., WO 94/13793, published Jun. 23, 1994, the teaching of which is hereby incorporated by reference). Viral-induced cancers are particularly appropriate for application of the compositions and methods of the invention. Examples of these cancers include human-papillomavirus (HPV) associated malignancies which may be related to the effects of oncoproteins, E6 and E7 from HPV subtypes 16 and 18, p53 and RB tumor suppressor genes, and Epstein-Barr virus (EBV) which has been detected in most Burkitt's-like lymphomas and almost all HIV-associated CNS lymphomas. The composition is administered in an amount sufficient to reduce or inhibit the function of the tumor-maintaining nucleic acid in the mammal.

The gene silencing methods of the present invention may also employ a multitarget or polyepitope approach. Desirably, the sequence of the dsRNA includes regions homologous to genes of one or more pathogens, multiple genes or epitopes from a single pathogen, multiple endogenous genes to be silenced, or multiple regions from the same gene to be silenced. Exemplary regions of homology including regions homologous to exons, introns, or regulatory elements such as promoter regions and non-translated regions.

The following examples are to illustrate the invention. They are not meant to limit the invention in any way. For example, it is noted that any of the following examples can be used with dsRNA molecules of any length that are substantially identical to a region of a target nucleic acid. The methods of the present invention can be readily adapted by one skilled in the art to utilize multiple dsRNA molecules to inhibit multiple target nucleic acids. Any of the dsRNA molecules, target nucleic acids, or methods described by Giordano, Pachuk, and Satishchandran (U.S. Ser. No. 10/062,707, filed Jan. 31, 2002, "Use of post-transcriptional gene silencing for identifying nucleic acid sequences that modulate the function of a cell") can also be used in the present methods.

While the use of the present invention is not limited to vertebrate or mammalian cells, such cells can be used to carry out the methods described herein. Desirably, the vertebrate (e.g., mammalian) cells used to carry out the present invention are cells that have been cultured for only a small number of passages (e.g., less than 30 passages of a cell line that has been obtained directly from American Type Culture Collection), or are primary cells. In addition, vertebrate (e.g., mammalian) cells can be used to carry out the present invention when the dsRNA being transfected into the cell is not complexed with cationic lipids.

EXAMPLE 1

Exemplary Methods for the Generation and Administration of dsRNA

Generation of dsRNA

Short and long dsRNA can be made using a variety of methods known to those of skill in the art. For example, ssRNA sense and antisense strands can be synthesized chemically in vitro [see, for example, Q. Xu et al, *Nucl. Acids Res.*, 24 (18): 3643-4, 1996 and other references cited in WO 00/63364, pp. 16-7], transcribed in vitro using commercially available materials and conventional enzymatic synthetic methods, (e.g., using the bacteriophage T7, T3, or SP6 RNA polymerases according to conventional methods such as those described by *Promega Protocols and Applications Guide* $3^{rd}$ Ed., Eds. Doyle, 1996, ISBN No. 1-882274-57-1], or expressed in cell culture using recombinant methods. The RNA can then be purified using non-denaturing methods including various chromatographic methods and hybridized to form dsRNA. Such methods are well known to those of skill in the art and are described, for example, in WO 01/75164, WO 00/63364, and Sambrook et al., *Molecular Cloning, A Laboratory Manual*, $2^{nd}$ Ed.; Cold Spring Harbor Laboratory Press, New York, 1989, the teaching of which is incorporated herein by reference.

In vitro transcription reactions are carried out using the Riboprobe Kit (Promega Corp.), according to the manufacturer's directions. The template DNA is as described above. Following synthesis, the RNA is treated with RQ1 DNase (Promega Corp.) to remove template DNA. The RNA is then treated with Proteinase K and extracted with phenol-chloroform to remove contaminating RNases. The RNA is ethanol precipitated, washed with 70% ethanol, and resuspended in RNase-free water. Aliquots of RNA are removed for analysis and the RNA solution is flash frozen by incubating in an ethanol-dry ice bath. The RNA is stored at −80° C.

As an alternative to phenol-chloroform extraction, RNA can be purified in the absence of phenol using standard methods such as those described by Li et al. (WO 00/44914, filed Jan. 28, 2000). Alternatively, RNA that is extracted with phenol and/or chloroform can be purified to reduce or eliminate the amount of phenol and/or chloroform. For example, standard column chromatography can be used to purify the RNA (WO 00/44914, filed Jan. 28, 2000).

Double stranded RNA is made by combining equimolar amounts of PCR fragments encoding antisense RNA and sense RNA, as described above, in the transcription reaction. Single stranded antisense or sense RNA is made by using a single species of PCR fragment in the reaction. The RNA concentration is determined by spectrophotometric analysis, and RNA quality is assessed by denaturing gel electrophoresis and by digestion with RNase T1, which degrades single stranded RNA.

An mRNA library is produced using Qbeta bacteriophage, by ligating the mRNA molecules to the flank sequences that are required for Qbeta replicase function (Qbeta flank or Qbeta flank plus P1), using RNA ligase. The ligated RNA molecules are then transformed into bacteria that express Qbeta replicase and the coat protein. Single plaques are then inoculated into fresh bacteria. All plaques are expected to carry transgene sequences. Each plaque is grown in larger quantities in bacteria that produce the Qbeta polymerase, and RNA is isolated from the bacteriophage particles. Alternatively, if the Qbeta flank plus P1 is used to generate the library (e.g., P1=MS2, VEEV, or Sindbis promoter sequences), these vectors can be used to carry out the in vitro transcription along with the cognate polymerase. The in vitro made dsRNA is then used to transfect cells.

Administration of dsRNA

The short dsRNA molecules and long dsRNA molecules may be delivered as "naked" polynucleotides, by injection, electroporation, or any polynucleotide delivery method known to those of skill in the field of RNA and DNA. For example, in vitro synthesized dsRNA may be directly added to a cell culture medium. Uptake of dsRNA is also facilitated by electroporation using those conditions required for DNA uptake by the desired cell type. RNA uptake is also mediated by lipofection using any of a variety of commercially available and proprietary cationic lipids, DEAE-dextran-mediated transfection, microinjection, protoplast fusion, calcium phosphate precipitation, viral or retroviral delivery, anesthetic RNA complex, or biolistic transformation.

Alternatively, the RNA molecules may by delivered by an agent (e.g., a double-stranded DNA molecule) that generates an at least partially double stranded molecule in cell culture, in a tissue, or in vivo in a vertebrate or mammal. The DNA molecule provides the nucleotide sequence which is transcribed within the cell to become an at least partially double stranded RNA. These compositions desirably contain one or more optional polynucleotide delivery agents or co-agents, such as a cationic amphiphile local anesthetic such as bupivacaine, a peptide, cationic lipid, a liposome or lipidic particle, a polycation such as polylysine, a branched, three-dimensional polycation such as a dendrimer, a carbohydrate, a cationic amphiphile, a detergent, a benzylammonium surfactant, one or more multifunctional cationic polyamine-cholesterol agents disclosed in U.S. Pat. No. 5,837,533 and U.S. Pat. No. 6,127,170, or another of the many compounds known in the art to facilitate delivery of polynucleotides into cells. Non-exclusive examples of such facilitating agents or co-agents are described in U.S. Pat. No. 5,593,972; U.S. Pat. No. 5,703,055; U.S. Pat. No. 5,837,533; U.S. Pat. No. 6,127,170; U.S. Pat. No. 5,962,428, U.S. Pat. No. 6,197,755, WO 96/10038, published Apr. 4, 1996, and WO 94/16737, published Aug. 8, 1994, the teaching of which are hereby incorporated by reference.

For administration of dsRNA (e.g., a short dsRNA to inhibit toxicity or a long dsRNA to silence a gene) to a cell or cell culture, typically between 50 ng and 5 ug, such as between 50 ng and 500 ng or between 500 ng and 5 ug dsRNA is used per one million cells. For administration of a vector encoding dsRNA (e.g., a short dsRNA to inhibit toxicity or a long dsRNA to silence a gene) to a cell or cell culture, typically between 10 ng and 2.5 ug, such as between 10 ng and 500 ng or between 500 ng and 2.5 ug dsRNA is used per one million cells. Other doses, such as even higher doses may also be used.

For administration of dsRNA (e.g., a short dsRNA to inhibit toxicity or a long dsRNA to silence a gene) to an animal, typically between 10 mg to 100 mg, 1 mg to 10 mg, 500 ug to 1 mg, or 5 ug to 500 ug dsRNA is administered to a 90-100 pound person animal (in order of increasing preference). For administration of a vector encoding dsRNA (e.g., a short dsRNA to inhibit toxicity or a long dsRNA to silence a gene) to an animal, typically between 100 mg to 300 mg, 10 mg to 100 mg, 1 mg to 10 mg, 500 ug to 1 mg, or 50 ug to 500 ug dsRNA is administered to a 90-100 pound person (in order of increasing preference). The dose may be adjusted based on the weight of the animal. In some embodiments, about 1 to 10 mg/kg or about 2 to 2.5 mg/kg is administered. Other doses may also be used.

For administration to an intact animal, typically between 10 ng and 50 ug, between 50 ng and 100 ng, or between 100 ng and 5 ug of dsRNA or DNA encoding a dsRNA is used. In desirably embodiments, approximately 10 ug of a DNA or 5 ug of dsRNA is administered to the animal. With respect to the methods of the invention, it is not intended that the administration of dsRNA or DNA encoding dsRNA to cells or animals be limited to a particular mode of administration, dosage, or frequency of dosing; the present invention contemplates all modes of administration sufficient to provide a dose adequate to inhibit gene expression, prevent a disease, or treat a disease.

Short dsRNA is delivered before, during, or after the delivery of the dsRNA (e.g., a longer dsRNA) that might otherwise be expected to induce cytotoxicity. If desired, modulation of cell function, gene expression, or polypeptide biological activity is then assessed in the cells or animals.

EXAMPLE 2

Demonstration that Short dsRNA Induces an Increase in Global Translation, Most Likely due to Inhibition of PKR Activation To evaluate the use of short dsRNA for post transcriptional gene silencing (PTGS), short dsRNA homologous to SEAP (human placental secreted heat-stable alkaline phosphatase) and murine IL-12 were tested individually for their ability to silence exogenous SEAP and IL-12 genes (FIGS. 4A and 4B). In particular, human rhabdomyosarcoma cells were transiently transfected with both SEAP and murine IL-12 expression vectors and thus expressed both SEAP and murine IL-12. Since both of these proteins are secreted, they were detected in the medium of cultured transfected cells. SEAP was measured using a calorimetric kinetic enzyme assay, and murine IL-12 was measured using a commercially available ELISA kit from R&D systems. Short dsRNA molecules designed against SEAP were transfected into the cells. The SEAP short dsRNA was expected to reduce the level of SEAP expression, but have no effect on the level of IL-12. The reciprocal experiment was also carried out in which short dsRNA molecules designed against murine IL-12 were transfected into the cells. The IL-12 short dsRNA was expected to reduce IL-12 levels but not effect SEAP levels. Thus SEAP and IL-12 serve as controls for each other. The amount of each vector per one million cells was 500 ng. The short dsRNA molecules were tested in three different amounts: 1.25 ug, 2.5 ug, and 5 ug per one million cells.

SEAP short dsRNA down-regulated SEAP production and surprisingly appeared to dramatically up-regulate IL-12 expression. Similarly, IL-12 short dsRNA down-regulated IL-12 as expected and surprisingly increased SEAP expression. Thus, the short dsRNA molecules down-regulated expression of their respective targets via PTGS as expected. One explanation of the unexpected increase in expression of an unrelated gene is that short dsRNA inhibits dimerization of PKR. In order to test this hypothesis, the following experiment was performed.

EXAMPLE 3

Co-Transfection of Short dsRNA with Poly (I)(C) prevents dsRNA-Induced Cytotoxicity Polyriboinosinic acid:polyribocytidylic acid [also called poly(I)(C)] is a commercially available synthetic RNA composition known to induce the interferon response (see, for example, Adamson, Nature, 223, Aug. 16, 1969; U.S. Pat. No. 4,283,393). Cytotoxicity following poly (I)(C) administration is mediated in part by PKR activation. Short dsRNA molecules with no known homology to RNA molecules expressed in RD cells were complexed with a commercially available cationic lipid composition (Lipofectamine). In particular the short dsRNA was a molecule containing a sequence from Human Hepatitis B (HBV) (the 25-mer CCUCCAAUCACUCACCAACCUCCUG, SEQ ID NO: 19). Any other short dsRNA sequence could also be used. Poly (I)(C) from Pharmacia, which is heterologous in length, was also complexed with Lipofectamine and used at a dose of 5 ug poly (I)(C) per one million cells. Other exemplary concentrations of poly(I)(C) or long dsRNA that may be used include about 50 ng to about 5 ug per one million cells or about 500 ng to about 5 ug per one million cells. To eliminate the PRK response, 2.5 ug of short dsRNA was also delivered to one million cells. Another exemplary concentration of short dsRNA that may be used to prevent toxicity in cell culture include 50 ng to 5 ug per one million cells. To prevent toxicity in animals, exemplary concentrations of short dsRNA include 500 ug to 1 mg, 1 mg to 10 mg, 10 mg to 100 mg, 5 ug to 100 mg, and more desirably 5 ug to 500 ug.

In this experiment, one set of RD cells was transfected with only poly (I)(C) while the second set of cells was transfected with poly(I)(C) and short dsRNA (at a dose of 2.5 ug each per one million cells). The cells were incubated and observed for several days. By 20 hours post-transfection, there was massive loss of the poly (I)(C) transfected cells to apoptosis.

Surprisingly, there was no cytotoxicity observed in cells transfected with both poly (I)(C) and short dsRNA, suggesting that the short dsRNA was protecting against cytotoxicity, even in the face of the massive insult provided by the poly(I)(C). This observation provides the basis for the present methods of using short dsRNA molecules to inhibit dsRNA-mediated toxicity in a variety of gene silencing (e.g., PTGS and TGS) applications.

EXAMPLE 4

Exemplary Method for Using Short dsRNA to Inhibit or Prevent dsRNA Mediated Toxicity In one gene silencing method, a long dsRNA (e.g., a dsRNA greater than 100, 200, 300, 400, 500, or more nucleotides) specific to a target gene such as SEAP is transfected into cells for the purpose of inducing sequence specific gene-silencing without inducing the type I interferon response (also known as the dsRNA stress response). Short dsRNA (e.g., one or more dsRNA molecules of approximately 18 or 25 nucleotides in length) are co-transfected with the long SEAP-specific dsRNA into cells expressing SEAP. Cells are maintained in culture and monitored for loss of SEAP expression. Cells are also observed for any indication of an interferon or other dsRNA-mediated cytotoxic response.

In Vitro Expression of SEAP Specific dsRNA (e.g., Long dsRNA)

Figure 3:
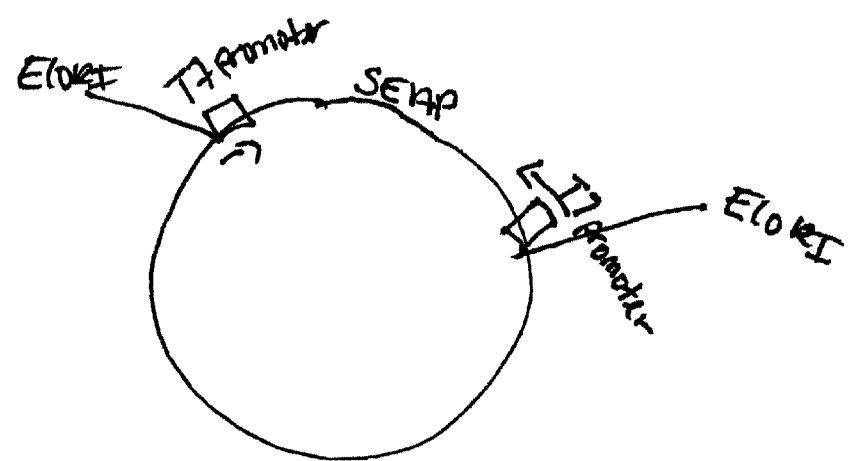
FIG. 3 is a schematic illustration of a vector containing nucleotides 400-1200 of accession number #U89938 (SEAP) for the generation of a dsRNA molecule specific for SEAP. The EcoRI fragment encoding SEA flanked by converging T7 promoters is used as a template for dsRNA synthesis.

A plasmid containing 800 nucleotides of SEAP situated between two converging T7 promoters is digested with a restriction enzyme (FIG. 3). The restriction fragment bearing the SEAP sequence flanked by the T7 promoters is gel purified using standard techniques. The purified fragment is treated with proteinase K to remove any contaminating RNA molecules, phenol and chloroform extracted, EtOH precipitated, and resuspended in RNase-free water using well known techniques. The purified fragment is then used as a template for in vitro transcription catalyzed by T7 RNA polymerase. Transcription is performed using a RiboMAX Large Scale RNA Production system kit from Promega Corporation according to the manufacturer's directions. RNA concentration is determined using 260/280 spectrophotometric analysis.

Generation of Short dsRNA

Short dsRNA was chemically synthesized by Dharmacon (Colorado). Short dsRNA can also be prepared enzymatically using a dsRNA synthesis kit available from Ambion according to the manufacturer's directions. Short dsRNA molecules are designed to avoid any extensive homology to known endogenously expressed mRNA molecules in human rhabdomyosarcoma cells, the cells used for these experiments (see for example, WO 00/63364 and WO 01/04313). When other cells are used, short dsRNA molecules are desirably designed to avoid extensive homology to mRNA molecules (e.g., essential mRNA molecules) normally expressed in those cells. It is also possible, however, for the short dsRNA molecules to have extensive homology to mRNA molecules that are not required for normal metabolism of the cell. Desirably, any inhibition of these mRNA molecules by the short dsRNA does not slow down or otherwise affect the growth rate or health of the cell.

Creation of Transient Expression Systems

Human rhabdomyosarcoma cells (RD) were transfected with both SEAP and murine IL-12 expression vectors. The accession number for the p40 subunit of murine IL-12 is M86671; the accession number for SEAP is U89938. Both SEAP and Il-12 were under the control of the HCMV promoter and the bovine growth hormone (BGH) polyadenylation signal. RD cells were cultured in DMEM (10% FBS) in T75 flasks until a 90-95% confluency was reached, and the cells were transfected with the SEAP and IL-12 expression vectors. Transfection was mediated using Lipofectamine (Invitrogen) according to the manufacturer's directions. Briefly, for each T75 flask of cells, 11 ug each of the SEAP and Il-12 expression vectors were added to 800 ul Optimem, a serum-free medium available from Invitrogen. In a separate tube, 80 ul Lipofectamine was added to 800 ul Optimem. The contents of the tube containing Lipofectamine was added to the tube containing the DNA. The mixture was allowed to incubate for 20 minutes at room temperature. During this incubation period, media was removed from the RD cells and replaced with 10 ml of Optimem. This Optimem wash was allowed to remain on the cells for 20 minutes after which time the Optimem was removed and replaced with seven mL of fresh Optimem. The transfection mixture (DNA vectors plus Lipofectamine) was added to the cells, and the cells were incubated for 17-20 hours, at which time the media containing the transfection mixture was removed from the cells and replaced with 15 mL DMEM (10% FBS). Cells began to secrete SEAP and IL-12 on that day and continued to secrete detectable levels of each protein for about one month.

Transfection of dsRNA

The day prior to transfection, RD cells transiently expressing both IL-12 and SEAP are seeded into individual wells of six-well plates at a density of about $7.5 \times 10^6$ per well and cultured overnight at 37° C. in DMEM (10% FBS). Each transfection is performed in quadruplicate. The following transfections are performed: short dsRNA (chemically synthesized), short dsRNA alone (enzymatically synthesized), SEAP-specific long dsRNA alone, SEAP-specific long dsRNA plus chemically synthesized short dsRNA, SEAP-specific long dsRNA plus enzymatically synthesized short dsRNA, and control untransfected cells. All transfection mixes are performed using Lipofectamine as described above and using similar charge to charge ratios of nucleic acid to Lipofectamine as described for creation of the transient expression systems above. Short dsRNA alone transfections are performed using 500 ng, 1 ug, 2.5 ug, or 5 ug complexed with Lipofectamine. Long dsRNA alone transfections are performed using 1 ug or 2.5 ug dsRNA complexed with Lipofectamine. For transfection of both long and short dsRNA, the long dsRNA (1 ug or 2.5 ug) and the short dsRNA (500 ng, 1 ug, 2.5 ug, or 5 ug) are complexed separately with Lipofectamine and then each added to the same cells at the time of transfection. Alternatively, short dsRNA and long dsRNA can be complexed together. Transfection mixes are incubated for 20-30 minutes at room temperature.

While transfection mixtures are incubating, media is removed from the cells in the six-well plates. Two ml of Optimem is added to each well, and the cells are incubated at 37° C. for about 15-20 minutes. The Optimem is removed and 800 ul Optimem is added per well. The transfection mixes are added such that some wells receive the short dsRNA molecules alone at each short dsRNA concentration, the long dsRNA molecules alone at each concentration, and the long dsRNA and short dsRNA at each concentration. For example, cells receive 1 ug long dsRNA and either 500 ng, 1 ug, 2.5 ug or 5 ug short dsRNA. Chemically synthesized short dsRNA is used in one set, and enzymatically synthesized short dsRNA is used in a second set. The cells receiving 2.5 ug long dsRNA also receive short dsRNA molecules as just described. Control cells receive no transfection mixtures. The transfected cells are incubated at 37° C. for 17-20 hours. The media is then removed from the cells and replaced with DMEM (10% FBS). The cells are kept in culture for two weeks, and the media is sampled periodically (e.g., once a day) over a two week period. The media is assayed for SEAP and murine IL-12 expression. Murine IL-12 is assayed using the Quantikine Kit from R&D systems according to the manufacturer's directions. Murine Il-12 is assayed as an indicator of a non-specific, toxic effect such as the effect known to be mediated by long dsRNA and poly (I)(C). Cells are also visualized microscopically for the evidence of cytopathic effect. At eight hours post-transfection, cell lysates are harvested from two of the quadruplicate for measurement of eIF-2alpha phosphorylated and non-phosphorylated levels. This time period following transfection of long dsRNA has been shown to be a peak in expression of phosphorylated eIF-2alpha.

Cytotoxicity/Interferon-Beta Assay

The following parameters of the Type 1 interferon response are monitored following delivery/expression of RNA in RD cells: alpha/beta interferon production, 2'5'-OAS mRNA induction, and PKR and 2'5'-OAS activation. Cytoxicity may also be evaluated through the use of an apoptotic nuclear staining assay (TdT FragEL, DNA Fragmentation Detection Kit, In Situ Apoptosis Assay from Oncogene (Boston, Mass.)), the measurement of antiproliferative responses, and the visual recording of cytopathic effect. For interferon analysis, supernatants are removed from RNA stimulated and control cells at various times points. Interferon-alpha and beta are measured using the human interferon-alpha ELISA kit from Endogen (Rockford, Ill.) and the human interferon-beta ELISA kit from RD1 (Flanders, N.J.) according to manufacturer's directions. The detection of mRNA molecules encoding the p69 human 2',5'-oligoadenylate synthetase is performed by reverse transcriptase PCR using the Titan One Tube Reverse transcriptase PCR Kit (Roche Biochemicals, Nutley, N.J.) according to the manufacturer's directions.

Primers and conditions for the p69 encoding mRNA are described in Hovnanian et al. (Genomics 52(3):267-77, 1998).

Measurement of Phosphorylated eIF-2alpha

PKR activation is monitored by measuring the ratio of phosphorylated to non-phosphorylated eIF2alpha using Western blot analysis and antibodies specific for phosphorylated eIF2a and non-phosphorylated eIF2a. Measurements are made at various time points over 24 hours following dsRNA stimulation. Since activation of PKR has been found to peak at different times depending on the RNA delivered and since the ratio of phosphorylated to unphosphorylated eIF2alpha changes in control cells over 24 hours, each sample is compared to the appropriate time point control and expressed as a fraction of the control value. 2'5'OAS activation is monitored using a ribosomal fragmentation assay (Li et al., J Biol Chem 275(12):8880-8, 2000).

Expected Results

SEAP levels are expected to decline with respect to those levels in the untransfected controls in every set of cells receiving SEAP specific dsRNA. No significant reduction in SEAP is expected in cells receiving only the short dsRNA molecules. However, IL-12 levels are most likely reduced with respect to those seen in cells receiving SEAP long dsRNA and no short dsRNA, due to possible toxicity of long dsRNA. This result indicates that a non-specific effect is responsible for down regulation of expression. In addition, cells transfected with SEAP long dsRNA and no short dsRNA cells may have visible cytopathic effects and have more phosphorylate eIF-2alpha than the untransfected controls. Conversely, cells receiving SEAP dsRNA with any of the short dsRNA molecules may down-regulate SEAP expression without no down-regulating IL-12 expression. In addition, these cells may have few or no visible cytopathic effects and have normal ratios of phosphorlated eIF-2alpha to non-phosphorylated eIF-2alpha. These results would further support the ability of a combination of short dsRNA and long dsRNA to protect cells against the toxic effects induced by long dsRNA alone.

Similar methods can be used to inhibit cytotoxicity induced by short dsRNA that is homologous to a target gene. Short dsRNA can also be used to prevent toxicity when long or short dsRNA is expressed intracellularly under conditions where expression of long or short dsRNA would otherwise be toxic.

EXAMPLE 5

Exemplary Methods for Using dsRNA-Mediated Gene Silencing to Determine or Validate the Function of a Gene Post-transcriptional gene silencing (PTGS) can also be used as a tool to identify and validate specific unknown genes involved in cell function, gene expression, and polypeptide biological activity. Since novel genes are likely to be identified through the methods of the present invention, PTGS is developed for use in validation and to identify novel targets for use in therapies for diseases, for example, cancer, neurological disorders, obesity, leukemia, lymphomas, and other disorders of the blood or immune system.

The present invention features methods to identify unknown targets that result in the modulation of a particular phenotype, an alteration of gene expression in a cell, or an alteration in polypeptide biological activity in a cell, using either a library based screening approach or a non-library based approach to identify nucleic acids that induce gene silencing. The present invention also allows the determination of function of a given sequence. These methods involve the direct delivery of in vitro transcribed dsRNA or the delivery of a plasmid that direct the cell to make its own dsRNA. As described above, short dsRNA or a plasmid encoding short dsRNA is also administered to inhibit dsRNA-mediated toxicity. To avoid problems associated with transfection efficiency, plasmids are designed to contain a selectable marker to ensure the survival of only those cells that have taken up plasmid DNA. One group of plasmids directs the synthesis of dsRNA that is transcribed in the cytoplasm, while another group directs the synthesis of dsRNA that is transcribed in the nucleus.

Identification of Genes by Assaying for a Modulation in Cell Function

Functional identification of novel genes can be accomplished through the use of a number of different assays. For example, cells may be assayed for cell motility, apoptosis, cell growth, cell invasion, vascularization, cell cycle events, cell differentiation, cell dedifferentiation, neuronal cell regeneration, or the ability to support viral replication, as well as other cell functions known in the art. Methods for carrying out such functional assays are well known and are described, for example, in Platet and Garcia (Invasion Metastasis 18:198-208, 1998-1999); Harper et al. (Neuroscience 88:257-267, 1999); and Tomaselli et al. (J. Cell Biol. 105: 2347-2358, 1987), and are also described below.

Functional identification of nucleic acid sequences involved in modulating a particular cell function may be carried out by comparing cells transfected with a dsRNA to control cells that have not been transformed with a dsRNA or that have been mock-transfected, in a functional assay. A cell that has taken up sequences unrelated to a particular function will perform in the particular assay in a manner similar to the control cell. A cell experiencing PTGS of a gene involved in the particular function will exhibit an altered ability to perform in the functional assay compared to the control.

The percent modulation of a particular cell function that identifies a nucleic acid sequence that modulates the function of a cell will vary depending on the assay, phenotype, and the particular nucleic acid affected by PTGS. For each assay, the percent modulation can readily be determined by one skilled in the art, when used in conjunction with controls, as described herein. Desirably the modulation is at least 20%, more desirably at least 30%, 40%, 50%, 60%, 75%, and most desirably at least 90% compared to the control. An increase in the function of a cell can also be measured in terms of fold increase, where desirably, the increase is at least 1.5-fold to 5-fold compared to the control.

Alternatively, the function of a cell may be to affect the function, gene expression, or polypeptide biological activity of another cell, for example, a neighboring cell, a cell that is contacted with the cell in which a PTGS event occurs, or a cell that is contacted with media or other extracellular fluid that the cell in which a PTGS event occurs is contained in. For example, a cell experiencing PTGS of a gene may modulate cell motility, apoptosis, cell growth, cell invasion, vascularization, cell cycle events, cell differentiation, cell dedifferentiation, neuronal cell regeneration, or the ability to support viral replication of a nearby cell, or a cell that is exposed to media or other extracellular fluid in which the transfected cell in which a PTGS event occurs was once contained in. This can be tested by removing the media in which a cell experiencing a PTGS event is occurring and placing it on a separate cell or population of cells. If the function of the separate cell or population of cells is modulated, compared to a cell or population of cells receiving media obtained from cells that had been mock transfected, then one or more of the cells experiencing a PTGS event can affect the function of another cell. The identity of the nucleic acid sequence that causes the modulation can be identified with repeated rounds of selection.

In another method, a single cell experiencing a PTGS event can be placed in proximity of a cell or a population of cells that was not transfected with dsRNA, and the effect of this placement is evaluated for a modulation in the function of the cell or population of cells. If the function of the non-transfected cell or population of cells is modulated, compared to a cell or population of cells in proximity of a cell that was mock transfected, then the cell experiencing a PTGS event contains a nucleic acid sequence that can affect the function of another cell. This nucleic acid sequence can be identified using techniques described herein.

Identification of Genes Using Differential Gene Expression

Differential gene expression analysis can be used to identify a nucleic acid sequence that modulates the expression of a target nucleic acid in a cell. Alterations in gene expression induced by gene silencing can be monitored in a cell into which a dsRNA has been introduced. For example, differential gene expression can be assayed by comparing nucleic acids expressed in cells into which dsRNA has been introduced to nucleic acids expressed in control cells that were not transfected with dsRNA or that were mock-transfected. Gene array technology can be used in order to simultaneously examine the expression levels of many different nucleic acids. Examples of methods for such expression analysis are described by Marrack et al. (Current Opinions in Immunology 12:206-209, 2000); Harkin (Oncologist 5:501-507, 2000); Pelizzari et al. (Nucleic Acids Res. 28:4577-4581, 2000); and Marx (Science 289:1670-1672, 2000).

Identification of Genes by Assaying Polypeptide Biological Activity

Novel nucleic acid sequences that modulate the biological activity of a target polypeptide can also be identified by examining polypeptide biological activity. Various polypeptide biological activities can be evaluated to identify novel genes according to the methods of the invention. For example, the expression of a target polypeptide(s) may be examined. Alternatively, the interaction between a target polypeptide(s) and another molecule(s), for example, another polypeptide or a nucleic acid may be assayed. Phosphorylation or glycosylation of a target polypeptide(s) may also be assessed, using standard methods known to those skilled in the art.

Identification of nucleic acid sequences involved in modulating the biological activity of a target polypeptide may be carried out by comparing the polypeptide biological activity of a cell transfected with a dsRNA to a control cell that has not been transfected with a dsRNA or that has been mock-transfected. A cell that has taken up sequences unrelated to a particular polypeptide biological activity will perform in the particular assay in a manner similar to the control cell. A cell experiencing PTGS of a gene involved in the particular polypeptide biological activity will exhibit an altered ability to perform in the biological assay, compared to the control.

Insertion of Single Units into the Chromosome and Generation of a Cell Line Containing a Single dsRNA Expression Library Integrant If desired, the following methods can be used to generate a cell line in which only one construct encoding a dsRNA (e.g., a long dsRNA) is integrated. These methods may be used to integrate a construct that encodes a candidate dsRNA that may be homologous to a target gene of interest. The construct may also encode a short dsRNA for the inhibition of dsRNA-mediated toxicity. Alternatively, one or more short dsRNA molecules or constructs encoding a short dsRNA may be administered to the cell before, during, or after the administration of the construct encoding the candidate dsRNA.

These methods involve the generation of a target cell line in which the dsRNA expression library is subsequently introduced. Through the use of site-specific recombination, single integrants of dsRNA expression cassettes are generated at the same locus of all cells in the target cell line, allowing uniform expression of the dsRNA in all of the integrants. A dsRNA expression library derived from various cell lines is used to create a representative library of stably integrated cells, each cell within the target cell line containing a single integrant. Cre/lox, Lambda-Cro repressor, and Flp recombinase systems or retroviruses are used to generate these singular integrants of dsRNA expression cassettes in the target cell line (Satoh et al., J. Virol. 74:10631-10638, 2000; Trinh et al., J. Immunol. Methods 244:185-193, 2000; Serov et al., An. Acad. Bras. Cienc. 72:389-398, 2000; Grez et al., Stem Cells. 16:235-243, 1998; Habu et al., Nucleic Acids Symp. Ser. 42:295-296, 1999; Haren et al., Annu. Rev. Microbiol. 53:245-281, 1999; Baer et al., Biochemistry 39:7041-7049, 2000; Follenzi et al. Nat. Genet. 25:217-222, 2000; Hindmarsh et al., Microbiol. Mol. Biol. Rev. 63:836-843, 1999; Darquet et al., Gene Ther. 6:209-218, 1999; Darquet et al., Gene Ther. 6:209-218, 1999; Yu et al., Gene 223:77-81, 1998; Darquet et al., Gene Ther. 4:1341-1349, 1997; and Koch et al., Gene 249:135-144, 2000). These systems are used singularly to generate singular insertion clones, and also in combination.

The following exemplary sequence specific integrative systems use short target sequences that allow targeted recombination to be achieved using specific proteins: FLP recombinase, bacteriophage Lambda integrase, HIV integrase, and pilin recombinase of *Salmonella* (Seng et al. Construction of a Flp "exchange cassette" contained vector and gene targeting in mouse ES cell] A book chapter PUBMED entry 11797223-Sheng Wu Gong Cheng Xue Bao. 2001 September; 17(5): 566-9., Liu et al., Nat. Genet. 2001 Jan. 1; 30(1):66-72., Awatramani et al., Nat. Genet. 2001 November; 29(3):257-9., Heidmann and Lehner, Dev Genes Evol. 2001 September; 211(8-9):458-65, Schaft et al., Genesis. 2001 September; 31(1):6-10, Van Duyne, Annu Rev Biophys Biomol Struct. 2001; 30:87-104., Lorbach et al., J Mol Biol. 2000 Mar. 10; 296(5):1175-81., Darquet et al., Gene Ther. 1999 February; 6(2):209-18., Bushman and Miller, J Virol. 1997 January; 71(1):458-64., Fulks et al., J Bacteriol. 1990 January; 172(1): 310-6). A singular integrant is produced by randomly inserting the specific sequence (e.g., loxP in the cre recombinase system) and selecting or identifying the cell that contains a singular integrant that supports maximal expression. For example, integrants that show maximal expression following random integration can be identified through the use of reporter gene sequences associated with the integrated sequence. The cell can be used to specifically insert the expression cassette into the site that contains the target sequence using the specific recombinase, and possibly also remove the expression cassette that was originally placed to identify the maximally expressing chromosomal location. A skilled artisan can also produce singular integrants using retroviral vectors, which integrate randomly and singularly into the eukaryotic. genome. In particular, singular integrants can be produced by inserting retroviral vectors that have been engineered to contain the desired expression cassette into a naïve cell and selecting for the chromosomal location that results in maximal expression (Michael et al., EMBO Journal, vol 20: pages 2224-2235, 2001; Reik and Murrell., Nature, vol. 405, page 408-409, 2000; Berger et al., Molecular Cell, vol. 8, pages 263-268). One may also produce a singular integrant by cotransfecting the bacterial RecA protein with or without nuclear localization signal along with sequences that are homologous to the target sequence (e.g., a target endogenous sequence or integrated transgene sequence). Alternatively, a nucleic acid sequence that encodes a RecA protein with nuclear localization signals can be cotransfected (Shibata et al., Proc Natl Acad Sci USA. 2001 Jul. 17; 98(15): 8425-32. Review., Muyrers et al., Trends Biochem Sci. 2001 May; 26(5):325-31., Paul et al., Mutat Res. 2001 Jun. 5; 486(1):11-9., Shcherbakova et al., Mutat Res. 2000 Feb. 16; 459(1):65-71., Lantsov. Mol Biol (Mosk). 1994 May-June; 28(3):485-95).

An example utilizing such methods is detailed below.

Creation of the Target Cell Line

Target cell lines are the same cell lines as the ones from which the dsRNA expression libraries will be derived. Target cells are created by transfecting the selected cell line with a bicistronic plasmid expressing a selectable marker, such as G418 and the reporter gene GFP. The plasmid also bears a loxP site. Plasmids integrate randomly into the chromosome through the process of illegitimate recombination at a frequency of $10^{-4}$. Following transfection, cells containing integrants are selected by culturing the cells in the presence of G418 at a concentration determined earlier in a kill curve analysis. About a dozen G418-resistant colonies are expanded and relative GFP expression levels are determined using flow cytometry. DNA from the cells is analyzed by Southern blot analysis to determine integrant copy number. Several single copy integrants exhibiting the highest GFP expression levels are then selected as the target cell lines. GFP expression is monitored because dsRNA encoding templates are then integrated into the loci containing the loxP, GFP, and G418 cassettes in a site-specific fashion, and it is important to ensure that these loci are transcriptionally active. Since cells are selected on the basis of G418 resistance and GFP expression, integration of the plasmid DNA can occur at the loxP site, destroying its function. Several cell lines are therefore chosen to reasonably ensure that at least one integrant has an intact loxP site.

dsRNA Expression Library Construction and Site-Specific Recombination into the Target Cell Line A cDNA library or a randomized library is constructed from RNA isolated from selected cell lines. cDNAs or randomized nucleic acids in the size range of at least 100 to 1000 nucleotides, for example, 500 to 600 nucleotides are optimized during synthesis or are size-selected prior to cloning. In other embodiments, the nucleic acids are at least 10, 20, 30, 40, 50, 60, 70, 80, or 90 nucleotides in length. In yet other embodiments, the number of nucleotides in the nucleic acids is between 5-100 nucleotides, 15-100 nucleotides, 20-95 nucleotides, 25-90 nucleotides, 35-85 nucleotides, 45-80 nucleotides, 50-75 nucleotides, or 55-70 nucleotides, inclusive. In still other embodiments, the number of nucleotides in the nucleic acids is contained in one of the following ranges: 5-15 nucleotides, 15-20 nucleotides, 20-25 nucleotides, 25-35 nucleotides, 35-45 nucleotides, 45-60 nucleotides, 60-70 nucleotides, 70-80 nucleotides, 80-90 nucleotides, or 90-100 nucleotides, inclusive. In other embodiments, the nucleic acid contains less than 50,000; 10,000; 5,000; or 2,000 nucleotides. Each cDNA or randomized nucleic acid is then cloned into a plasmid vector as a dsRNA transcription cassette flanked by two convergent promoters (such as T7 promoters as described herein). The promoters are transcriptionally regulated such that they are off until induced, for example, using a tet ON/OFF system (Forster et al., Nucleic Acids Res. 27:7708-710, 1999; Liu et al., Biotechniques 24:624-628, 6,30-632, 1998; and Gatz, Methods Cell Biol. 50:411-424, 1995). The plasmid also contains the hygromycin resistance gene and an inverted loxP site. The cDNA plasmid library or randomized plasmid library is then co-transfected into the target cell line with a plasmid expressing Cre recombinase, which catalyzes site-specific recombination of the transfected cDNA plasmid or randomized nucleic acid plasmid at the inverted loxP site into the chromosomal locus containing the GFP gene and loxP site (see FIG. 1). The use of the Cre/lox system allows the efficient integration of a plasmid into the chromosome (every transfected cell is predicted to undergo a plasmid integration event). Other site-specific recombination strategies can also be utilized. This results in having every integration to occur at the same site, thereby obviating potential problems with loci dependent expression.

Two days following transfection, cells are incubated in the presence of hygromycin to kill untransfected cells and to select for stable integrants. Transcription of dsRNA is induced, and selected cells are assayed for an alteration in cell function, the biological activity of a target polypeptide, or differential gene expression. Cells expressing dsRNA corresponding to a target nucleic acid exhibit an altered function, for example, increased or decreased cell invasion, motility, apoptosis, growth, differentiation, dedifferentiation, or regeneration, or the ability of the cell to support viral replication. Cells exhibiting altered function are then expanded and the sequence of the integrant is determined. Targets are identified and validated using dsRNA specific for the identified target, or other non-PTGS mediated methods, for example antisense technology.

The regulated transcription system of the present invention provides an advantage to other double stranded expression systems. Following transfection of the dsRNA library, cells contain hundreds to thousands of dsRNA expression cassettes, with concomitant expression of that many expression cassettes. In the dsRNA expression system of the present invention, dsRNA expression cassettes contained within the expression vector integrate into the chromosome of the transfected cell. As described in detail below, every transfected cell integrates one of the double stranded expression cassettes. Desirably no transcription occurs until the episomal (non-integrated) expression vectors are diluted out of the cell such that not more than 5 episomal vectors remain in the cell. Most desirably no transcription occurs until all of the episomal (non-integrated) expression vectors are diluted out of the cell and only the integrated expression cassette remains (a process usually taking about two to several weeks of cell culture). At this time transcription is induced, allowing dsRNA to be expressed in the cells. This method ensures that only one species of candidate dsRNA is expressed per cell, as opposed to other methods that express hundreds to thousands of double stranded species. The use of the above-described system results in the loss of all but one expression cassette, which in turn, permits the rapid screening of libraries without requiring screening multiple pools of libraries to identify the target gene.

EXAMPLE 6

Design and Delivery of Vectors for Intracellular Synthesis of dsRNA For Library Based Screening Approaches to Nucleic Acid Identification Using PTGS The library based screening approaches to nucleic acid identification may induce even less toxicity or adverse side-effects when dsRNA resides in certain cellular compartments. Therefore, expression plasmids that transcribe candidate and/or short dsRNA in the cytoplasm and in the nucleus may be utilized. There are two classes of nuclear transcription vectors: one that is designed to express polyadenylated dsRNA (for example, a vector containing an RNA polymerase II promoter and a poly A site) and one that expresses non-adenylated dsRNA (for example, a vector containing an RNA polymerase II promoter and no poly A site, or a vector containing a T7 promoter). Different cellular distributions are predicted for the two species of RNA; both vectors are transcribed in the nucleus, but the ultimate destinations of the RNA species are different intracellular locations. Intracellular transcription may also utilize bacteriophage T7 and SP6 RNA polymerase, which may be designed to transcribe in the cytoplasm or in the nucleus. Alternatively, Qbeta replicase RNA-dependent RNA polymerase may be used to amplify dsRNA. Viral RNA polymerases, either DNA and RNA dependent, may also be used. Alternatively, dsRNA replicating polymerases can be used. Cellular polymerases such as RNA Polymerase I, II, or III or mitochondrial RNA polymerase may also be utilized. Both the cytoplasmic and nuclear transcription vectors contain an antibiotic resistance gene to enable selection of cells that have taken up the plasmid. Cloning strategies employ chain reaction cloning (CRC), a one-step method for directional ligation of multiple fragments (Pachuk et al., Gene 243:19-25, 2000). Briefly, the ligations utilize bridge oligonucleotides to align the DNA fragments in a particular order and ligation is catalyzed by a heat-stable DNA ligase, such as Ampligase, available from Epicentre.

Inducible or Repressible Transcription Vectors for the Generation of a dsRNA Expression Library If desired, inducible and repressible transcription systems can be used to control the timing of the synthesis of dsRNA. For example, synthesis of candidate dsRNA molecules can be induced after synthesis or administration of short dsRNA which is intended to prevent possible toxic effects due to the candidate dsRNA. Inducible and repressible regulatory systems involve the use of promoter elements that contain sequences that bind prokaryotic or eukaryotic transcription factors upstream of the sequence encoding dsRNA. In addition, these factors also carry protein domains that transactivate or transrepress the RNA polymerase II. The regulatory system also has the ability to bind a small molecule (e.g., a coinducer or a corepressor). The binding of the small molecule to the regulatory protein molecule (e.g., a transcription factor) results in either increased or decreased affinity for the sequence element. Both inducible and repressible systems can be developed using any of the inducer/transcription factor combinations by positioning the binding site appropriately with respect to the promoter sequence. Examples of previously described inducible/repressible systems include lacI, ara, Steroid-RU486, and ecdysone—Rheogene, Lac (Cronin et al. *Genes & Development* 15: 1506-1517, 2001), ara (Khlebnikov et al., J Bacteriol. 2000 December; 182(24):7029-34), ecdysone (Rheogene, www.rheogene.com), RU48 (steroid, Wang X J, Liefer K M, Tsai S, O'Malley B W, Roop D R., Proc Natl Acad Sci USA. 1999 Jul. 20; 96(15):8483-8), tet promoter (Rendal et al., Hum Gene Ther. 2002 January; 13(2):335-42, and Larnartina et al., Hum Gene Ther. 2002 January; 13(2):199-210), or a promoter disclosed in WO 00/63364, filed Apr. 19, 2000.

Nuclear Transcription Vectors for the Generation of a Nuclear dsRNA Expression Library Nuclear transcription vectors for use in library based screening approaches to identify nucleic acids that modulate cell function, gene expression, or the biological activity of a target polypeptide are designed such that the target sequence is flanked on one end by an RNA polymerase II promoter (for example, the HCMV-IE promoter) and on the other end by a different RNA polymerase II promoter (for example, the SCMV promoter). Other promoters that can be used include other RNA polymerase II promoters, an RNA polymerase I promoter, an RNA polymerase III promoter, a mitochondrial RNA polymerase promoter, or a T7 or SP6 promoter in the presence of T7 or SP6 RNA polymerase, respectively, containing a nuclear localization signal. Bacteriophage or viral promoters may also be used. The promoters are regulated transcriptionally (for example, using a tet ON/OFF system (Forster et al., supra; Liu et al., supra; and Gatz, supra) such that they are only active in either the presence of a transcription-inducing agent or upon the removal of a repressor. A single chromosomal integrant is selected for, and transcription is induced in the cell to produce the nuclear dsRNA.

Those vectors containing a promoter recognized by RNA Pol I, RNA Pol II, or a viral promoter in conjunction with co-expressed proteins that recognize the viral promoter, may also contain optional sequences located between each promoter and the inserted cDNA. These sequences are transcribed and are designed to prevent the possible translation of a transcribed cDNA. For example, the transcribed RNA is synthesized to contain a stable stem-loop structure at the 5' end to impede ribosome scanning. Alternatively, the exact sequence is irrelevant as long as the length of the sequence is sufficient to be detrimental to translation initiation (e.g., the sequence is 200 nucleotides or longer). The RNA sequences can optionally have sequences that allow polyA addition, intronic sequences, an HIV REV binding sequence, Mason-Pfizer monkey virus constitutive transport element (CTE) (U.S. Pat. No. 5,880,276, filed Apr. 25, 1996), and/or self splicing intronic sequences.

To generate dsRNA, two promoters can be placed on either side of the target sequence, such that the direction of transcription from each promoter is opposing each other. Alternatively, two plasmids can be cotransfected. One of the plasmids is designed to transcribe one strand of the target sequence while the other is designed to transcribe the other strand. Single promoter constructs may be developed such that two units of the target sequence are transcribed in tandem, such that the second unit is in the reverse orientation with respect to the other. Alternate strategies include the use of filler sequences between the tandem target sequences.

Cytoplasmic Transcription Vectors for the Generation of a Cytoplasmic dsRNA Expression Library Cytoplasmic transcription vectors for use in library based screening approaches to identifying nucleic acids that modulate cell function, gene expression, or the biological activity of a target polypeptide in a cell using PTGS are made according to the following method. This approach involves the transcription of a single stranded RNA template (derived from a library) in the nucleus, which is then transported into the cytoplasm where it serves as a template for the transcription of dsRNA molecules. The DNA encoding the ssRNA is integrated at a single site in the target cell line as described for the nuclear RNA expression library, thereby ensuring the synthesis of only one species of candidate dsRNA in a cell, each cell expressing a different dsRNA species.

A desirable approach is to use endogenous polymerases such as the mitochondrial polymerase in animal cells or mitochondrial and chloroplast polymerases in plant cells for cytoplasmic and mitochondrial (e.g., chloroplast) expression to make dsRNA in the cytoplasm. These vectors are formed by designing expression constructs that contain mitochondrial or chloroplast promoters upstream of the target sequence. As described above for nuclear transcription vectors, dsRNA can be generated using two such promoters placed on either side of the target sequence, such that the direction of transcription from each promoter is opposing each other. Alternatively, two plasmids can be cotransfected. One of the plasmids is designed to transcribe one strand of the target sequence while the other is designed to transcribe the other strand. Single promoter constructs may be developed such that two units of the target sequence are transcribed in tandem, such that the second unit is in the reverse orientation with respect to the other. Alternate strategies include the use of filler sequences between the tandem target sequences.

Alternatively, cytoplasmic expression of dsRNA for use in library based screening approaches is achieved by a single subgenomic promoter opposite in orientation with respect to the nuclear promoter. The nuclear promoter generates one RNA strand that is transported into the cytoplasm, and the singular subgenomic promoter at the 3' end of the transcript is sufficient to generate its antisense copy by an RNA dependent RNA polymerase to result in a cytoplasmic dsRNA species.

Target Cell Line Development for Use with Cytoplasmic dsRNA Expression Libraries The target cell line, using the vector containing the G418 cassette, GFP, and loxP site is designed as described above.

Development of a Cytoplasmic dsRNA Expression Library

DsRNA expression libraries are generated by inserting cDNA or randomized sequences (as described herein) into an expression vector containing a single nuclear promoter (RNA polymerase I, RNA polymerase II, or RNA polymerase III), which allows transcription of the insert sequence. It is desirable that this nuclear promoter activity is regulated transcriptionally (for example, using a tet ON/OFF system described, for example, by Forster et al., supra; Liu et al., supra; and Gatz, supra), such that the promoters are only active in either the presence of a transcription-inducing agent or upon the removal of a repressor. This ensures that transcription is not induced until episomal copies of the vector(s) are diluted out. Vectors also contain a selectable marker, such as the hygromycin resistance gene, and a loxP site. The expression vectors are integrated into the target cell line by methods previously described in this application using Cre recombinase (other site-specific recombinative strategies can be employed, as described previously).

At two days post-transfection, cells are subjected to hygromycin selection using concentrations established in kill curve assays. Surviving cells are cultured in hygromycin to select for cells bearing integrated vectors and to dilute out episomal copies of the vector(s). At this point transcription is induced, and a single stranded RNA (ssRNA) species derived from the insert sequence is transcribed in the nucleus from the nuclear promoter in the inserted vector. The insert is designed such that the insert sequences in the transcript are flanked by bi-directional promoters of RNA bacteriophages (for example, Qbeta or MS2, RNA dependent RNA polymerase promoters) or cytoplasmic viral RNA-dependent RNA polymerase promoter sequences (for example, those of Sindbis or VEEV subgenomic promoters). The nuclear transcript is translocated to the cytoplasm where it acts as a template for dsRNA by an RNA dependent RNA polymerase, which may be provided through co-transfection of a vector that encodes an RNA-dependent RNA polymerase. Alternatively, an integrated copy of the polymerase may be used.

EXAMPLE 7

Non-Library Approaches for the Identification of a Nucleic Acid Sequence that Modulates Cell Functions Cellular Gene Expression, or Biological Activity of a Target Polypeptide Nucleic acid sequences that modulate cell function, gene expression in a cell, or the biological activity of a target polypeptide in a cell may also be identified using non-library based approaches involving PTGS. For example, a single known nucleic acid sequence encoding a polypeptide with unknown function or a single nucleic acid fragment of unknown sequence and/or function can be made into a "candidate" dsRNA molecule. This candidate dsRNA is then transfected into a desired cell type. A short dsRNA or a nucleic acid encoding a short dsRNA is also administered to prevent toxicity. The cell is assayed for modulations in cell function, gene expression of a target nucleic acid in the cell, or the biological activity of a target polypeptide in the cell, using methods described herein. A modulation in cell function, gene expression in the cell, or the biological activity of a target polypeptide in the cell identifies the nucleic acid of the candidate dsRNA as a nucleic acid the modulates the specific cell function, gene expression, or the biological activity of a target polypeptide. As a single candidate dsRNA species is transfected into the cells, the nucleic acid sequence responsible for the modulation is readily identified.

The discovery of novel genes through the methods of the present invention may lead to the generation of novel therapeutics. For example, genes that decrease cell invasion may be used as targets for drug development, such as for the development of cytostatic therapeutics for use in the treatment of cancer. Development of such therapeutics is important because currently available cytotoxic anticancer agents are also toxic for normal rapidly dividing cells. In contrast, a cytostatic agent may only need to check metastatic processes, and by inference, slow cell growth, in order to stabilize the disease. In another example, genes that increase neuronal regeneration may be used to develop therapeutics for the treatment, prevention, or control of a number of neurological diseases, including Alzheimer's disease and Parkinson's disease. Genes that are involved in the ability to support viral replication and be used as targets in anti-viral therapies. Such therapies may be used to treat, prevent, or control viral diseases involving human immunodeficiency virus (HIV), hepatitis C virus (HCV), hepatitis B virus (HBV), and human papillomavirus (HPV). The efficacies of therapeutics targeting the genes identified according to the present invention can be further tested in cell culture assays, as well as in animal models.

Generation of Templates for In Vitro Transcription of dsRNA for Non-Library Based Approaches for Identification of Nucleic Acids Using PTGS Nucleic acid fragments generated, for example, by PCR or restriction endonuclease digestion, encoding the respective target sequences were used as templates for in vitro transcription reactions. PCR fragments are superior to plasmid templates for the synthesis of discrete sized RNA molecules. The PCR fragments encoded at least 20-50 or 100 to 1000, for example, 500 to 600 nucleotides (nts) of the target sequence and were derived from the target mRNA. Known target sequences may be obtained from GenBank and or other DNA sequence databases. Target sequences may also be obtained from cellular RNA molecules that were generated into cDNAs to create a number of different dsRNA molecules. Accordingly, it is possible that the sequence and/or function of the target sequence is not known at the time the dsRNA is generated.

Templates for sense target RNA molecules are generated by placing the bacteriophage T7 promoter at the 5' end of the target coding strand while antisense RNA templates contained the T7 promoter at the 5' end of the non-coding strand. This was achieved by encoding the T7 promoter at the 5' ends of the respective PCR primers. Alternatively SP6 promoters, or a combination of SP6 and T7 promoters may be used.

PCR is performed by conventional methods. The use of both PCR templates in equimolar amounts in an in vitro transcription reaction resulted in primarily dsRNA. The use of two separate fragments has been found to be superior to the use of one PCR fragment containing two T7 promoters, one located at each end of the target sequence, presumably due to transcription interference that occurs during transcription of the dual promoter template. Following PCR amplification, the DNA is subjected to Proteinase K digestion and phenol-chloroform extraction to remove contaminating RNases. Following ethanol precipitation, the DNA is resuspended in RNase-free water at a concentration of 1 to 3 µg/µl.

As an alternative to phenol-chloroform extraction, DNA can be purified in the absence of phenol using standard methods such as those described by Li et al. (WO 00/44914, filed Jan. 28, 2000). Alternatively, DNA that is extracted with phenol and/or chloroform can be purified to reduce or eliminate the amount of phenol and/or chloroform. For example, standard column chromatography can be used to purify the DNA (WO 00/44914, filed Jan. 28, 2000).

Cytoplasmic Transcription Vectors for Non-Library Based Approaches to Nucleic Acid Identification Using PTGS DsRNA molecules for use in non-library based methods for the identification of nucleic acids that modulate cell function, gene expression of a target nucleic acid, or target polypeptide biological activity in a cell can also be generated through the use of cytoplasmic transcription vectors. Such vectors are generated as now described.

The PCR fragments generated for in vitro transcription templates, as described above, are inserted into a cloning vector containing one T7 promoter located just outside the polylinker region. Such a vector is pZERO blunt (Promega Corp.). The PCR fragment is cloned into a restriction site in the polylinker in such a way that the fragment's T7 promoter is distal to the vector's promoter. The resulting vector contains the target sequence flanked by two T7 promoters; transcription from this vector occurs in converging directions. Convergent transcription is desired for these intracellular vectors, due to the uncertainty of getting sense and antisense vectors into the same cell in high enough and roughly equivalent amounts. In addition, the local concentration of antisense and sense RNA molecules with respect to each other is high enough to enable dsRNA formation when the dual promoter construct is used.

A hygromycin resistance cassette is cloned into the pZERO blunt vector as well. The hygromycin resistance cassette contains the hygromycin resistance gene under the control of the Herpes Simplex Virus (HSV) thymidine kinase promoter and the SV40 polyadenlyation signal. The cassette is in a plasmid vector and is flanked at both ends by a polylinker region enabling ease of removal and subsequent cloning. Hygromycin selection was chosen because of the rapidity of death induced by hygromycin as well as extensive in-house experience with hygromycin selection. Alternatively, other selection methods known to those skilled in the art may be used.

The vectors are transfected into the desired cells using standard transformation or transfection techniques described herein, and the cells are assayed for the ability of the dsRNA molecules encoded by the vectors to modulate cell function, gene expression of a target nucleic acid, or the biological activity of a target polypeptide, as described herein.

EXAMPLE 8

Analysis of RNA from Transfected Cells

Regardless of whether a library based screening approach or a non-library based approach was used to identify nucleic acid sequences, in order to measure the level of dsRNA effector molecule within the cell, as well as the amount of target mRNA within the cell, a two-step reverse transcription PCR reaction is performed with the ABI PRISM™ 7700 Sequence Detection System. Total RNA is extracted from cells transfected with dsRNA or a plasmid from a dsRNA expression library using Trizol and DNase. Two to three different cDNA synthesis reactions are performed per sample; one for human GAPDH (a housekeeping gene that should be unaffected by the effector dsRNA), one for the target mRNA, and/or one for the sense strand of the expected dsRNA molecule (effector molecule). Prior to cDNA synthesis of dsRNA sense strands, the RNA sample is treated with T1 RNase. The cDNA reactions are performed in separate tubes using 200 ng of total RNA and primers specific for the relevant RNA molecules. The cDNA products of these reactions are used as templates for subsequent PCR reactions to amplify GAPDH, the target cDNA, and/or the sense strand copied from the dsRNA. All RNA are quantified relative to the internal control, GAPDH.

EXAMPLE 9

Target Sequence Identification

To identify the target sequence affected by a dsRNA, using any of the above-described methods, DNA is extracted from expanded cell lines (or from the transfected cells if using a non-integrating dsRNA system) according to methods well known to the skilled artisan. The dsRNA encoding sequence of each integrant (or non-integrated dsRNA molecule if using a non-library based method) is amplified by PCR using primers containing the sequence mapping to the top strand of the T7 promoter (or any other promoter used to express the dsRNA). Amplified DNA is then cloned into a cloning vector, such as pZERO blunt (Promega Corp.), and then sequenced. Sequences are compared to sequences in GenBank and/or other DNA databases to look for sequence identity or homology using standard computer programs. If the target mRNA remains unknown, the mRNA is cloned from the target cell line using primers derived from the cloned dsRNA by established techniques (Sambrook et al., supra). Target validation is then carried out as described herein.

In the stably integrated dsRNA expression system described above, despite efforts to reduce negative position effects, inefficient dsRNA synthesis by PCR methods may occur. This can be circumvented by rescuing the integrated cDNA or randomized nucleic sequences into replicating plasmids. Rescued plasmids are amenable to amplification in bacteria and to sequencing. Rescue is achieved by re-transfecting the population of cells transfected with the dsRNA expression library with the rescue plasmid and a plasmid encoding Cre recombinase. The rescue plasmid carries a bacterial origin of replication, a bacterial antibiotic selection marker, an SV40 origin of replication, and an SV40 T antigen expression cassette, as well as loxP sites positioned as an inverted repeat to allow Cre-mediated double recombination. The SV40-based origin of replication in the rescue plasmid allows amplification of rescued sequences in the integrated cells. Following rescue, higher levels of transcription are anticipated, thereby favoring dsRNA formation. The cells are then screened for modulations in cell function, target nucleic acid expression, or target polypeptide biological activity changes as described herein.

EXAMPLE 10

Functional Screening for Cell Invasion

Cell invasion is one cell function that may be evaluated in the search for novel genes that are modulated using the methods described herein. Matrigel, a biological extracellular matrix, has properties similar to that of a reconstituted basement membrane and has been used to measure the invasive potential of tumor cells (Platet and Garcia, supra). Cells transfected with randomized or cDNA libraries that have been cloned into PTGS vectors are monitored for their capacity to invade matrigel invasion chambers. Cells that have taken up sequences unrelated to invasion invade the matrigel as efficiently as vector-transfected control cells. Cells experiencing PTGS of genes that are involved in cell invasion invade much less efficiently. If the dsRNA expression cassette is stably integrated in a chromosome, these cells are retrieved and second and third rounds of selection are carried out in order to isolate specific nucleic acid sequences relevant to cell invasion. The effect of these sequences on invasion is ultimately confirmed by their ability to block the formation of tumors in animal models.

Several human cell lines, for example, MDA-MB-231, used by Platet and Garcia (supra), SKBr3, and MCF-7ADR, a more metastatic variant of MCF-7. MDA-MB-231 breast cancer cells (obtained from the American Type Culture Collection) are also transfected with cDNA libraries or randomized nucleic acid libraries constructed into the vectors described above. The cells are also transfected with a short dsRNA or a vector encoding a short dsRNA to inhibit toxicity. Desirably all cells in this assay contain express a single copy of a candidate dsRNA, as described above.

Cells cultured in commercially available 24- or 96-well formatted systems are used to carry out the cell invasion assay. As this screening protocol relies upon repeated rounds of selection, it may be desirable to keep the cell numbers in each well low enough that enrichment is seen in each succeeding round, yet high enough to recover sufficient cells to culture within a reasonable time period. Therefore, culture conditions that result in invasion by greater than 50% of the cells and that still permit recovery from the surface of the matrigel are made optimal. Non-invasive (NIH3T3 cells) or poorly invasive (MCF7) cell lines are analyzed in parallel as negative controls for invasion.

Initially, triplicate cultures of half-log order dilutions from $10^2$ to $10^6$ cells per well are plated. Cells are then recovered by "scrubbing" with a sterile cotton swab in fresh culture media and are seeded into 96-well plates. The number of invasive cells in the matrigel is quantified using either an MTT-based assay (Sasaki and Passaniti, Biotechniques 24:1038-1043, 1998) or a fluorescent indicator (Gohla et al., Clin. Exp. Metastasis 14:451-458, 1996).

Once the appropriate cell densities for the assay have been empirically determined, stable transfected cells are plated in the matrigel cell invasion chambers. Each experiment includes the following controls: a sample of untransfected cells as a reference culture; untransfected cells treated with anti-invasive chemotherapeutic agents, such as taxol or doxorubicin, as a positive control for inhibition of invasion; cells transfected with empty vectors to confirm that the vector alone had no effects on invasion; and cells transfected cells with genes that are known to block invasion in this assay, such as estrogen receptor-α or TIMP-2 (Kohn et al., Cancer Research 55:1856-1862, 1995; and Woodhouse et al., Cancer (Supplement) 80:1529-1536, 1997).

Cells that fail to invade the matrigel are removed from each well to the corresponding wells of a 96-well plate and cultured until macroscopic colonies are visible. It is important to collect cells at more than one time point after plating, since the time it takes for PTGS to be effective may vary, and it may be that different genes are active at different times after plating. Once the cells are transferred to 96-well plates, they are diluted out and taken through successive rounds of re-screening in the invasion assay in order to expand and isolate cell lines with altered invasive ability. As the population becomes more and more enriched for cells with a non-invasive phenotype, the reduction in invasive cells in the matrigel can be better quantified via MTT or fluorescence assays. Ultimately, a large panel of cloned double-stable cell lines is generated.

This assay can also be carried out with cells into which a dsRNA is not stably integrated into a chromosome. The assay is conducted essentially as described above except that multiple rounds of selection and re-screening are not necessary since the cell is transfected with only one candidate dsRNA species. Thus, the target(s) of the PTGS event is readily identifiable using the cloning and sequencing techniques described above.

EXAMPLE 11

Assays to Measure Induction of an RNA Stress Response

If desired any of the standard methods listed below may be performed to measure the ability of short dsRNA to inhibit dsRNA-mediated toxicity.

Assays Performed to Identify RNA Stress Response Induction

The following assays may be performed to measure the induction of an RNA stress response: TUNEL assay to detect apoptotic cells, ELISA assays to detect the induction of alpha, beta and gamma interferon, ribosomal RNA fragmentation analysis to detect activation of 2'5'OAS, measurement of phosphorylated eIF2a as an indicator of PKR (protein kinase RNA inducible) activation, proliferation assays to detect changes in cellular proliferation, and microscopic analysis of cells to identify cellular cytopathic effects. Apoptosis, interferon induction, 2'5' OAS activation, PKR activation, anti-proliferative responses, and cytopathic effects are all indicators for the RNA stress response pathway.

ELISA Assays

Alpha and beta interferon induction are associated with induction of the RNA stress response. Supernatants are removed from the transfected and untreated cells at time points of 1, 2, 7, 17, and 48 hours and every several days for up to one month after the 48 hour time point. Collected supernatants are stored at −80° C. until they are analyzed for the presence of alpha, beta, and gamma interferon using commercially available ELISA kits. The Interferon-alpha ELISA kit is obtained from ENDOGEN (Rockford, Ill.), the Interferon-Beta ELISA kit is obtained from RD1 (Flanders, N.J.), and the Interferon-gamma ELISA kit is obtained from R&D Systems (Minneapolis, Minn.). ELISAs are all performed according to the manufacturer's directions. Alpha, beta, and gamma interferon are desirably not detected at increased levels in cells expressing intracellular dsRNA compared to the corresponding levels in untreated cells. In contrast, considerable levels of beta interferon have been found in cells transfected with poly (I)(C) or with in vitro transcribed dsRNA and ssRNA.

TUNEL Assay

Apoptosis is an end result of the induction of the RNA stress response pathway. Cells are stained for the presence of apoptotic nuclei using a commercially available kit, TdT FragEL, DNA Fragmentation Detection Kit, In Situ Apoptosis Assay from Oncogene (Boston, Mass.). Cells are stained according to the manufacturer's directions. Cells are stained at for example, 2 hours, 7 hours, 17 hours, 2 days, 3 days, 4 days, and 5 days after transfection. Desirably, there is little or no evidence of apoptosis induced dsRNA at any of the time points analyzed.

2'5'OAS Activation

2'5'OAS activation is associated with induction/activation of the RNA stress response pathway. The activation of 2'5'OAS is determined by performing ribosomal RNA fragmentation analysis. Briefly, following transfection, total RNA is extracted from cells using standard procedures. RNA is extracted at the following time points: 2 hours, 7 hours, 17 hours, 48 hours, 3 days, 4 days, and 5 days after transfection. 5-10 µg RNA is analyzed for each sample. RNA samples is first denatured in formaldehyde/formamide RNA sample buffer at 65° C. for 10 minutes prior to being electrophoresed through 0.5×TBE agarose gels. Ribosomal RNA is visualized by staining with ethidium bromide followed by ultraviolet transillumination. Ribosomal RNA fragmentation has been observed in cells transfected with poly (I)(C) and with in vitro transcribed dsRNA.

PKR Activation

The activation of PKR is determined by measuring the levels of eIF2alpha phosphorylation. Briefly, cells are lysed at various times after transfection (2 hours, 7 hours, 19 hours, 48 hours, 3 days, 4 days, and 5 days after transfection) and analyzed for levels of phosphorylated and non-phosphorylated eIF2 alpha. The protocol for lysing cells can be found in the following reference: Zhang F. et al., J. Biol. Chem. 276 (27):24946-58, 2001. This analysis is performed as described for detecting PKR phosphorylation except that antibodies specific for phosphorylated and non-phosphorylated eIF2alpha are used. These antibodies are available from Cell Signaling Technology (Beverly, Mass.).

Cytopathic Effect and Antiproliferative Responses

Cytopathic effect is associated with the RNA stress response. Cytopathic effect is assayed by analyzing cells microscopically using a light microscope. Cells are analyzed at daily intervals throughout the course of the experiment. Cytopathic effect is defined as any or all of the following: cells detaching from surface of well/flask, cells rounding up, an increased number of vacuoles in transfected cells with respect to the control untreated cells, or differences in morphology of cells with respect to the untreated control cells. Cytopathic effects have been found in cells transfected with Poly (I)(C) or with dsRNA made in vitro. Desirably, mild or no cytopathic effects are observed using the methods of the present invention.

Antiproliferative responses are associated with the RNA stress response. Antiproliferative responses are assayed by measuring the division rate of cells. The division rate is determined by counting cell numbers using standard procedures. Cells are counted every few days for the duration of the experiment.

EXAMPLE 12

Optimization of the Concentrations and Relative Ratios of In Vitro or In Vivo Produced dsRNA and Delivery Agent If desired, the optimal concentrations and ratios of dsRNA to a delivery agent such as a cationic lipid, cationic surfactant, or local anesthetic can be readily determined to achieve low toxicity and to efficiently induce gene silencing using in vitro or in vivo produced dsRNA.

Summary of Factors Effecting Nucleic Acid/Cationic Lipid Interactions

Cationic lipid DNA interactions are electrostatic. Electrostatic interactions are highly influenced by the ionic components of the medium. The ability to form stable complexes is also dependent upon the intermolecular interactions between the lipid molecules. At low concentrations, certain inter-lipid interactions are preferred; at higher lipid concentrations, rapid condensates are formed due to higher order interactions. Although local interactions are similar in both of these instances (e.g., phosphoryl groups in the DNA and the charged cationic head group), the long range and inter-lipid interactions are substantially different. Similarly, structurally diverse variants can be obtained simply by changing the charge ratio of the complex by mixing varying amounts of cationic lipid with fixed concentrations of the nucleic acid or vice versa. This variation in the structure of the complexes is evidenced by altered physical properties of the complexes (e.g., differences in octanol partitioning, mobility on density gradients, charge density of the particle, particle size, and transfectability of cells in culture and in vivo) (Pachuk et al. DNA Vaccines—Challenges in Delivery, Current Opinion in Molecular Therapeutics, 2(2) 188-198, 2000 and Pachuk et al., BBA, 1468, 20-30, (2000)). Furthermore, different lipids, local anesthetics, and surfactants differ in their interactions between themselves, and therefore novel complexes can be formed with differing biophysical properties by using different lipids singularly or in combination. For each cell type, the following titration can be carried out to determine the optimal ratio and concentrations that result in complexes that do not induce the stress response or interferon response. At several of these concentrations PTGS is predicted to be induced; however, PTGS is most readily observed under conditions that result in highly diminished cytotoxicity.

Complex Formation dsRNA is either produced by in vitro transcription using the T7 promoter and polymerase or another RNA polymerase, such as an *E. coli* RNA polymerase. dsRNA can also be produced in an organism or cell using endogenous polymerases.

Concentrations of dsRNA specific for a target gene, such as PSA-specific dsRNA, are varied from 50 ng to 5 ug per one million cells, and concentrations of short dsRNA (e.g., random short dsRNA molecules used to inhibit toxicity) are varied from 50 ng to 5 ug per one million cells. The ratio of the number of moles of short dsRNA to moles of target-specific dsRNA to is varied from 1000:1, 1:1, to 1:25. In some instances, 150 ng of a plasmid that encodes a reporter of interest (PSA) to be silenced may be comixed at a concentration between 10 ng and 10 µg. The concentration of cationic lipid, cationic surfactant, local anesthetic, or any other transfection facilitating agent that interacts with the nucleic acid electrostatically are varied at each of the dsRNA concentrations to yield charge ratios of 0.1 to 1000 (positive/negative) (i.e., the ratio of positive charge from lipids or other delivery agents to negative charge from DNA or RNA). The complexes are prepared in water or in buffer (e.g., phosphate, HEPES, citrate, Tris-HCl, Tris-glycine, malate, etc. at pH values that range from 4.0 to 8.5), may contain salt (e.g., 1-250 mM), and may contain glycerol, sucrose, trehalose, xylose, or other sugars (e.g., mono-, di-, or polysaccharide). The mixture is allowed to sit at room temperature, desirably for 30 minutes, and may be stored indefinitely. The complexes are premixed in serum free media. The nucleic acid and the transfecting reagent may be mixed either through direct addition or through a slow mixing process, such as across a dialyzing membrane or through the use of a microporous particle or a device that brings the two solutions together at a slow rate and at low concentrations. In some instances, the two interacting components are mixed at low concentrations, and the final complex is concentrated using a diafilteration or any other concentrating device. Alternatively, if the complexes are formed at high concentrations of either or both of the interacting components, the complexes may be diluted to form an ideal transfection mixture.

Transfection Protocol and Analysis of dsRNA Stress Response

Complexes are added to cells that are ~60-80% confluent in serum free media. The complexes are incubated for various times (e.g., 10 minutes to 24 hours) with the cells at 37° C. and diluted with serum containing media or washed and replated in serum free media. The cells are monitored for toxicity and analyzed at various times for signs of dsRNA response (e.g., TUNNEL assay to detect nicked DNA, phosphorylation of EIF2alpah, induction and activation of 2'5' OAS, or interferon-alpha and -beta). Transfection conditions that result in less than 50%, 25%, 10%, or 1% cytotoxicity or that result in a less than 20, 10, 5, 2, or 1.5-fold induction of a stress response are analyzed to determine if PTGS was efficiently induced.

PSA protein levels are determined in cell culture media using standard methods. The data is normalized to the number of live cells in culture to determine the concentrations required to induce PTGS.

EXAMPLE 13

Figure 2:
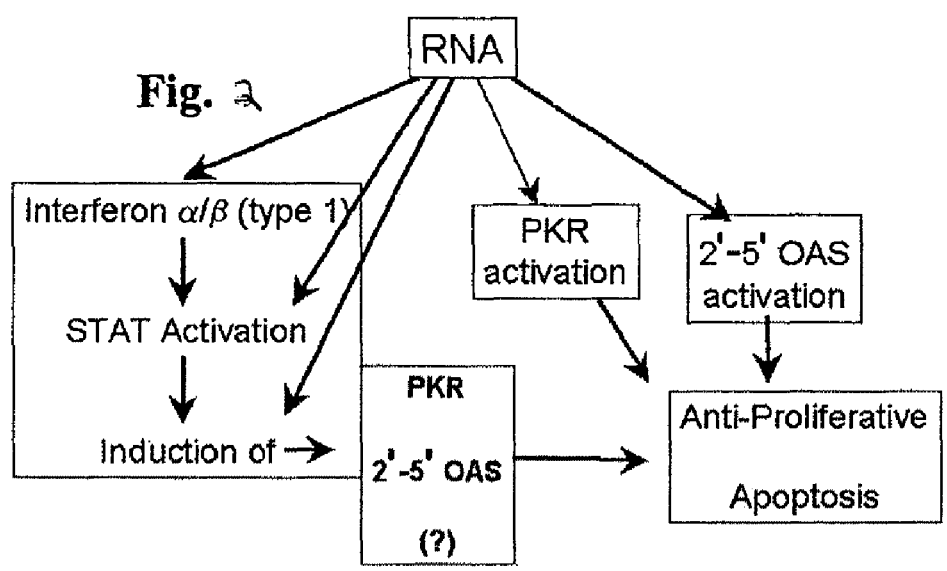
FIG. 2 is a schematic illustration of the RNA stress response pathway, also known as the Type 1 interferon response. The pathway is branched and RNA mediated induction/activation can occur at multiple points in the pathway. RNA (dsRNA and other structures) can act to elicit the production of alpha and or beta interferon in most cell types. Early and key events in the interferon response pathway include interferon-mediated activation of the Jak-Stat pathway, which involves tyrosin-phosphorylation of STAT proteins (STATs). Activated STATs translocate to the nucleus and bind to specific sites in the promoters of IFN-inducible genes thereby effecting transcription of these genes: the expression of which act in concert to push the cell towards apoptosis or to an anti-proliferative state. There are hundreds of interferon-stimulated genes but only two of the better characterized ones, PKR and 2'5'-OAS, have been shown. RNA can also activate the pathway in an interferon and STAT independent manner. In addition, dsRNA/structured RNA can also activate inactive PKR and 2'5'-OAS which are constitutively expressed in many cell types.

Other Methods to Avoid dsRNA-Mediated Activation of the RNA Stress Response Pathway If desired, to further inhibit the RNA stress response pathway, one or more components of the RNA stress response pathway can be mutated or inactivated to avoid induction/activation of the component(s) by dsRNA that is delivered to the cell or animal for the purpose of inducing PTGS. These components, such as those illustrated in FIG. 2, can be knocked out singularly or in combination.

Various standard methods can be used to knockout components of the RNA stress response pathway, such as a promoter, regulatory region, or coding region of PKR, human beta interferon Accession No. M25460), and/or 2'5'OAS (Accession No. NM_003733). Alternatively or additionally, one or more interferon response element (IRE) sequences can be mutated or deleted using a knockout construct designed based on the IRE consensus sequence (Ghislain, et al., J Interferon Cytokine Res. 2001 June 21(6):379-88.), and/or one or more transcription factors that bind IRE sequences, such as STAT1 (Accession number XM_010893), can be mutated or deleted. These methods include the use of antisense DNA/RNA, ribozymes, or targeted gene knockout technology mediated by homologous recombination. One skilled in the art is able to design the appropriate antisense sequences, ribozymes, and vectors for targeted knockouts. For example, targeted knockouts may be prepared by any of the following standard methods: Shibata et al., Proc Natl Acad Sci USA. 2001 Jul. 17; 98(15):8425-32. Review., Muyrers et al., Trends Biochem Sci. 2001 May; 26(5):325-31., Paul et al., Mutat Res. 2001 Jun. 5; 486(1):11-9., Shcherbakova et al., Mutat Res. 2000 Feb. 16; 459(1):65-71., Lantsov. Ideal gene therapy: approaches and prospects Mol Biol (Mosk). 1994 May-June; 28(3):485-95., in Gene Transfer and Expression—A Laboratory Manual editor: Michael Kriegler, Publisher-WH Freeman & Co, New York, N.Y., pages 56-60, 1990). Knockout cells can also be created by standard gene knockout technologies using homologous recombination to alter target sequences, using homologous DNA alone, or as complexes of RecA protein and single stranded DNA homologous to the target sequence(s).

Knockout cells can be readily identified either through the use of an antibiotic resistance marker which when transferred to the chromosome confers resistance to the cell or through the use of dsRNA itself. In particular, dsRNA (e.g., a high concentration of dsRNA) induces apoptosis in wild-type cells while mutant cells survive dsRNA treatment because they cannot mount a stress response. Yet another approach involves performing the dsRNA-induced PTGS experiment in the presence of large concentrations of IRE (dsDNA) oligo, which is expected to titrate activated STAT proteins. These oligos can be delivered intracerllularly using transfecting agents or electroporation.

In another method of preventing the interferon response, cells (e.g., RD cells) are transfected with a T7 RNA polymerase expression vector and a T7 dsRNA expression vector encoding dsRNA homologous to the human protein kinase PKR cDNA (accession number M35663) or homologous to the coding sequence of any other component in the RNA stress response pathway. In one particular example, dsRNA corresponding to nucleotides 190-2000 is encoded by the T7dsRNA expression vector. The expression vectors are similar to those described above and shown in FIG. 2, except that the dsRNA encoding sequence is derived from the human protein kinase PKR cDNA. Transfection in RD cells is performed as described above. Within 2-5 days post-transfection, the cells are functionally PKR negative.

To prevent an interferon response in a system involving stable integration of the nucleic acid containing the dsRNA expression cassette, the vectors used to generate either the loxP integrant or the vector that encodes the dsRNA expression cassette are designed to contain sequences that encode proteins that block the PKR response, such as the Vaccinia virus protein E3 (Romano et al., Molecular and Cellular Biology 18:7304-7316, 1998; Accession No. M36339), or a cellular protein $p58^{IPK}$, which the influenza virus mobilizes to block PKR (Gale et al., Microbiology and Molecular Biology Reviews 64:239-280, 2000; Accession No. XM_032882). Several other viral proteins have also been identified (e.g., Hepatitis C E2; Accession No. S72725) and may be similarly used. These proteins can be expressed in the desired cell types or in animals through the use of any of a number of commercially available mammalian expression vectors or vertebrate expression vectors. Such vectors can be obtained from a number of different manufacturers including Invitrogen (Carlsbad, Calif.) Promega ((Madison, Wis.), or Clontech (Palo Alto, Calif.). An example of such a vector is the pCI-neo Mammalian Expression Vector from Promega.

In yet another alternative, chimeric oligonucleotides may be used to alter target sequences. Methods for inhibiting expression of polypeptides through chimeric oligonucleotides are well known in the art (Igoucheva and Yoon, Human Gene Therapy 11:2307-2312, 2000).

If desired, proteins involved in gene silencing such as Dicer or Argonaut can be overexpressed or activated to increase the amount of inhibition of gene expression (Beach et al., WO 01/68836, filed Mar. 16, 2001).

OTHER EMBODIMENTS

From the foregoing description, it will be apparent that variations and modifications may be made to the invention described herein to adopt it to various usages and conditions.

All publication, patents, and patent applications mentioned in this specification are herein incorporated by reference to the same extent as if each individual publication, patent, or patent application was specifically and individually indicated to be incorporated by reference.

What is claimed is:

1. A method of for identifying a nucleic acid that modulates a detectable phenotype in a cell, said method comprising said steps of:
   (a) transforming a population of cells with a dsRNA expression library comprising long dsRNAs, wherein at least two cells of said population of cells are each transformed with a different nucleic acid from said dsRNA expression library;
   (b) transforming said population of cells with a short dsRNA or a nucleic acid encoding a short dsRNA; and
   (c) assaying for a modulation in said detectable phenotype, wherein said modulation identifies a nucleic acid that is associated with said phenotype,
wherein the ratio between the long dsRNA and short dsRNA is 1:5 to 5:1.

2. The method of claim 1, wherein said modulation in a detectable phenotype is a modulation in the function of a cell, a modulation in the biological activity of a polypeptide, or a modulation in the expression of a target nucleic acid.

3. The method of claim 1, further comprising:
   (d) identifying said nucleic acid by amplifying said nucleic acid and sequencing said amplified nucleic acid.

4. The method of claim 1, wherein said dsRNA expression library comprises cDNAs derived from said cells.

5. The method of claim 1, wherein the double stranded region in said short dsRNA contains between 11 and 30 nucleotides, inclusive.

6. The method of claim 1, wherein the double stranded region in each long dsRNA encoded by said library contains at least 30 nucleotides.

7. The method of claim 1, wherein the double stranded region in each long dsRNA encoded by said library contains over 100 nucleotides.

8. The method of claim 7, wherein the double stranded region in each long dsRNA encoded by said library contains over 200 nucleotides.

9. The method of claim 1, wherein said cell is a vertebrate cell.

10. The method of claim 1, wherein said cell is a mammalian cell.

11. The method of claim 10, wherein said cell is a human cell.

12. A method for treating a disease, disorder, or an infection in an animal, said method comprising introducing into said animal a first agent that provides to said animal a first long dsRNA and a second agent that provides to said animal a short, second dsRNA, wherein said first long dsRNA has substantial sequence identity to a region of a target nucleic acid associated with said disease, disorder, or infection and specifically inhibits said expression of said target nucleic acid, and wherein said short, second dsRNA does not decrease expression of an endogenous nucleic acid in the animal and inhibits dsRNA-mediated toxicity by inhibiting PKR dimerization and activation, and wherein the ratio between the long dsRNA and short dsRNA is 1:5 to 5:1.

13. The method of claim 12, wherein the double stranded region in said second dsRNA contains between 11 and 30 nucleotides, inclusive.

14. The method of claim 12, wherein the double stranded region in said second dsRNA contains between 11 and 15 nucleotides, inclusive.

15. The method of claim 12, wherein the double stranded region in said first long dsRNA contains over 30 nucleotides.

16. The method of claim 15, wherein the double stranded region in said first long dsRNA contains over 200 nucleotides.

17. The method of claim 12, wherein said first and/or second agent is a nucleic acid that encodes a dsRNA.

18. The method of claim 12, wherein said animal is a vertebrate.

19. The method of claim 12, wherein said animal is a mammal.

20. The method of claim 19, wherein said animal is a human.

21. The method of claim 12, wherein said target nucleic acid is associated with a pathogen.

22. The method of claim 21, wherein said pathogen is a virus, bacterium, yeast, or infectious agent.

23. The method of claim 12, wherein the short dsRNA has no homology to endogenously expressed mRNA molecules of the cell.

24. A method for inhibiting the expression of a target nucleic acid in an animal, said method comprising introducing into said animal a first agent that provides to said animal a first long dsRNA and a second agent that provides to said animal a short, second dsRNA, wherein said first dsRNA has substantial sequence identity to a region of said target nucleic acid and specifically inhibits said expression of said target nucleic acid, and wherein said short, second dsRNA does not decrease expression of an endogenous nucleic acid in the animal and inhibits dsRNA-mediated toxicity by inhibiting PKR dimerization and activation, and wherein the ratio between the long dsRNA and short dsRNA is 1:5 to 5:1.

25. The method of claim 24, wherein the double stranded region in said second dsRNA contains between 11 and 30 nucleotides, inclusive.

26. The method of claim 24, wherein the double stranded region in said second dsRNA contains between 11 and 15 nucleotides, inclusive.

27. The method of claim 24, wherein the double stranded region in said first dsRNA contains over 30 nucleotides.

28. The method of claim 27, wherein the double stranded region in said first dsRNA contains over 200 nucleotides.

29. The method of claim 24, wherein said first and/or second agent is a nucleic acid that encodes a dsRNA.

30. The method of claim 24, wherein said animal is a vertebrate.

31. The method of claim 24, wherein said animal is a mammal.

32. The method of claim 31, wherein said animal is a human.

33. The method of claim 24, wherein the short dsRNA has no homology to endogenously expressed mRNA molecules of the cell.

34. A method for inhibiting the expression of a target nucleic acid in a cell, said method comprising introducing into said cell a first agent that provides to said cell a first long double stranded RNA (dsRNA) and a second agent that provides to said cell a short, second dsRNA, wherein said first dsRNA has substantial sequence identity to a region of said target nucleic acid and specifically inhibits said expression of said target nucleic acid, and wherein said short, second dsRNA does not decrease expression of a nucleic acid in the cell and inhibits dsRNA-mediated toxicity by inhibiting PKR dimerization and activation, and wherein the ratio between the long dsRNA and short dsRNA is 1:5 to 5:1.

35. The method of claim 34, wherein the double stranded region in said second dsRNA contains between 11 and 30 nucleotides, inclusive.

36. The method of claim 34, wherein the double stranded region in said second dsRNA contains between 11 and 15 nucleotides, inclusive.

37. The method of claim 34, wherein the double stranded region in said first long dsRNA contains over 30 nucleotides.

38. The method of claim 37, wherein the double stranded region in said first long dsRNA contains over 200 nucleotides.

39. The method of claim 34, wherein said first and/or second agent is a nucleic acid that encodes a dsRNA.

40. The method of claim 34, wherein said cell is a vertebrate cell.

41. The method of claim 34, wherein said cell is a mammalian cell.

42. The method of claim 41, wherein said cell is a human cell.

43. The method of claim 34, wherein the short dsRNA has no homology to endogenously expressed mRNA molecules of the cell.

* * * * *